United States Patent
Gurovich et al.

(10) Patent No.: US 11,135,056 B2
(45) Date of Patent: Oct. 5, 2021

(54) DEVICES AND METHODS OF COMMISSURE FORMATION FOR PROSTHETIC HEART VALVE

(71) Applicant: Edwards Lifesciences Corporation, Irvine, CA (US)

(72) Inventors: Nikolay Gurovich, Hadera (IL); Michael Bukin, Pardes Hana (IL); Alexey M. Tsypenyuk, Haifa (IL); Elena Sherman, Pardes Hanna (IL); Dikla Kersh, Tel Aviv (IL); Boaz Manash, Givat Ada (IL); Liron Tayeb, Peduel (IL); Ziv Yohanan, Kfar Hahoresh (IL); Alexander Barash, Tzoran (IL); Yair A. Neumann, Moshav Sede Varburg (IL); Tomer Saar, Pardes Hanna-Karkur (IL)

(73) Assignee: Edwards Lifesciences Corporation, Irvine, CA (US)

( * ) Notice: Subject to any disclaimer, the term of this patent is extended or adjusted under 35 U.S.C. 154(b) by 366 days.

(21) Appl. No.: 15/978,459

(22) Filed: May 14, 2018

(65) Prior Publication Data

US 2018/0325665 A1 Nov. 15, 2018

Related U.S. Application Data

(60) Provisional application No. 62/614,299, filed on Jan. 5, 2018, provisional application No. 62/506,430, filed on May 15, 2017.

(51) Int. Cl.
*A61F 2/24* (2006.01)

(52) U.S. Cl.
CPC .... *A61F 2/2418* (2013.01); *A61F 2220/0033* (2013.01); *A61F 2220/0075* (2013.01);
(Continued)

(58) Field of Classification Search
CPC ...... A61F 2220/0033; A61F 2220/0075; A61F 2220/0091; A61F 2/2418; A61F 2230/0069; A61F 2/2412
(Continued)

(56) References Cited

U.S. PATENT DOCUMENTS

| 3,409,013 A | 11/1968 | Berry |
| 3,548,417 A | 12/1970 | Kisher |

(Continued)

FOREIGN PATENT DOCUMENTS

| DE | 2246526 A1 | 3/1973 |
| DE | 0144167 C | 6/1985 |

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

(Continued)

*Primary Examiner* — Jerrah Edwards
*Assistant Examiner* — Aren Patel
(74) *Attorney, Agent, or Firm* — Klarquist Sparkman, LLP; Joel B. German

(57) ABSTRACT

A prosthetic heart valve includes an annular frame including a plurality of strut members that is radially collapsible and expandable. A leaflet structure is situated within the frame, and includes a plurality of leaflets having opposing commissure tab portions on opposite sides of the leaflet. Each commissure tab portion is paired with an adjacent commissure tab portion of an adjacent leaflet to form one or more commissures. A commissure support element is positioned at each of the commissures, and comprise a first member and a second member that are separable from each other and (Continued)

configured to receive leaflets therebetween. The first and second members are detached from the frame and spaced radially inwardly from the frame such that the members contact the leaflets radially inward from the frame and limit movement of the leaflets so that they articulate at a location that is spaced radially inwardly from the frame.

24 Claims, 44 Drawing Sheets

(52) U.S. Cl.
CPC ............ *A61F 2220/0091* (2013.01); *A61F 2230/0069* (2013.01)

(58) Field of Classification Search
USPC ............................................ 623/23.72, 2.15
See application file for complete search history.

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |

(56) References Cited

U.S. PATENT DOCUMENTS

| | | | |
|---|---|---|---|
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,672 B2 | 6/2011 | Salahieh et al. |
| 7,993,394 B2 | 8/2011 | Hariton et al. |
| 8,029,556 B2 | 10/2011 | Rowe |
| 8,167,932 B2 | 5/2012 | Bourang et al. |
| 8,291,570 B2 | 10/2012 | Eidenschink et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,747,463 B2 | 6/2014 | Fogarty et al. |
| 9,078,781 B2 | 7/2015 | Ryan et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0173842 A1 | 11/2002 | Buchanan |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0039436 A1 | 2/2004 | Spenser et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0075728 A1 | 4/2005 | Nguyen et al. |
| 2005/0096736 A1 | 5/2005 | Osse et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1* | 2/2006 | Bergheim ........... A61L 27/3882 623/2.18 |
| 2006/0058872 A1 | 3/2006 | Salahieh et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259137 A1 | 11/2006 | Artof et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0275537 A1 | 11/2008 | Limon |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0299452 A1 | 12/2009 | Eidenschink et al. |
| 2009/0319037 A1 | 12/2009 | Rowe et al. |
| 2010/0049313 A1 | 2/2010 | Alon et al. |
| 2010/0168844 A1 | 7/2010 | Toomes et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0319991 A1 | 12/2011 | Hariton et al. |
| 2012/0089223 A1 | 4/2012 | Nguyen et al. |
| 2012/0123529 A1* | 5/2012 | Levi ................ A61F 2/2412 623/2.11 |
| 2012/0259409 A1 | 10/2012 | Nguyen et al. |
| 2013/0023985 A1 | 1/2013 | Khairkhahan et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0330372 A1 | 11/2014 | Weston et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0250591 A1 | 9/2015 | Spenser et al. |

FOREIGN PATENT DOCUMENTS

| | | | |
|---|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1570809 A1 | 9/2005 |
| EP | 2816980 A2 | 12/2014 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 98/29057 A1 | 7/1998 |
| WO | 9933414 A1 | 7/1999 |
| WO | 99/40964 A1 | 8/1999 |
| WO | 99/47075 A1 | 9/1999 |
| WO | 0018333 A1 | 4/2000 |
| WO | 0041652 A1 | 7/2000 |
| WO | 0047139 A1 | 8/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0164137 A1 | 9/2001 |
| WO | 01076510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |

(56) References Cited

FOREIGN PATENT DOCUMENTS

| WO | 0249540 | A2 | 6/2002 |
|---|---|---|---|
| WO | 03047468 | A1 | 6/2003 |
| WO | 2005034812 | | 4/2005 |
| WO | 2005084595 | A1 | 9/2005 |
| WO | 2006014233 | A2 | 2/2006 |
| WO | 2006032051 | A2 | 3/2006 |
| WO | 2006034008 | A2 | 3/2006 |
| WO | 2006111391 | A1 | 10/2006 |
| WO | 2006127089 | A1 | 11/2006 |
| WO | 2006138173 | A3 | 3/2007 |
| WO | 2007047488 | A2 | 4/2007 |
| WO | 2007067942 | A1 | 6/2007 |
| WO | 2007097983 | A2 | 8/2007 |
| WO | 2008005405 | A2 | 1/2008 |
| WO | 2008015257 | A2 | 2/2008 |
| WO | 2008035337 | A2 | 3/2008 |
| WO | 2008091515 | A2 | 7/2008 |
| WO | 2008147964 | A1 | 12/2008 |
| WO | 2008150529 | A1 | 12/2008 |
| WO | 2009033469 | A1 | 3/2009 |
| WO | 2010121076 | A2 | 10/2010 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications;" European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

\* cited by examiner

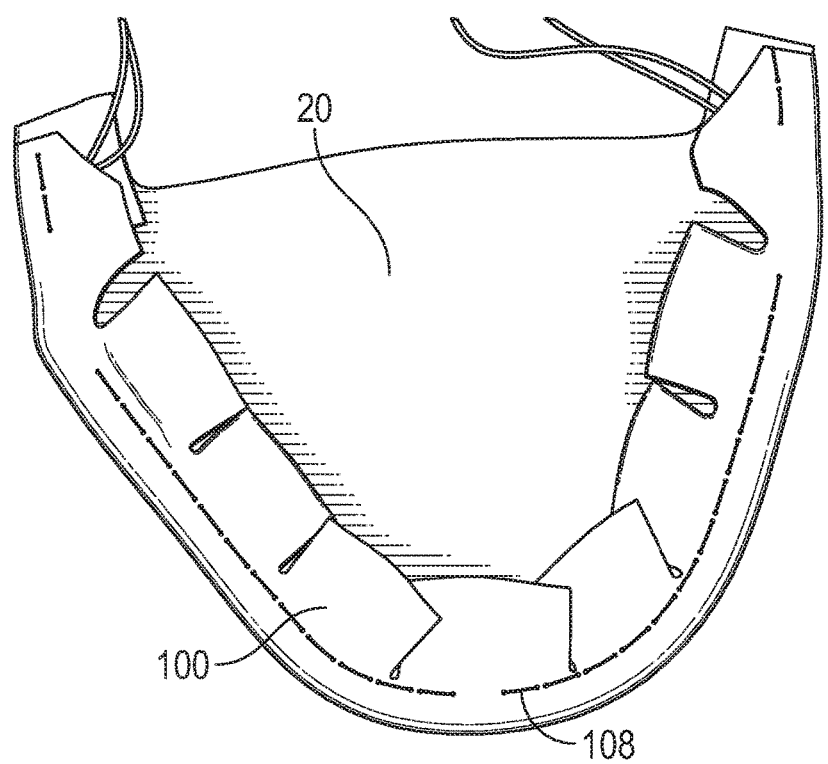
FIG. 11B
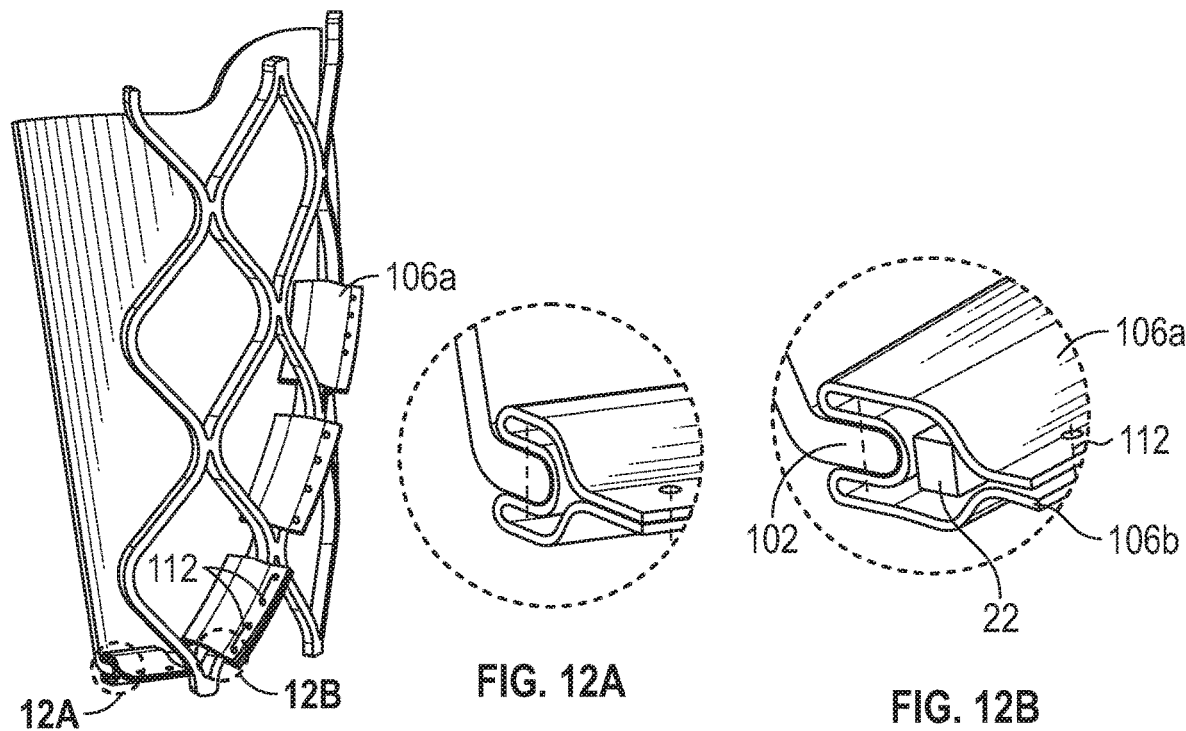
FIG. 12A
FIG. 12B
FIG. 12

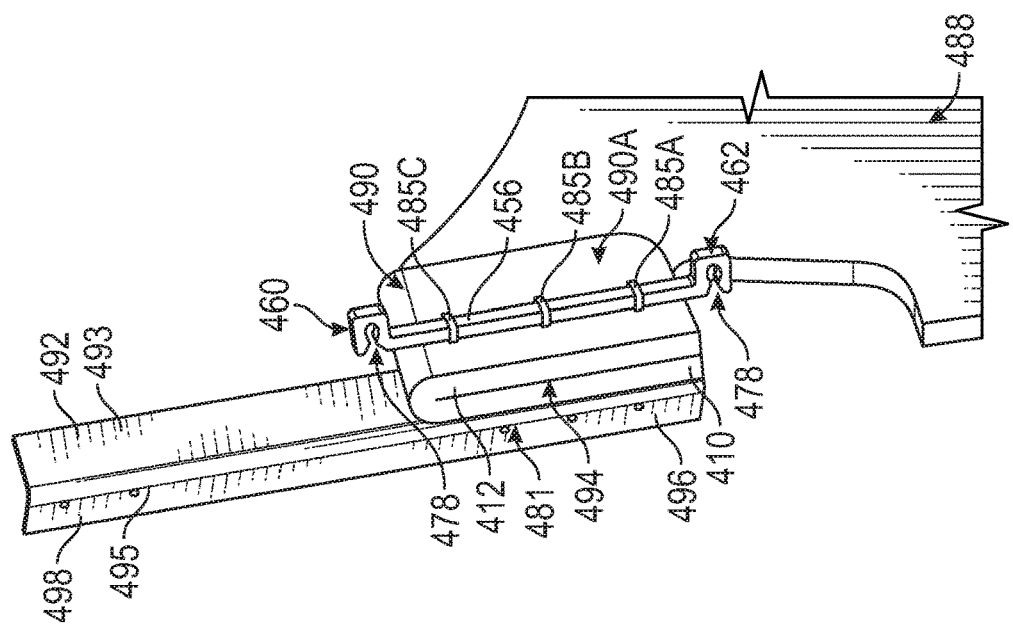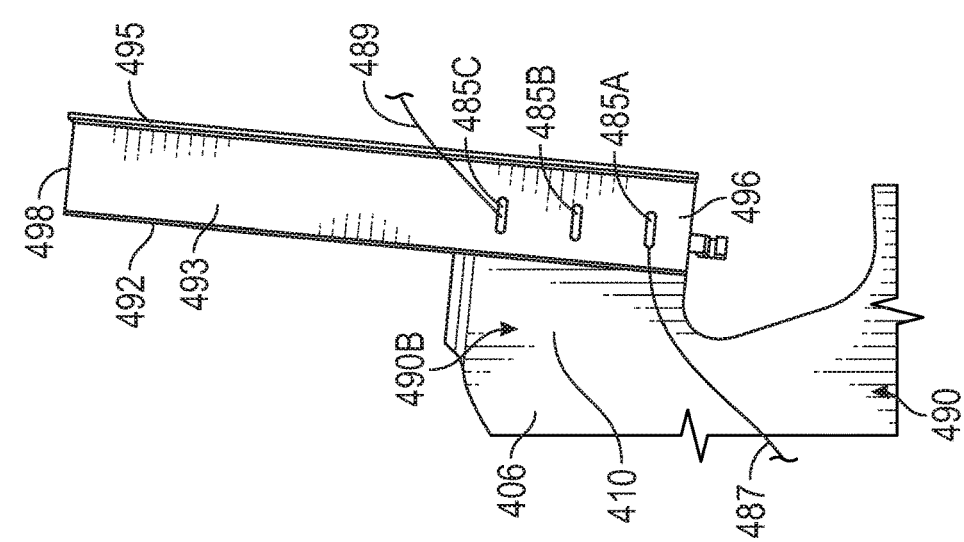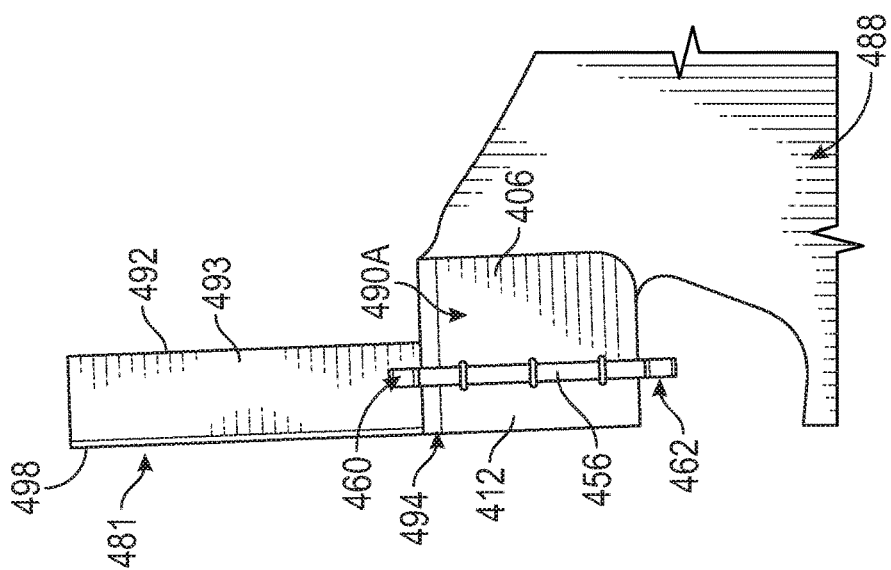

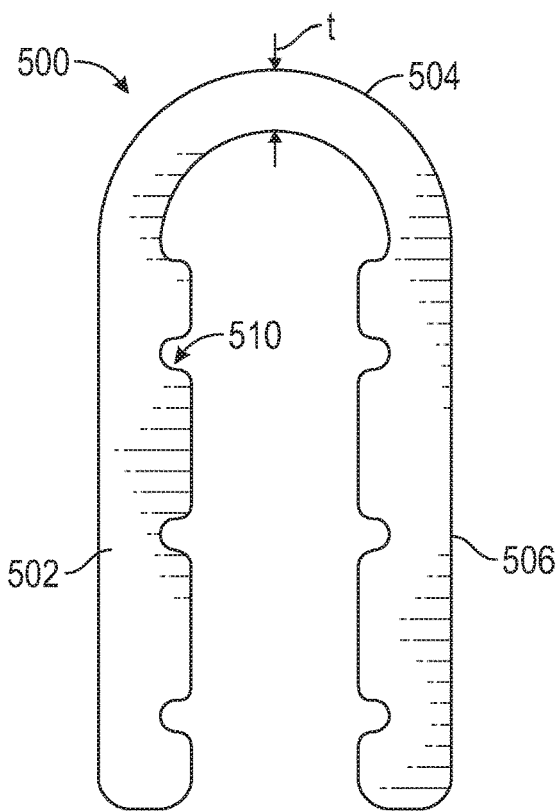
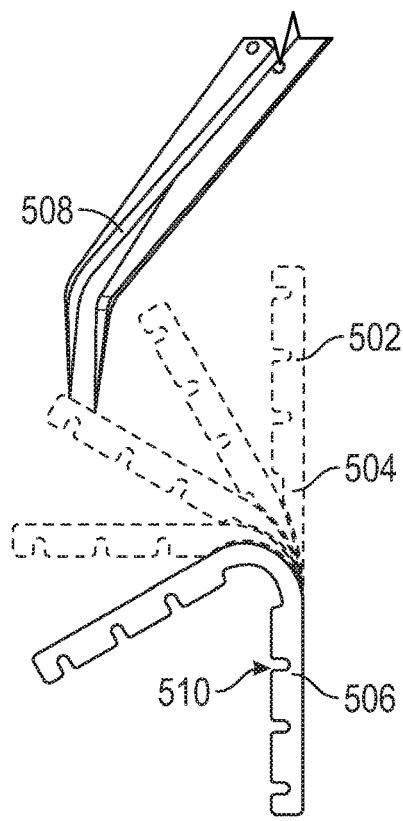
FIG. 59  FIG. 60
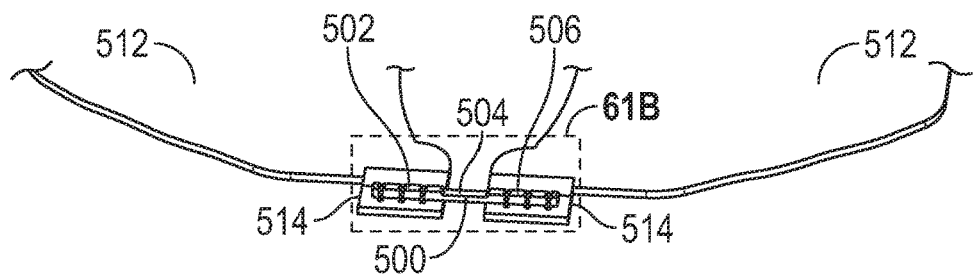
FIG. 61A
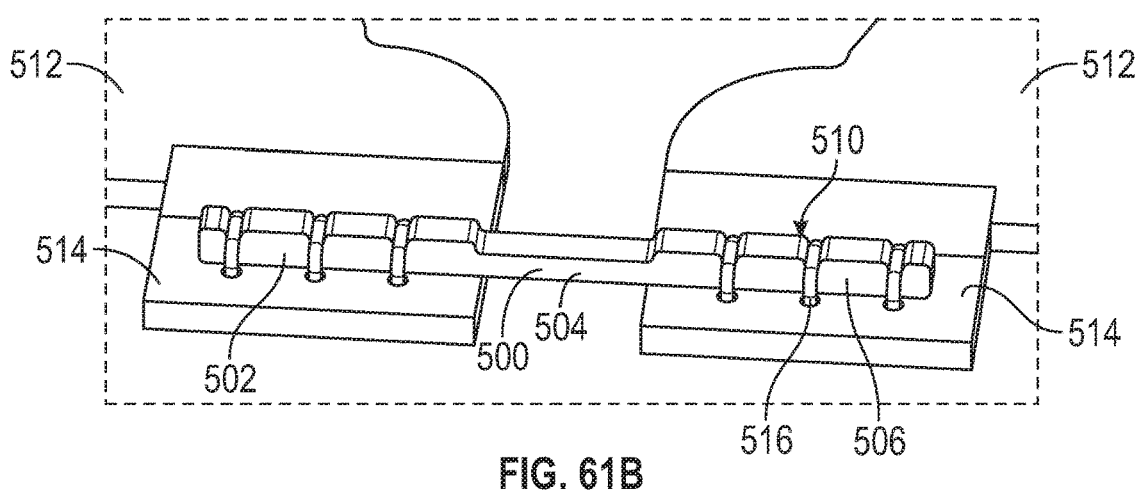
FIG. 61B

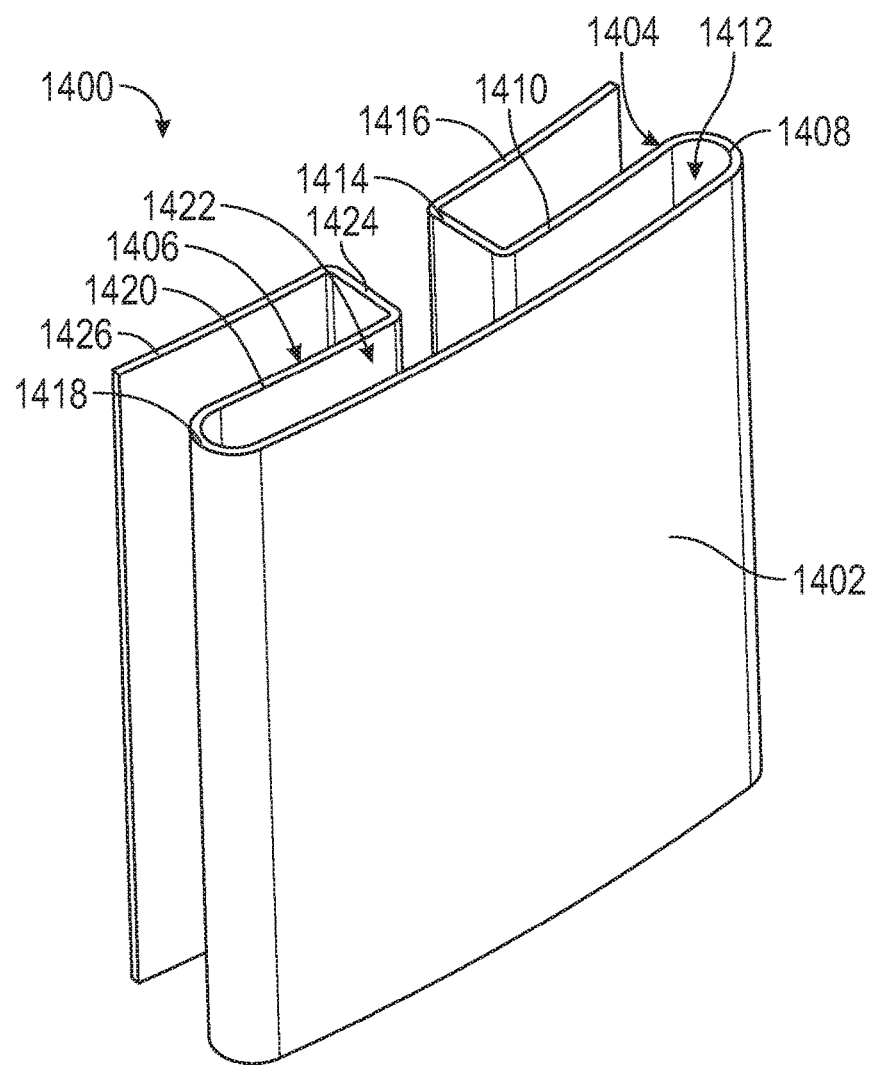
FIG. 94
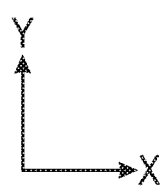
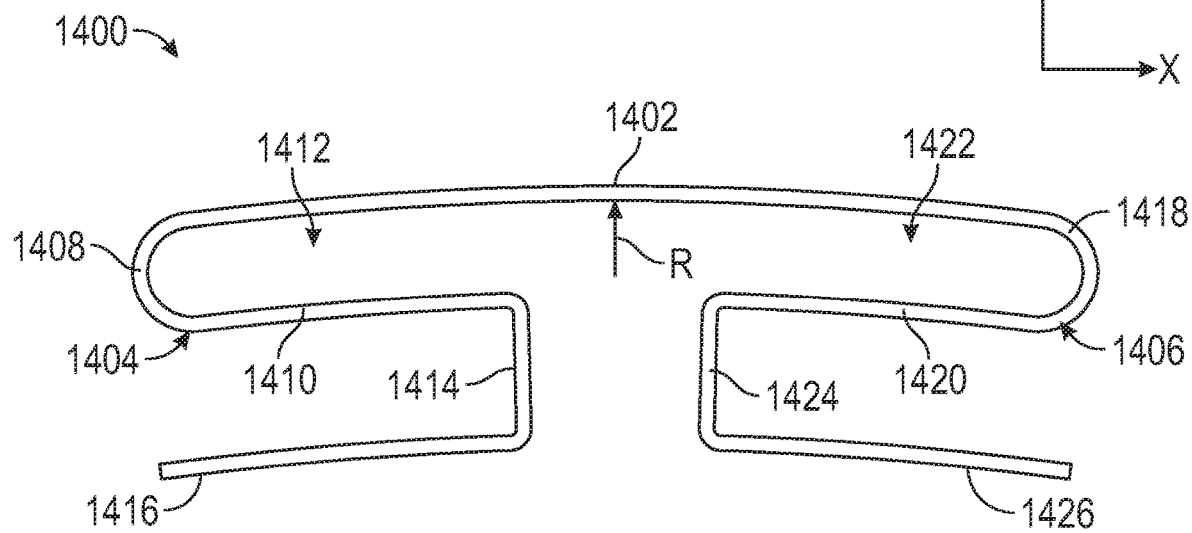
FIG. 95

200
DEVICES AND METHODS OF COMMISSURE FORMATION FOR PROSTHETIC HEART VALVE

CROSS REFERENCE TO RELATED APPLICATION

This application claims the benefit of U.S. Provisional Application No. 62/506,430 filed on May 15, 2017, and U.S. Provisional Application No. 62/614,299 filed on Jan. 5, 2018, all of which are incorporated herein by reference in their entirety.

FIELD

The present disclosure concerns devices and methods for securing leaflets of a prosthetic heart valve together to form a commissure, and securing the leaflets to a frame of the prosthetic valve.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Various surgical techniques may be used to replace or repair a diseased or damaged valve. Due to stenosis and other heart valve diseases, thousands of patients undergo surgery each year wherein the defective native heart valve is replaced by a prosthetic valve. Another less drastic method for treating defective valves is through repair or reconstruction, which is typically used on minimally calcified valves. The problem with surgical therapy is the significant risk it imposes on these chronically ill patients with high morbidity and mortality rates associated with surgical repair.

When the native valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure. By some estimates, more than 50% of the subjects suffering from valve stenosis who are older than 80 years cannot be operated on for valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. Nos. 5,411,522 and 6,730,118, which are incorporated herein by reference, describe collapsible transcatheter heart valves that can be percutaneously introduced in a compressed state on a catheter and expanded in the desired position by balloon inflation or by utilization of a self-expanding frame or stent.

An important design parameter of a transcatheter heart valve is the diameter of the folded or crimped profile. The diameter of the crimped profile is important because it directly influences the physician's ability to advance the transcatheter heart valve through the femoral artery or vein. More particularly, a smaller profile allows for treatment of a wider population of patients, with enhanced safety. Another important design consideration is attachment of the leaflets to the frame of the prosthetic valve to form commissures, which can be difficult and time-consuming. Moreover, in many existing prosthetic valves, the leaflets may articulate against the frame members during valve operation, which can damage the leaflets over time. Accordingly, there is a need for improvements to devices and methods for securing leaflets together to form commissures in prosthetic valves.

SUMMARY

Certain embodiments of the disclosure concern prosthetic heart valves including commissure support elements that cause the leaflets of the prosthetic heart valve to articulate at a location radially inward of the frame. In one representative embodiment, a prosthetic heart valve comprises an annular frame including a plurality of angled strut members. The frame is radially collapsible to a collapsed configuration and radially expandable to an expanded configuration. A leaflet structure is situated at least partially within the frame. The leaflet structure comprises a plurality of leaflets, and each leaflet comprises opposing commissure tab portions on opposite sides of the leaflet. Each commissure tab portion is paired with an adjacent commissure tab portion of an adjacent leaflet to form one or more commissures. The prosthetic valve further comprises a plurality of commissure support elements. A commissure support element is positioned at each of the one or more commissures, and each of the commissure support elements comprises a first member and a second member. The first and second members are separable from each other and configured to receive leaflets therebetween. The first and second members of the commissure support elements are detached from the frame, and spaced radially inwardly from the frame such that the first and second members contact the leaflets radially inward from the frame and limit movement of the leaflets so that the leaflets articulate at a location that is spaced radially inwardly from the frame during valve operation.

In some embodiments, the first member of each commissure support element is secured to one of the adjacent commissure tab portions, and the second member of each commissure support element is secured to the other of the adjacent commissure tab portions.

In some embodiments, the commissure tab portions of each commissure are folded around the first and second members of an adjacent commissure support element.

In some embodiments, the first and second members of each commissure support element are spaced apart from each other, and the prosthetic valve further comprises an attachment member secured to and extending between the commissure tab portions of the leaflets of each commissure.

In some embodiments, each commissure further comprises an outer support member including a main body portion positioned within the frame and an extension portion extending over an outflow end of the frame and situated on the outside of the frame. The attachment member of each commissure is situated around the extension portion of the outer support member such that the commissure is supported within the frame.

In some embodiments, the first and second members of each commissure support element at least partially define a commissure window through which the commissure tab portions of the leaflets extend.

In some embodiments, the first and second members of each commissure support element are secured to each other with sutures.

In some embodiments, the commissure tab portions of each leaflet are folded to form four layers, and the first and second members are situated between second and third layers of the respective commissure tab portions.

In some embodiments, the second layers of the folded commissure tab portions extend radially inwardly of the commissure support elements such that the leaflets articulate about edge portions of the second layers.

In some embodiments, the first and second members of each commissure support element mechanically interlock with each other to form a commissure window.

In some embodiments, the first member of each commissure support element defines openings configured to receive corresponding projections on the second members.

In another representative embodiment, a prosthetic heart valve comprises an annular frame including a plurality of angled strut members. The frame is radially collapsible to a collapsed configuration and radially expandable to an expanded configuration. A leaflet structure is situated at least partially within the frame, and comprises a plurality of leaflets. Each leaflet comprises opposing commissure tab portions on opposite sides of the leaflet, and each commissure tab portion is paired with an adjacent commissure tab portion of an adjacent leaflet to form one or more commissures. The prosthetic heart valve further comprises a plurality of commissure support elements. A commissure support element is positioned at each of the one or more commissures, and each of the commissure support elements comprises a first member and a second member. The first and second members of each commissure support element mechanically interlock with each other to define a commissure window configured to receive the commissure tabs of respective leaflets and limit movement of the commissure tabs such that the leaflets articulate at a location that is spaced radially inwardly from the frame during valve operation.

In some embodiments, the first member of each commissure support element defines openings configured to receive corresponding projections on the second members.

In some embodiments, the first member of each commissure support element is a C-shaped member comprising a main body portion and first and second coupling portions extending laterally from the main body portion, and the openings are defined in the first and second coupling portions.

In some embodiments, each of the coupling portions of the first members of the commissure support elements comprise a pair of laterally-extending tines that define a T-shaped recess, and the second member of each commissure support element comprises a pair of T-shaped extension portions configured to be received in the corresponding T-shaped recesses of the first member.

In some embodiments, the projections of the second members are configured as fastening portions that are bent to secure the first and second members together.

In another representative embodiment, a prosthetic heart valve comprises an annular frame including a plurality of angled strut members. The frame is radially collapsible to a collapsed configuration and radially expandable to an expanded configuration. The prosthetic heart valve further comprises a leaflet structure situated at least partially within the frame, the leaflet structure comprising a plurality of leaflets configured to form one or more commissures. The prosthetic heart valve further comprises a plurality of commissure clamps. A commissure clamp is positioned at each of the one or more commissures, and each of the commissure clamps comprises a main portion, a first clamp member extending radially inwardly from the main portion, and a second clamp member extending radially inwardly from the main portion on the opposite side of the main portion from the first clamp member. The first and second clamp members of the commissure clamps are shaped such that the first clamp member at least partially defines a first leaflet-receiving space radially inward of the main portion and the second clamp member at least partially defines an opposing second leaflet-receiving space radially inward of the main portion. At each respective commissure, one leaflet of the commissure is received in the first leaflet-receiving space of the first clamp member, and the other leaflet of the commissure is received in the second leaflet-receiving space of the second clamp member.

In some embodiments, the frame is a mechanically-expandable frame comprising a plurality of tubular actuators on the frame. The actuators are configured to expand the frame and collapse the frame. The main portions of the commissure clamps can comprise cylindrically-shaped coupling portions, and respective actuators are received in the coupling portions of the commissure clamps such that the commissure clamps are supported by the actuators.

In some embodiments, the leaflets articulate about curved end portions of the first and second clamp members radially inward of the frame.

In some embodiments, the first and second clamp members include one or more curved leaflet-engaging portions configured to engage the leaflets.

In some embodiments, the end portions of the first and second clamp members are radially offset from the leaflet-engaging portions in a direction toward a center of the frame.

In some embodiments, the frame comprises a plurality of commissure windows, the commissure clamps are positioned at the commissure windows, and at least a portion of the first clamp member of each commissure clamp and at least a portion of the second clamp member of each commissure clamp extend through the commissure windows such that the main portions of the commissure clamps and the first and second leaflet-receiving spaces are on the outside of the frame.

In some embodiments, the first clamp member of each commissure clamp is folded against the inside of the frame such that the frame is clamped by the first clamp member, and the second clamp member of each commissure clamp is folded against the inside of the frame such that the frame is clamped by the second clamp member.

In some embodiments, for each commissure, a portion of one of the leaflets is clamped between the main portion and the first clamp member and a portion of the other leaflet is clamped between the main portion and the second clamp member.

The foregoing and other objects, features, and advantages of the disclosed technology will become more apparent from the following detailed description, which proceeds with reference to the accompanying figures.

BRIEF DESCRIPTION OF THE DRAWINGS

FIGS. 10, 10A, 11A, and 11B are various views showing the attachment of the connecting skirt and the leaflet of FIG. 9.

FIGS. 12, 12A, and 12B are various views showing the connection of the connecting skirt of FIG. 9 to the frame of the prosthetic valve of FIG. 8.

FIGS. 42-49 are various views showing the formation of a commissure from two leaflets of the type shown in FIG. 41 using the reinforcing member of FIG. 38A, according to one embodiment.

FIG. 59 is a plan view of a commissure clasp member, according to one embodiment.

FIG. 60 is a side elevation view illustrating bending of the commissure clasp member of FIG. 59 using a tool.

FIGS. 61A, 61B, 62A, 62B, 63A, and 63B are various views illustrating the formation of a commissure using the clasp member of FIG. 59.

FIGS. 94 and 95 illustrate another embodiment of a commissure clamp.

DETAILED DESCRIPTION

Figure 1A:
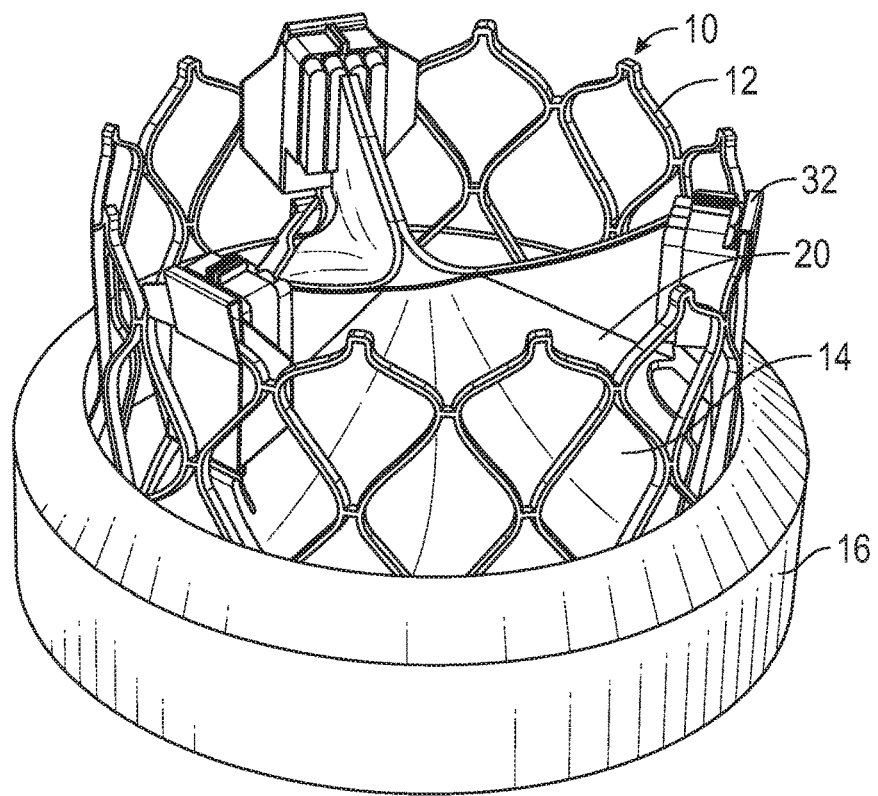
FIGS. 1A-1B are perspective views of a prosthetic heart valve, according to one embodiment.

The present disclosure concerns embodiments of implantable prosthetic devices and, in particular, implantable prosthetic valves, and methods for making such devices. In particular embodiments, the prosthetic device comprises a prosthetic heart valve, and can be configured to be implanted in any of the native heart valves (aortic, mitral, pulmonary, and tricuspid). In addition, the prosthetic heart valve can be, for example, a transcatheter heart valve, a surgical heart valve, or a minimally-invasive heart valve. The prosthetic valve also can comprise other types of valves implantable within other body lumens outside of the heart or heart valves that are implantable within the heart at locations other than the native valves, such as trans-atrial or trans-ventricle septum valves.

In some embodiments, the prosthetic valves described herein can include commissure support elements that are configured to restrict movement of the leaflets adjacent the frame such that the leaflets articulate primarily at a location radially inward of the frame during valve operation. For example, in particular embodiments, the commissure-forming elements can include first and second members that are spaced apart from each other such that the leaflets of a commissure can be received therebetween. In some embodiments, portions of the leaflets, such as commissure tabs, can be folded about the first and second members. In certain embodiments, the first and second members can be assembled together to form a commissure window through which commissure tabs of the leaflets can be inserted. In other embodiments, the first and second members can be secured to each other with, for example, sutures. In still further embodiments, the commissure support elements can comprise integrally-formed clasp or clamp members. For example, in certain embodiments the first and second members can extend from a coupling portion of the clamp member that is coupled to the frame, and the leaflets can articulate about end portions of the first and second members located radially inward of the frame.

The disclosed prosthetic heart valves are particularly suited for implantation in the native aortic valve. In the context of a prosthetic aortic valve, the terms "lower" and "upper" are used interchangeably with the terms "inflow" and "outflow", respectively, for convenience. Thus, for example, the lower end of the prosthetic valve is its inflow end and the upper end of the prosthetic valve is its outflow end in the orientation shown in the drawings. However, it should be understood that the prosthetic valve can be implanted in the reverse orientation. For example, for implantation at the mitral valve position, the upper end of the prosthetic valve is the inflow end and the lower end of the valve is the outflow end.

Figure 1B:
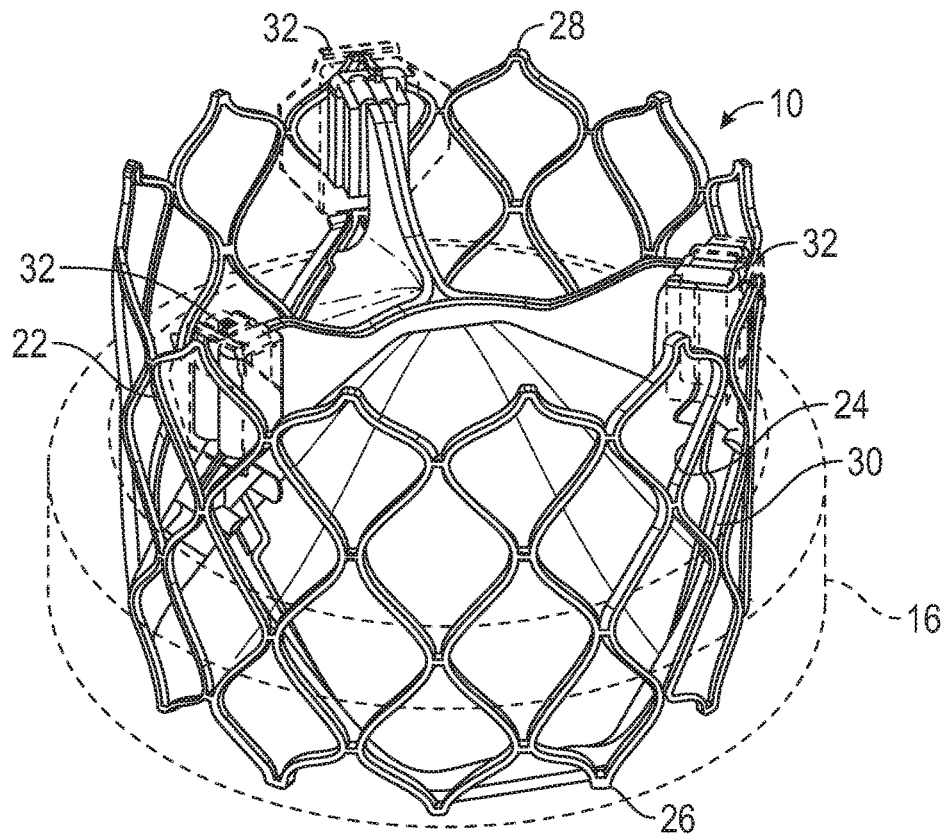

FIG. 1A is a perspective view of a prosthetic heart valve 10, according to one embodiment. The illustrated valve is adapted to be implanted in the native aortic annulus, although in other embodiments it can be adapted to be implanted in the other native annuluses of the heart. The valve 10 can have three main components: a stent, or frame, 12, a valvular structure 14, and a sealing member 16. FIG. 1B is a perspective view of the prosthetic valve 10 with the components on the outside of the frame 12 (including the sealing member 16) shown in phantom lines for purposes of illustration.

The valvular structure 14 can comprise three leaflets 20, collectively forming a leaflet structure, which can be arranged to collapse in a tricuspid arrangement, although in other embodiments there can be greater or fewer leaflets (e.g., one or more leaflets 20). The lower edge of leaflet structure 14 desirably has an undulating, curved scalloped shape. By forming the leaflets with this scalloped geometry, stresses on the leaflets are reduced, which in turn improves durability of the valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the valve. The leaflets 20 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

Each leaflet 20 can be coupled to the frame 12 along its inflow edge 30 (the lower edge in the figures; also referred to as "cusp edges") and at commissures 32 of the valvular structure 14 where adjacent portions of two leaflets are connected to each other, as further described below.

The frame 12 can be made of any of various suitable plastically-expandable materials (e.g., stainless steel, etc.) or self-expanding materials (e.g., Nitinol) as known in the art. When constructed of a plastically-expandable material, the frame 12 (and thus the prosthetic valve 10) can be crimped to a radially compressed state on a delivery catheter and then expanded inside a patient by an inflatable balloon, by mechanical means, or by any equivalent expansion mechanism. When constructed of a self-expandable material, the frame 12 (and thus the prosthetic valve 10) can be crimped to a radially compressed state and restrained in the compressed state by insertion into a sheath or equivalent mechanism of a delivery catheter. Once inside the body, the prosthetic valve can be advanced from the delivery sheath, which allows the valve to expand to its functional size.

Suitable plastically-expandable materials that can be used to form the frame 12 include, without limitation, stainless steel, a nickel based alloy (e.g., a cobalt-chromium or a nickel-cobalt-chromium alloy), polymers, or combinations thereof. In particular embodiments, frame 12 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 12 provides superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

The frame 12 in the illustrated embodiment comprises a plurality of circumferentially extending rows of angled struts 22 defining rows of cells, or openings, 24 of the frame. The frame 12 can have a cylindrical or substantially cylindrical shape having a constant diameter from an inflow end 26 to an outflow end 28 of the frame as shown, or the frame can vary in diameter along the height of the frame, as disclosed in US Publication No. 2012/0239142, which is incorporated herein by reference.

Figure 3:
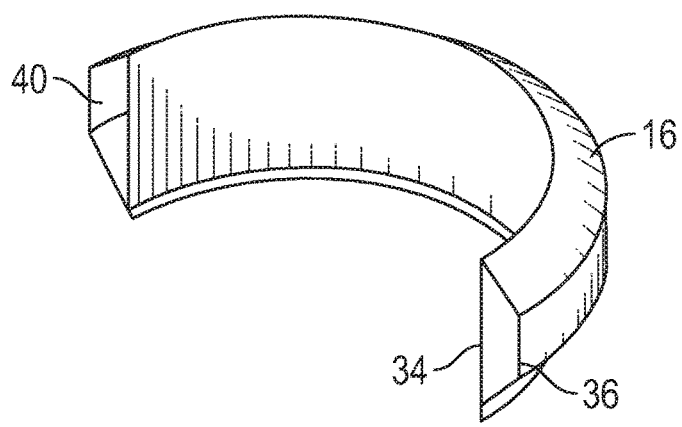
FIG. 3 is a perspective, sectional view of the sealing member of FIG. 1.

The sealing member 16 in the illustrated embodiment is mounted on the outside of the frame 12 and functions to create a seal against the surrounding tissue (e.g., the native leaflets and/or native annulus) to prevent or at least minimize paravalvular leakage. Referring to FIG. 3, the sealing member 16 can comprise an inner layer 34 (which can be in contact with the outer surface of the frame 12) and/or an outer layer 36. The sealing member 16 can be connected to the frame 12 using suitable techniques or mechanisms. For example, the sealing member 16 can be sutured to the frame 12 via sutures 38 (FIG. 5) that can extend around the struts 22 and through the inner layer 34.

Figure 4:
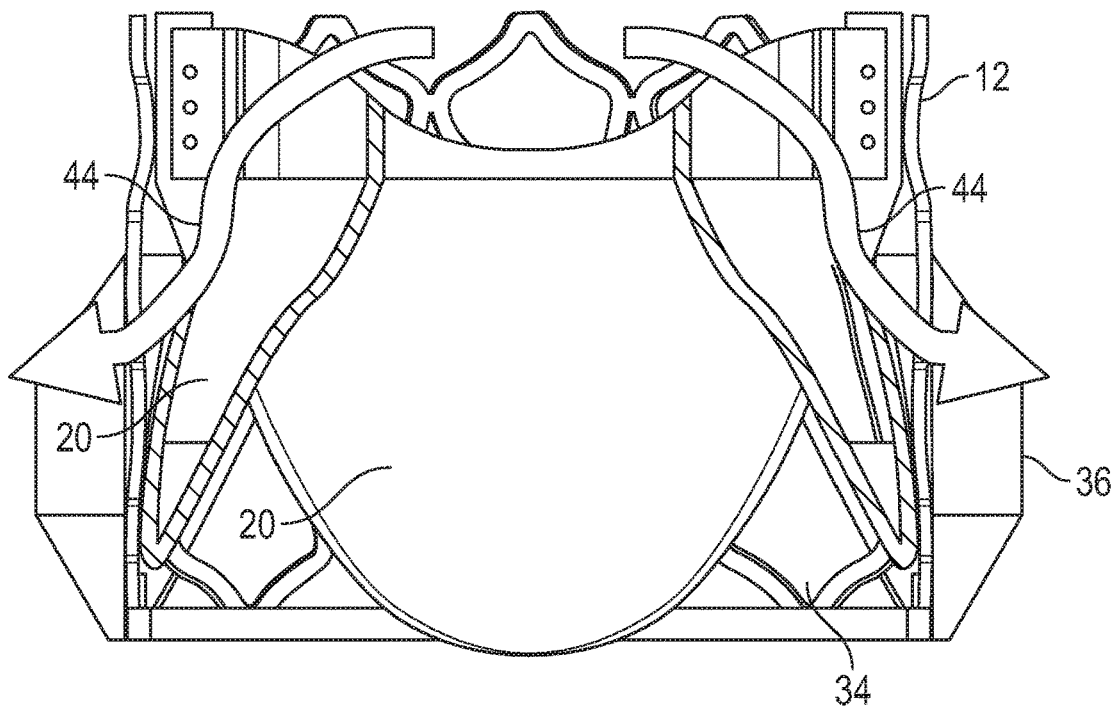
FIG. 4 is a cross-sectional view of the prosthetic heart valve of FIG. 1, showing the flow of retrograde blood through the valve.
Figure 5:
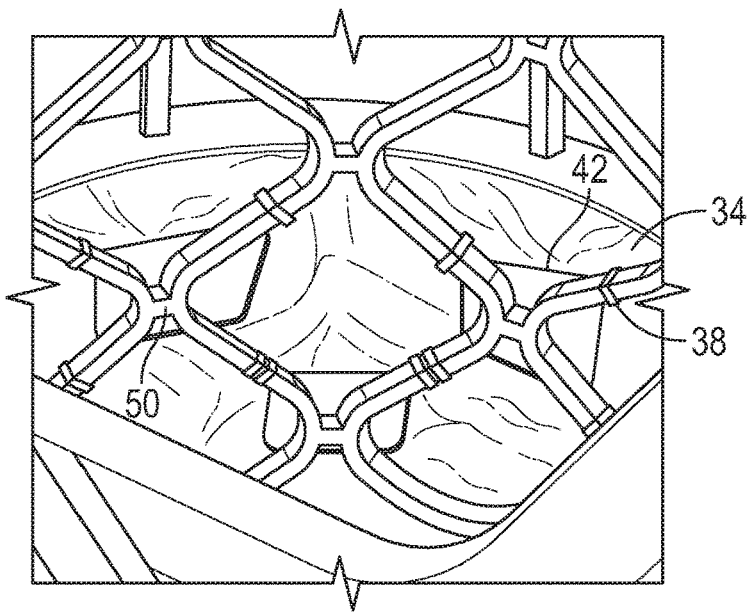
FIG. 5 is an enlarged perspective view showing a portion of the inside of the prosthetic heart valve of FIG. 1.

The outer layer 36 can be configured or shaped to extend radially outward from the inner layer 34 and the frame 12 when the prosthetic valve 10 is deployed. As best shown in FIG. 3, when the prosthetic valve is fully expanded outside of a patient's body, the outer layer 36 can expand away from the inner layer 34 to create a space 40 between the two layers. Thus, when implanted in the body, this allows the outer layer 36 to expand into contact with the surrounding tissue. The inner layer 34 desirably is formed with a plurality of apertures, or openings, 42 (FIG. 5). As best shown in FIG. 4, retrograde blood (indicated by arrows 44) can flow along the outside of the leaflets 20, through the cells 24 of the frame, through the openings 42 in the inner layer 34 and into the space 40 between the inner and outer layers 34, 36, to facilitate expansion of the sealing member 16 and creating a seal against the surrounding tissue. In some embodiments, the outer layer 36 can be formed with a plurality of apertures, or openings, which can allow blood to flow into the sealing member at least during valve deployment.

As shown in FIG. 5, the openings 42 can be centered at junctions 50 where the frame struts 22 intersect, which inhibits material of the inner layer 34 surrounding the openings from protruding inwardly through the frame and contacting the leaflets.

Figure 2:
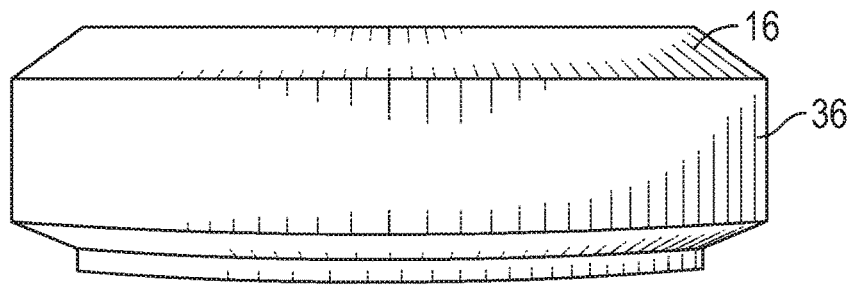
FIG. 2 is a side elevation of the sealing member of the prosthetic heart valve of FIG. 1.

The sealing member 16 can be formed from fabric or non-fabric materials such as PET, PTFE, ePTFE, polyurethane, silicone, polyester, wire mesh, natural tissue (e.g., pericardium) and/or other suitable materials configured to restrict and/or prevent blood-flow therethrough. In some embodiments, the sealing member can be formed from a generally flat strip, folded lengthwise to form the inner and outer layers, and then formed into a tube, such as by welding or stitching the ends together. In other embodiments, the sealing member 16 can be formed by weaving, knitting, or braiding the sealing member into a tubular shape. The bulge in the outer layer 36 can be formed, for example, by shape-setting the material to a desired configuration (e.g., as shown in FIGS. 1 and 2). The shape-setting of the outer layer can allow the outer layer to be self-expandable or induce radial expansion of the outer layer. Additionally or alternatively, the outer layer 36 can be self-expandable by including Nitinol threads in the outer layer.

In alternative embodiments, the inner layer 34 does not have any openings 42, but can be formed from a porous material that allows blood to flow through the inner layer. For example, in some embodiments, the inner layer 34 can be formed from a relatively more porous material than the outer layer 36.

Figure 6:
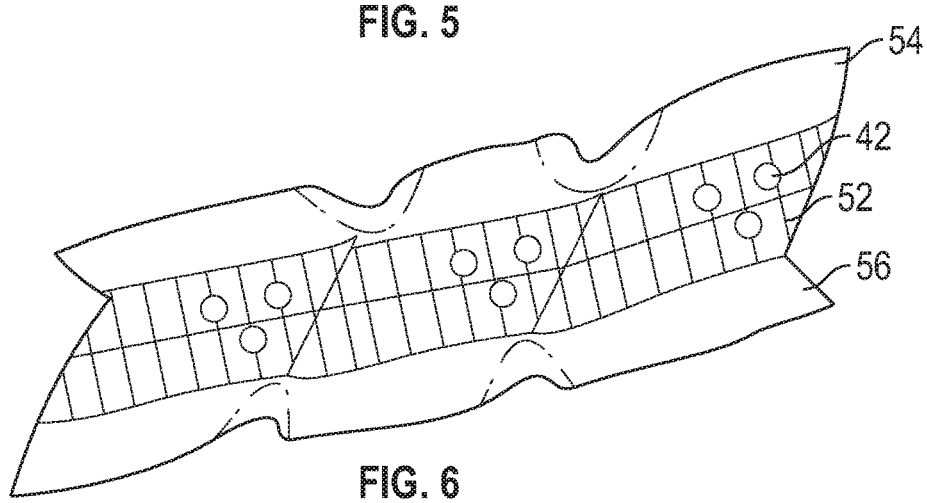
FIG. 6 shows a strip of fabric that can be used to form a sealing member, such as the sealing member of FIG. 3.

FIG. 6 shows a strip of fabric that can be used to form the sealing member 16, according to one embodiment. As shown, a fabric strip can comprise a center section 52 and first and second longitudinal edge portions 54, 56 extending along opposing sides of the center section 52. The center section 52 can include three sets of openings 42 (e.g., three openings in each set in the illustrated embodiment). The openings 42 are positioned to correspond with the position of junctions 50 below the commissures of the prosthetic valve. The first and second longitudinal edge portions 54, 56 can be folded over the center portion 52 and secured to each other, such as with stitching, to form the sealing member. The longitudinal edge portions 54, 56 collectively form the outer layer 36, while the center portion 52 forms the inner layer 34.

Figure 7A:
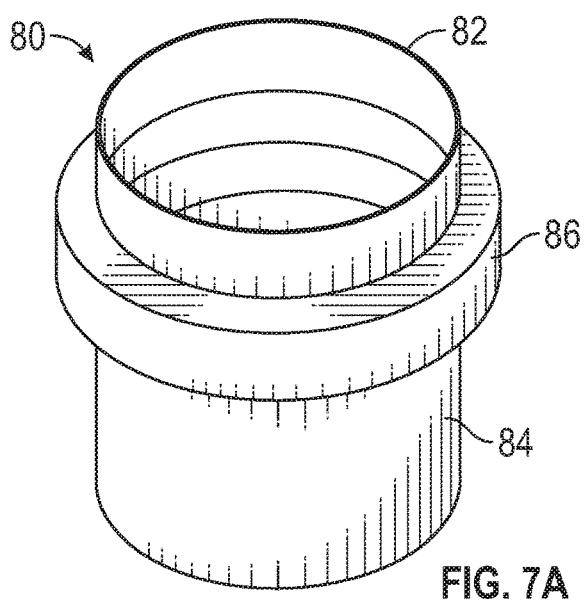
FIGS. 7A-7B are perspective views of exemplary tubular bodies that can be used to form a sealing member for a prosthetic heart valve.
Figure 7B:
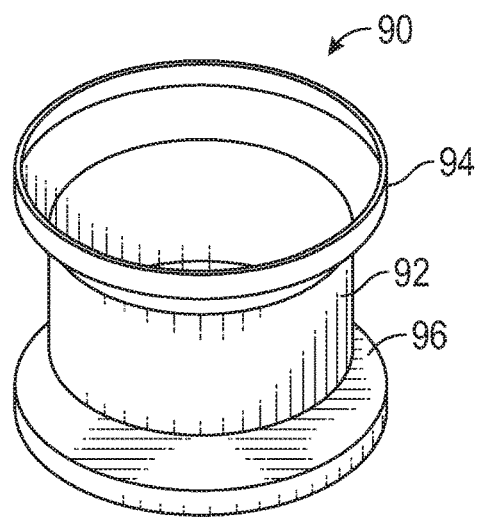

FIGS. 7A and 7B are perspective views of exemplary tubular bodies that can be used to form a sealing member 16. Referring to FIG. 7A, a tubular body 80 can comprise an upper portion 82 and a lower portion 84. The upper portion 82 can include a radial bulge 86. The tubular body 80 can be formed, for example, by three-dimensional weaving, knitting, or braiding. The lower portion 84 can be folded or inverted into the upper portion 82 to form a sealing member having an outer layer formed by the upper portion 82 and an inner layer formed from the lower portion 84.

Referring to FIG. 7B, a tubular body 90 can comprise a cylindrical central portion 92, a flared upper portion 94, and a flared lower portion 96. The tubular body 90 can be formed, for example, by three-dimensional weaving, knitting, or braiding. The upper portion 94 can folded or inverted over the lower portion 94 to form two layers of a sealing member.

Figure 8:
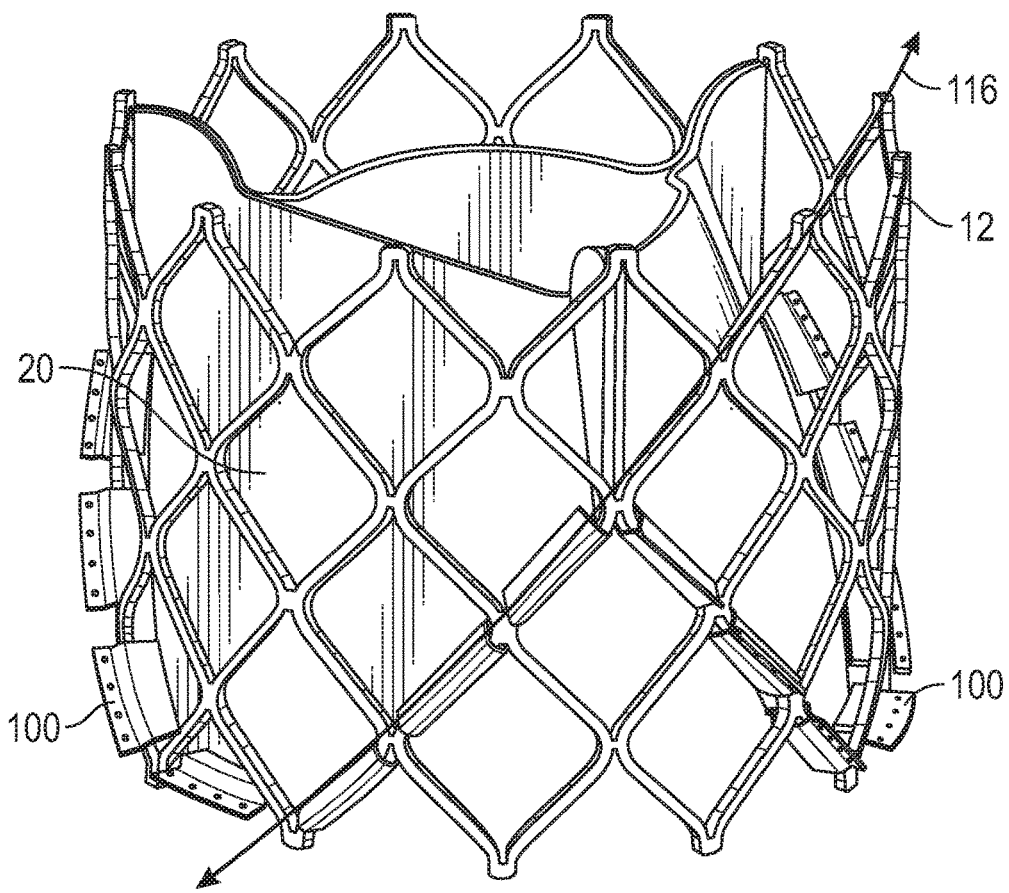
FIG. 8 is a perspective view of a partially assembled prosthetic heart valve showing the attachment of leaflets using connecting skirts, according to one embodiment.
Figure 9:
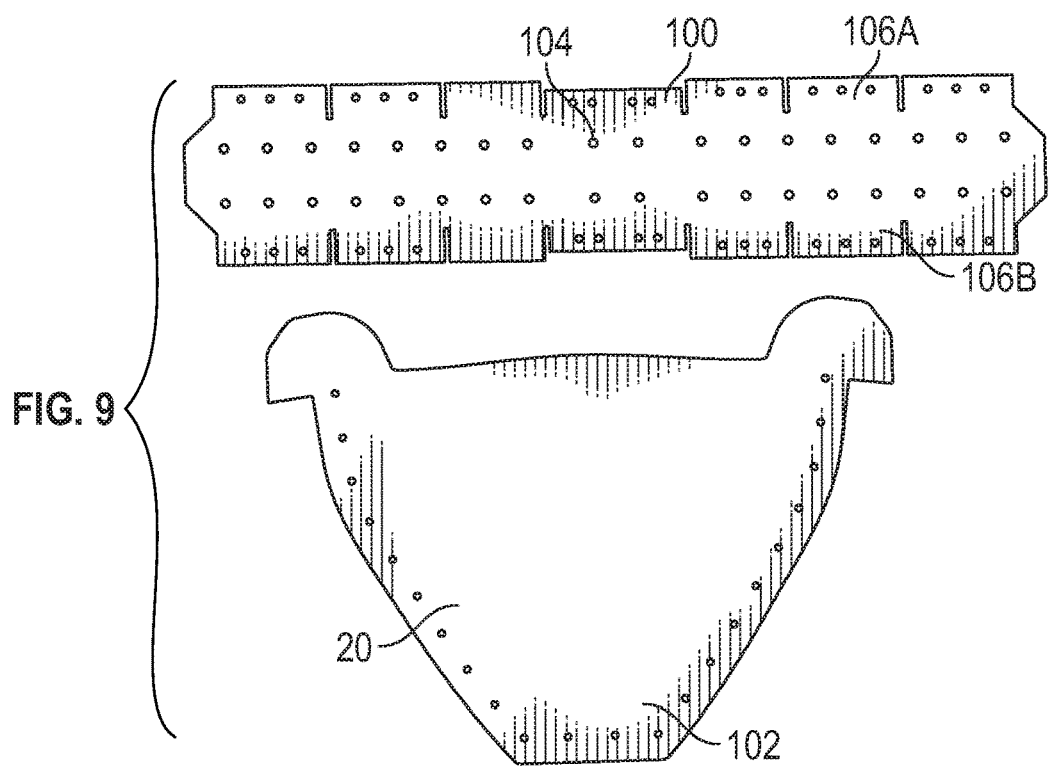
FIG. 9 is a plan view of a leaflet and a connecting skirt used in the prosthetic heart valve of FIG. 8.

FIGS. 8-13 illustrate a technique for mounting the inflow edges 30 of the leaflets 20 to the frame 12, according to one embodiment. In the illustrated embodiment, a connecting skirt 100 is secured to a lower edge portion 102 (also referred to as a cusp edge portion) of each leaflet. As best shown in FIG. 9, each connecting skirt 100 can comprise an elongated, generally rectangular body 104 formed with a plurality of flaps 106a, 106b formed along opposing longitudinal edges of the body 104. The skirt 100 can comprise any suitable synthetic material (e.g., PET) or natural tissue.

Figure 10:
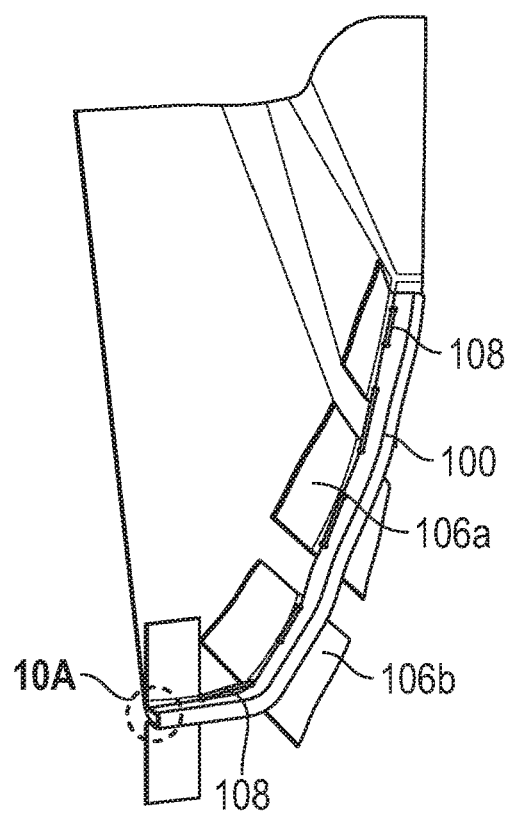
Figure 10A:
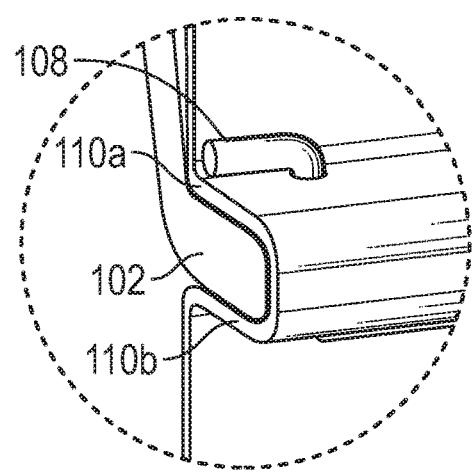
Figure 11A:
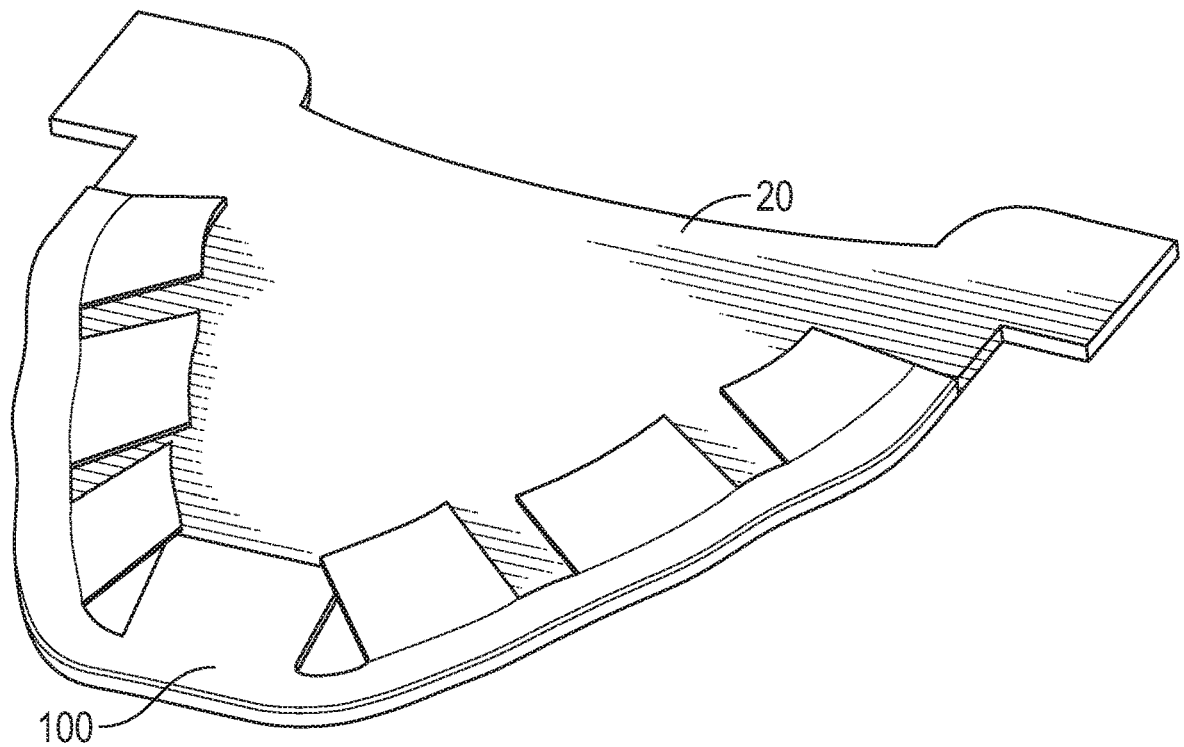

Referring to FIGS. 10 and 10A, to secure a connecting skirt 100 to a leaflet 20, the body 104 is folded along a central longitudinal fold bisecting the body to form folded portions 110a, 110b, which are then placed on opposite sides of the lower edge portion 102 of the leaflet 20 such that the flaps 106a are adjacent the outer surface of the leaflet and the flaps 106b are adjacent the inner surface of the leaflet. A suture can then be used to form stitches 108 that extend through the opposing portions 110a, 110b of the body 104 and the lower edge portion 102 of the leaflet and longitudinally along the length of the lower edge portion 102. FIG. 11A shows a flattened view of the leaflet 20 with the skirt 100 folded around the lower edge portion 102 of the leaflet. FIG. 11B shows a flattened view of the leaflet 20 and the skirt 100 after being secured to the leaflet with stitches 108.

Referring to FIGS. 12, 12A, and 12B, each pair of flaps 106a, 106b are folded away from the leaflet 20 over a respective strut 22 of the frame and secured in place with stitches 112 that extend through the flaps 106a, 106b along a stitching line outside of the frame 12. As best shown in FIG. 12B, the connecting skirt 100 mounts the leaflet to the frame 12 such that the lower edge portion 102 extends radially inwardly at about a 90-degree angle relative to the frame 12. This effectively moves the bending axis of the lower edge portion 102 inwardly away from the inner surface of the frame and toward the center of the frame.

As best shown in FIG. 8, each of the skirts 100 is secured to the frame along a diagonal line 116 extending along the curved surface of the frame defined by a diagonally extending row of struts 22 extending from the inflow end of the frame toward the outflow end. As such, the lower edge portion 102 of each leaflet is also positioned along a respective diagonal line 116 defined by a respective diagonally extending row of struts 22. This advantageously reduces the formation of wrinkles in the leaflets 20 and the crimping profile of the prosthetic valve when the prosthetic valve is radially compressed to its delivery configuration.

Figure 13A:
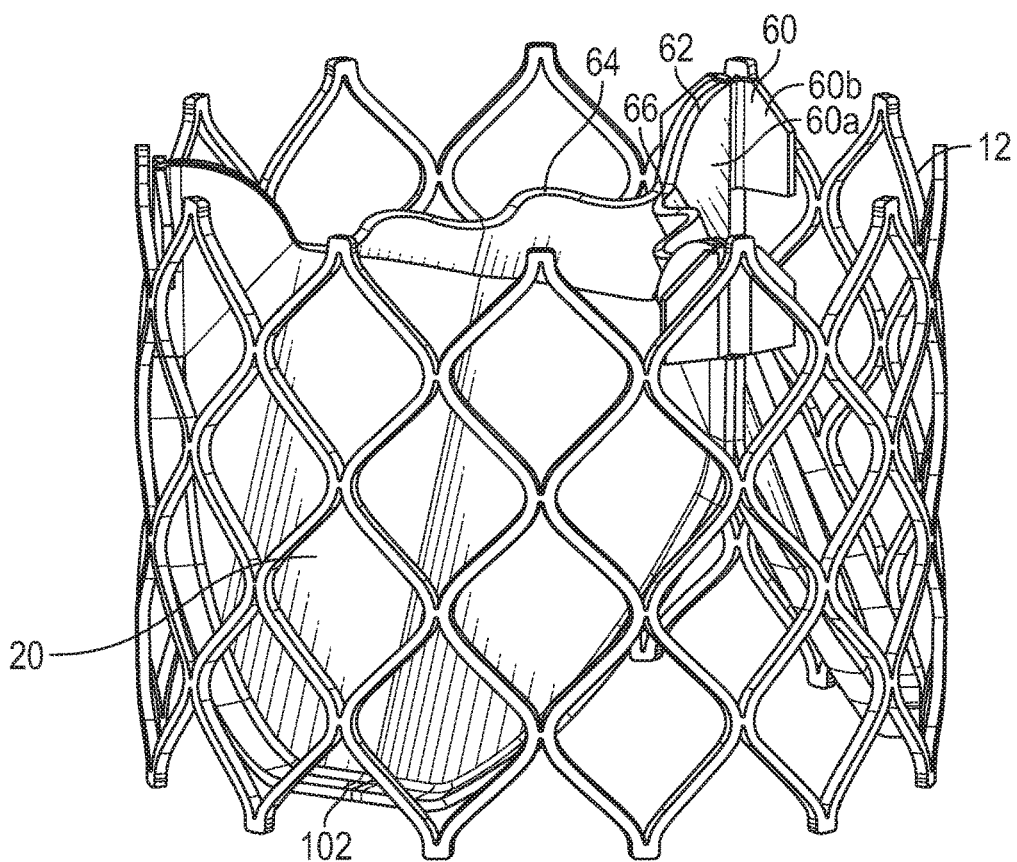
FIG. 13A is a perspective view of a frame of a prosthetic heart valve and leaflets mounted inside the frame, according to one embodiment.
Figure 13B:
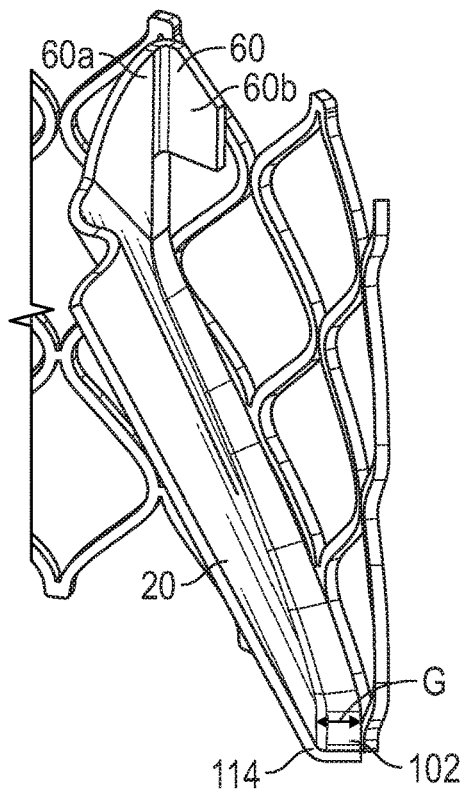
FIG. 13B is an enlarged view of a portion of the frame and one of the leaflets of FIG. 13A.

FIG. 13A is a perspective view of the frame 12 and the leaflets 20 supported in the frame shown in their mounted configuration with the connecting skirts 100 removed for purposes of illustration. FIG. 13B is an enlarged, partial cross-sectional view of the frame and a leaflet. As can be seen, the lower edge portion 102 of the leaflet extends perpendicularly relative to the frame, creating a gap G between the inner surface of the frame and the bending axis 114 of the leaflet 20. Advantageously, this helps prevent or at least minimize contact between the outer surfaces of the leaflets and the frame when the leaflets open during valve operation, thereby inhibiting undesirable abrasion of the leaflets that occurs through contact with the frame. The enlarged spaced between the leaflet and the frame also can promote blood washing over the leaflets at the bending axes of the leaflets.

Moreover, with known prosthetic valves, care must be taken to prevent the leaflets from contacting the inner surface of the frame or extending through the open cells of the frame during crimping so as to prevent damage to the leaflets. For example, known crimping devices for prosthetic valves can include features or accessories that press the leaflets away from the frame or shield the leaflets from contacting the frame during crimping. In contrast, the skirts 100 assist in maintaining the leaflets spaced from inner surface of the frame during crimping of the prosthetic valve without the use of such specially designed crimping accessories.

Further, the connecting skirts 100 can facilitate assembly of the prosthetic valve compared to known assembly techniques. For example, the leaflets and the skirts can be assembled while the leaflets are in a flattened configuration, prior to forming the tubular (annular) configuration the valvular structure 14. Automated or semi-automated techniques can be used to suture the skirts to the leaflets. Also, once the valvular structure is placed inside of the frame, the lower edge portions 102 of the leaflets can be secured to the frame with stitching that is completely outside of the frame 12. This can substantially reduce assembly time as the assembler does not have to thread the needle for forming stitches 112 in and out of the cells 24 of the frame.

As further shown in FIGS. 13A-13B, each leaflet 20 comprises opposing tabs 60. Each tab 60 can be secured to an adjacent tab 60 of an adjacent leaflet 20 to form a commissure that is secured to the frame 12. Each tab 60 can be folded to form a radially extending layer 60a and a circumferentially extending layer 60b facing the frame. Methods for mounting commissures to the frame are described in detail below and can be incorporated into the prosthetic valve shown in FIGS. 13A-13B.

The tab layer 60a can have an inclined edge 62 that extends radially inwardly from a location on the frame to a coaptation edge 64 of the leaflet. The inclined edge 62 also extends in an axial direction from the location on the frame to the coaptation edge 64. This places the center of the coaptation edge 64 (halfway between adjacent commissures) lower than the commissures and the attachment areas of the tabs 60 to the frame. In other words, the commissures are located at different locations along the height of the frame than the centers of the coaptation edges 64. This configuration is advantageous in that it more evenly distributes stress along the tabs 60 during valve cycling. In some embodiments, the entire coaptation edge 64 of a leaflet is below the location where the commissures are attached to the frame, at least when the leaflets are in the closed positions.

During valve cycling, the leaflets can articulate at the inner most edges 66 of the tab layers 60a, which helps space the leaflets away from the frame during normal operation of the prosthetic valve. This is particular advantageous in cases where the prosthetic valve is not fully expanded to its nominal size when implanted in a patient. As such, the prosthetic valve can be implanted in a wider range of patient annulus sizes. Under relatively higher forces, such as when the prosthetic valve is radially compressed for delivery, the leaflets can splay apart from each other at the frame to relieve stress on the leaflets.

The commissures and the coaptation edges of the leaflets typically are relatively bulky portions of leaflets and can inhibit full radial compression of the prosthetic valve if they are at the same height along the frame. Another advantage of the commissure tabs 60 shown in FIGS. 13A-13B is that the commissures and the coaptation edges are separated from each other in the axial direction when the prosthetic valve is radially compressed for delivery into a patient's body. Separating these portions of the leaflets reduces the overall crimp profile of the prosthetic valve.

Figure 14:
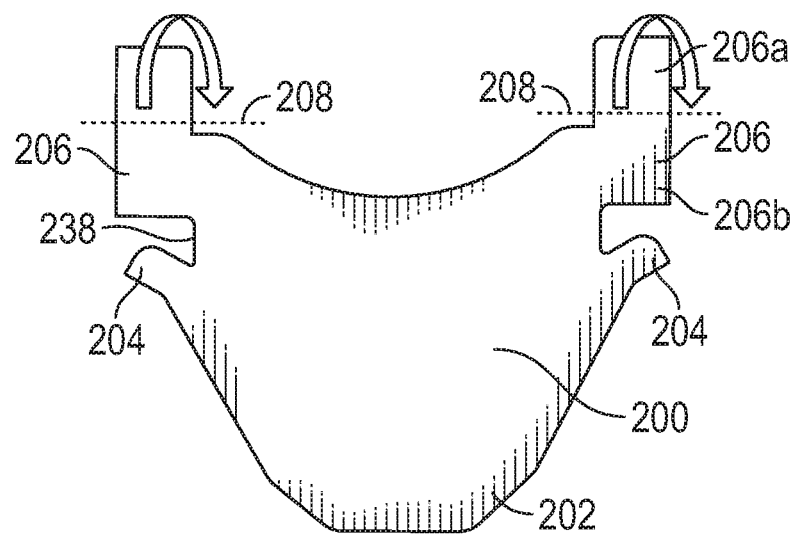
FIG. 14 is a plan view of a leaflet that can be used in a prosthetic heart valve, according to one embodiment.
Figure 15:
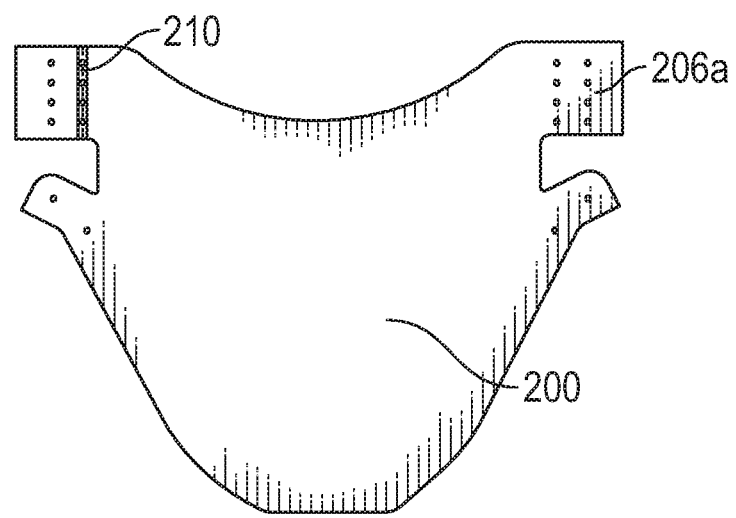
FIGS. 15, 16, and 17 show the formation of one-half of a commissure using the leaflet of FIG. 14, according to one embodiment.

FIGS. 14-18 show a technique for mounting the commissures of a valvular structure to a frame, such as the commissures 32 to the frame 12, according to one embodiment. FIG. 14 shows a leaflet 200 having a lower edge portion 202 that can be mounted to the frame 12 using any of the previously described embodiments. The lower edge portion 202 terminates at its upper ends at two laterally projecting integral lower tabs 204. Projecting from the upper corners of the leaflet 200 are integral upper tabs 206 (also referred to as commissure tabs). The upper tabs 206 can be spaced from the lower tabs 204 by laterally extending gaps or recesses 238 formed in the leaflet.

Figure 18:
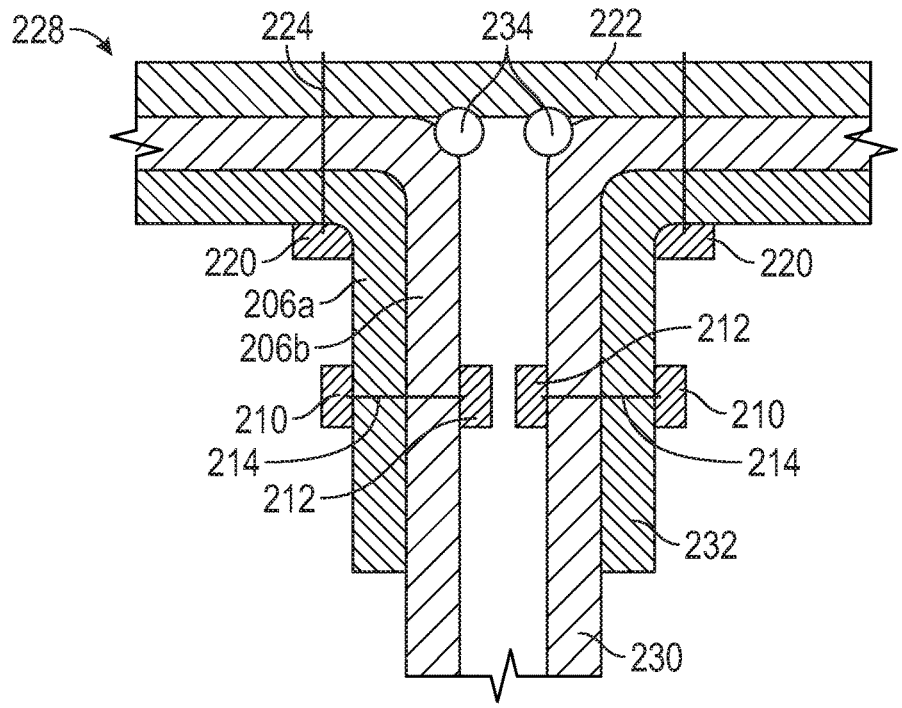
FIG. 18 is a cross-sectional view of a commissure formed from two leaflets of the type shown in FIG. 14, according to one embodiment.

To assemble the commissure, each upper tab 206 is folded along a horizontal fold line 208 to form first and second tab layers 206a, 206b, as shown in FIG. 14 (see also FIG. 18). A first vertically extending reinforcing member 210 can be placed against the first tab layer 206a adjacent its inner edge. A second vertically extending reinforcing member 212 can be placed against the second tab layer 206b opposite the first reinforcing member 210. The first and second tab layers 206a, 206b can be secured to each other with stitching 214 that extends through the first and second tab layers 206a, 206b and the first and second reinforcing members 210, 212.

Figure 16:
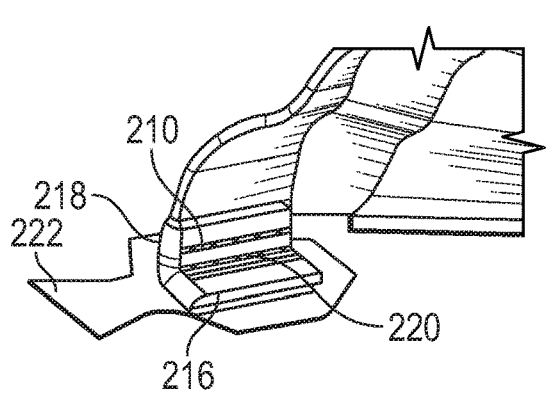
Figure 17:
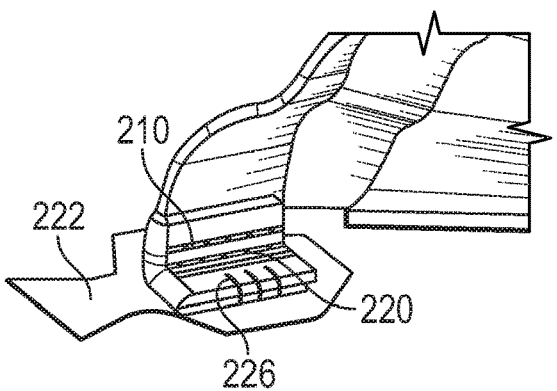

The first and second tab layers 206a, 206b can then be folded lengthwise along a vertical fold line as shown in FIG. 16 to form an outer folded portion 216 and an inner folded portion 218 that extends radially inwardly from the outer folded portion 216. A third vertically extending reinforcing member 220 can be placed against the first folded layer 206a of the outer folded portion 216 and a commissure attachment member 222 can be placed against the second folded layer 206b of the outer folded portion 216. The outer folded portion 216 can be secured to the commissure attachment member 222 with stitches 224 that extend through the third reinforcing member 220, the first and second tab layers 206a, 206b, and the commissure attachment member 222. The outer edges of the first and second tab layers 206a, 206b can be further secured to the commissure attachment member 222 with stitches 226. The upper tab 206 of a second leaflet 200 can be assembled in the same manner with respective reinforcing members and attached to the commissure attachment member 222 adjacent the first leaflet to form a commissure 228 as shown in FIG. 18. The commissure attachment member 222 can then be secured to the struts of the frame, as further described below.

The folded tab layers 206a, 206b, reinforced by the first and second reinforcing members 210, 212, can be more resistant to bending, or articulating, than the portions 230 of the leaflets that are radially inward of the tab layers. This causes the leaflets 200 to articulate primarily at inner edges 232 of the folded layers 206a in response to blood flowing through the prosthetic valve during operation of the prosthetic valve in the body, as opposed to articulating about respective axes on or adjacent the metal struts of the frame. Because the leaflets articulate at a location spaced radially inwardly from the frame 12, the leaflets can avoid contact with and damage from the frame. This is particularly advantageous in cases where the prosthetic valve is not fully expanded to its nominal size when implanted in a patient's body. As such, the prosthetic valve can be implanted in a wider range of patient annulus sizes.

Under high forces, the folded tab layers 206a, 206b of adjacent leaflets can splay apart from each other about respective axes 234 (FIG. 18) adjacent the frame 12, with each inner folded portion 218 folding out against the respective outer folded portion 216. For example, this can occur when the prosthetic valve 10 is compressed and mounted onto a shaft of a delivery apparatus, allowing for a smaller crimped diameter. The folded tab layers can also splay apart about their axes 234 when the balloon of the balloon catheter is inflated during expansion of the prosthetic valve, which can relieve some of the pressure on the commissures caused by the balloon and so the commissures are not damaged during expansion.

When the leaflets 200 are mounted to the frame, the lower tabs 204 of each leaflet can be folded downwardly against the cusp edge portion 202 and held in place, such as with sutures. The folded lower tabs 204 help reinforce the connection between the cusp edge portions 202 of the leaflets and the frame along the upper sections of the cusp edge portions adjacent the commissures. The folded lower tabs 204 also move the bending axes of the upper sections of the cusp edge portions inwardly and away from the inner surface of the frame to prevent or minimize contact between the leaflets and the frame in the areas below the commissures.

The side edges 238 between the lower and upper tabs 204, 206 can be left unattached to the frame of the prosthetic valve. The unattached side edges 238 provide several advantages, including reducing stress in the leaflets, by allowing greater elongation or stretching of the leaflets in the axial direction when the prosthetic valve is compressed from the radial expanded state to the radial compressed state during the crimping process and by allowing greater elongation or stretching of the leaflets in the radial direction when the prosthetic valve is expanded to its radial expanded state. The unattached side edges 238 also allow blood to flow in the space between a pair of side edges 238 of adjacent leaflets and the inner surface of the frame to reduce stagnant blood flow and thrombosis. During diastole, the adjacent side edges 238 can coapt with each other and prevent retrograde blood from flowing between the side edges 238. During systole, the adjacent side edges 238 can separate from each other and allow antegrade blood to flow between side edges 238 and help wash away blood from the areas underneath the commissures.

The reinforcing members 210, 212, 220 desirably comprise relatively soft and flexible, non-metallic materials. For example, the reinforcing members can comprise multifilament sutures (e.g., Ethibond sutures) or strips of synthetic material, such as fabric (e.g., PET) or non-fabric material (e.g., silicone or polyurethane), or natural tissue (e.g., pericardium). The commissure attachment member 222 similarly can comprise a soft and flexible, non-metallic material, such as strips of synthetic material, such as fabric (e.g., PET) or non-fabric material (e.g., silicone or polyurethane), or natural tissue (e.g., pericardium). Hence, in the illustrated embodiment, the commissure 228 does not include metallic components or other materials having similar rigidity. The absence of such materials can reduce abrasion and wear of the leaflet material and reduce the overall crimp profile of the prosthetic valve.

Figure 19:
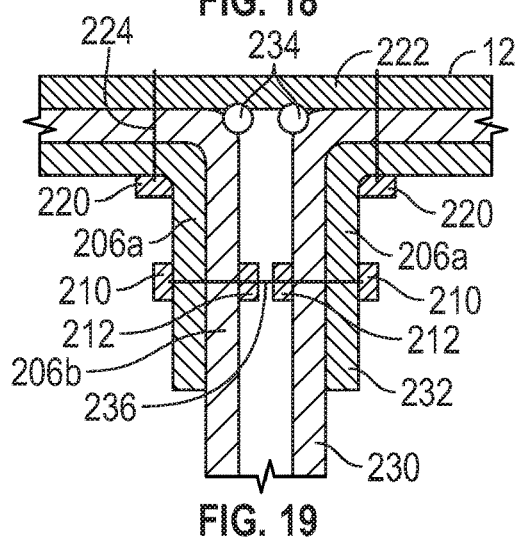
FIG. 19 is a cross-sectional view of a commissure formed from two leaflets of the type shown in FIG. 14, according to another embodiment.

FIG. 19 shows a modification of the embodiment shown in FIG. 18. The embodiment of FIG. 19 can be the same as that shown in FIG. 18 except that the pair of folded layers 206a, 206b of adjacent leaflets 200 can be secured to each other with a suture 236 that extends through the reinforcing members 210, 212 and the tab layers 206a, 206b of each leaflet 200. Securing the leaflets together can reinforce the bending axes of the articulating portions 230 of the leaflets during normal valve operation.

Figure 20:
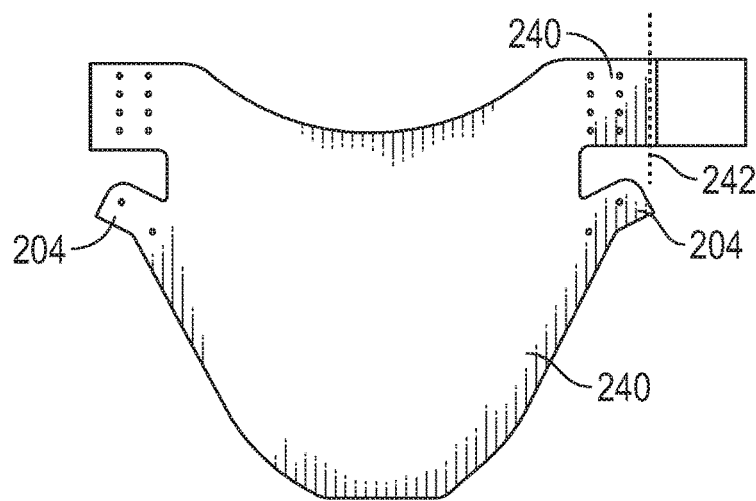
FIG. 20 is a plan view of a leaflet that can be used in a prosthetic heart valve, according to another embodiment.

FIG. 20 shows an alternative embodiment of a leaflet 240, which is similar to the leaflet 200, except that the leaflet 240 includes upper tabs 240 that project laterally a greater distance than the upper tabs 206. Each upper tab 240 can be folded widthwise along a respective vertical fold line 242 to form two folded tab layers that are paired with folded tab layers of an adjacent leaflet to form a commissure as previously described.

Figure 21:
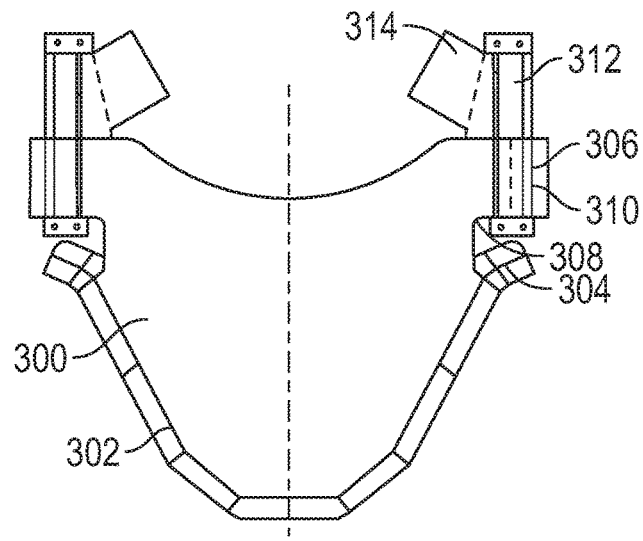
FIG. 21 is a plan view of a leaflet that can be used in a prosthetic heart valve, according to another embodiment.

FIGS. 21-27 show another embodiment of a leaflet and a method for forming a commissure from two leaflets. As shown in FIG. 21, a leaflet 300 comprises a lower edge portion 302 terminating at lower tabs 304, upper tabs 306 (also referred to as commissure tabs) spaced from the lower tabs 304 by gaps 308. The lower tabs 304 can be folded downwardly against the lower edge portion 302 to reinforce those areas of the leaflet and to move the bending axes of the upper sections of the edge portions 302 (the portions just below the commissures) inwardly away from the inner surface of the frame, as previously described.

Figure 22:
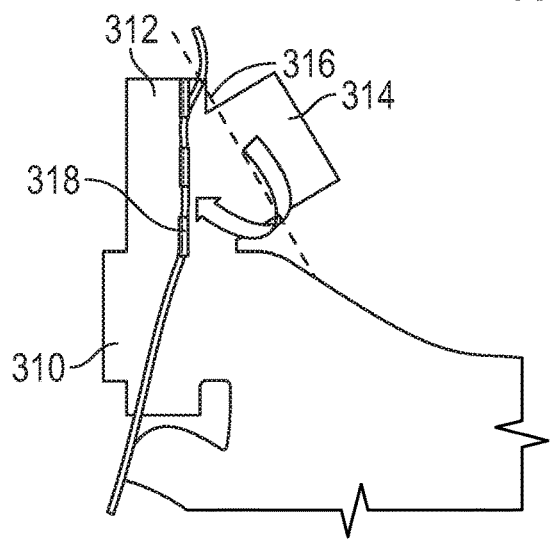
FIGS. 22, 23, 24, 25, and 26 show the formation of a commissure from two leaflets of the type shown in FIG. 21, according to one embodiment.
Figure 23:
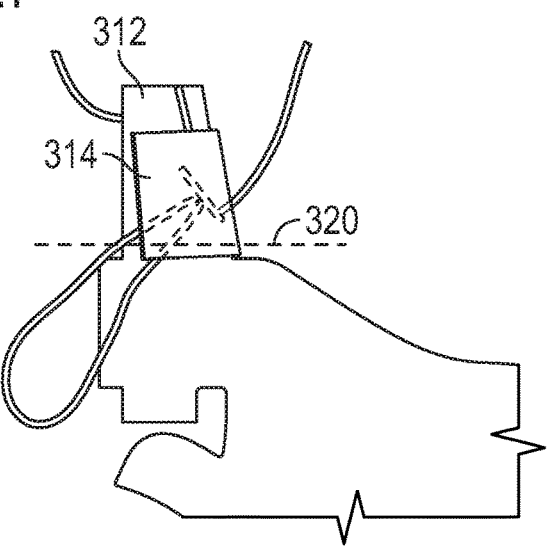
Figure 24:
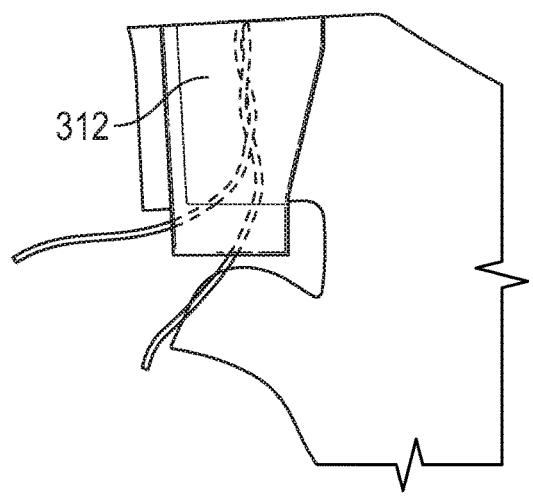

Each upper tab 306 includes a lower tab portion 310, an upper tab portion 312 extending from the lower tab portion, and a side tab portion 314 extending laterally inwardly from the upper tab portion. To form a commissure, a reinforcement member 318 (e.g., a multi-filament suture or a strip of fabric) can be placed vertically along the upper tab portion 312 in the manner shown in FIG. 22. The side tab portion 314 can then be folded along a fold line 316 against the upper tab portion 312 as shown in FIGS. 22-23. The dual layer of the side tab portion 314 and the upper tab portion 312 can then be folded along horizontal fold line 320 against the lower tab portion 310, as depicted in FIGS. 23-24.

Figure 25:
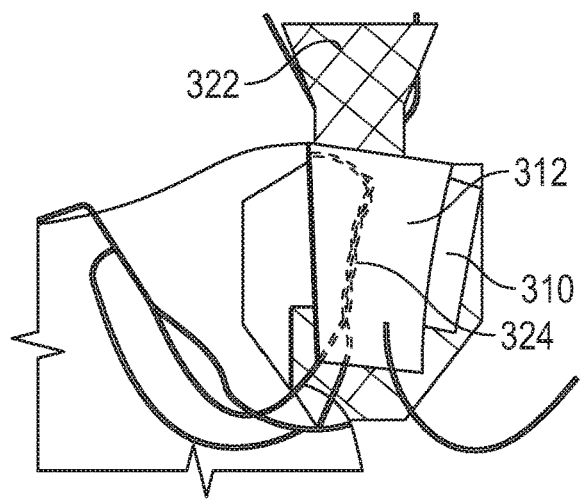
Figure 26:
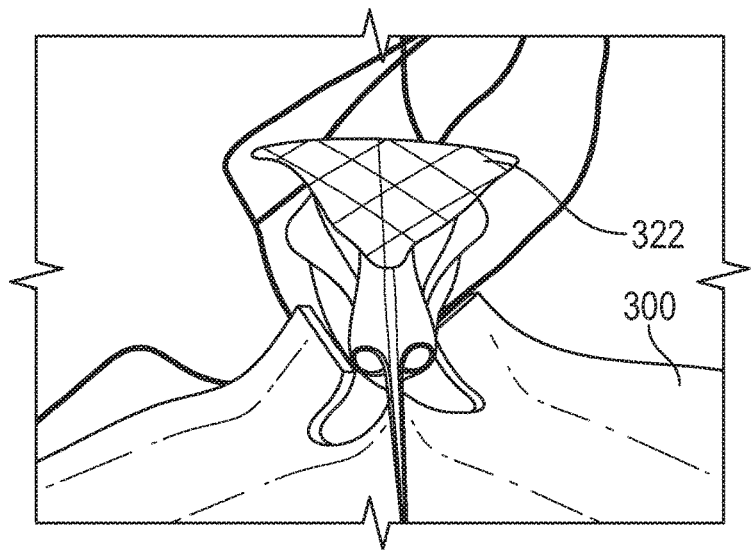
Figure 27:
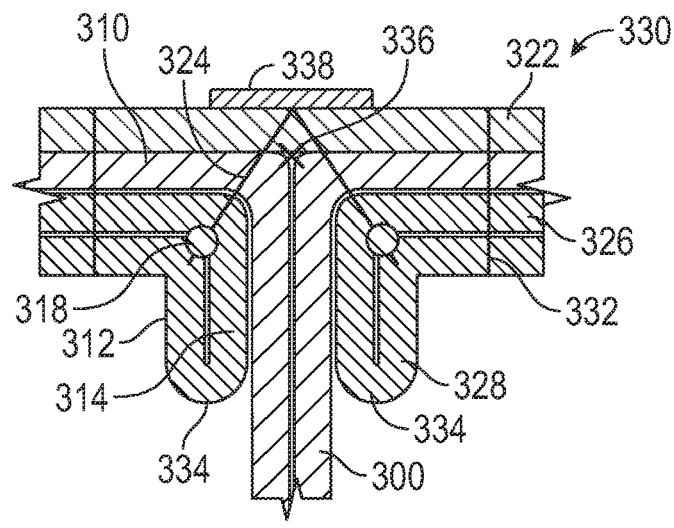
FIG. 27 is a cross-sectional view of a commissure formed from two leaflets of the type shown in FIG. 21, according to one embodiment.

As shown in FIG. 25, a commissure attachment member 322 can then be placed against the rear (outer) surface of the lower tab portion 310 and secured to the upper tab 306 with stitching 324 that extends through the upper tab portion 312, reinforcement member 318, the side tab portion 314, the lower tab portion 310, and the commissure attachment member 322. The three layers formed by the lower tab portion 310, the upper tab portion 314, and the side tab portion 314 can then folded into an L-shape to form an outer folded portion 326 adjacent the commissure attachment member 322 and an inner folded portion 328 extending radially inwardly from the outer folded portion as shown in FIG. 27. As shown in FIG. 27, the tab layers of the outer folded portion 326 can be further secured to the commissure attachment member 322 with stitches 332. The upper tab 306 of another leaflet can be assembled in the same manner and secured to the same commissure attachment member 322 to form a commissure 330 as shown in FIGS. 26-27.

As described above, the stitches 324 can extend through each layer formed by the lower tab portion 310, the upper tab portion 314, and the side tab portion 314. As shown in FIG. 27, the stitches 324 from each commissure tab 306 can extend diagonally toward each other to compress the folded commissure tabs 306 against each other and the commissure attachment member 322. In alternative embodiments, the stitches 324 can be placed through the reinforcement member 318, the side tab portion 314 and the lower tab portion 310 prior to folding the upper tab portion and the side tab portion along fold line 320. In this manner, the stitches 324 need not extend through the upper tab portion 312, as depicted in FIG. 27. In some embodiments, another reinforcement member 438 can be placed against the outer surface of the commissure reinforcement member 322 (FIG. 27). The stitches 324 from each commissure tab 306 can extend through the reinforcement member 338 at the same location as shown or at spaced apart locations.

The commissure 330 can function similar to the commissure 228 described above. Thus, during normal valve cycling, the leaflets 300 can articulate about respective axes at the inner ends 334 of the tab layers 312. The compression of the folded commissure tabs 306 by stitches 324 helps maintain the normal bending axes of the leaflets 300 away from the frame. During valve deployment, the leaflets can splay apart from each other at an axis 336 adjacent the commissure attachment member 322.

Figure 28:
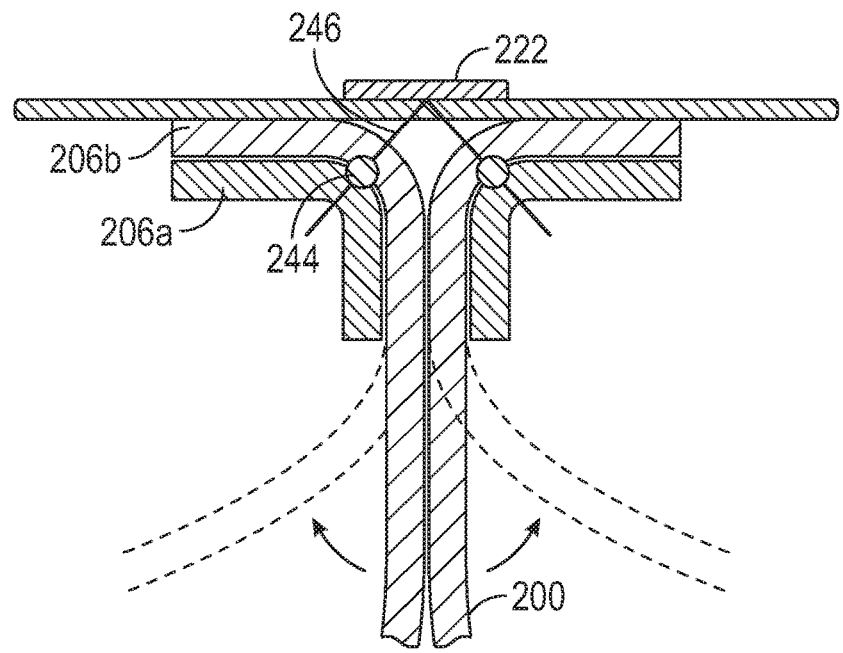
FIG. 28 is a cross-sectional view of a commissure formed from two leaflets of the type shown in FIG. 14, according to another embodiment.

FIG. 28 shows an alternative configuration for forming a commissure. The embodiment of FIG. 28 is similar to the embodiment of FIGS. 14-18 except that a vertical reinforcement member 244 can be placed between two layers of the commissure tab of the leaflet. The commissure can be formed by placing the reinforcement member 244 on tab portion 206a prior to folding tab portion 206a along fold line 208. After folding the commissure tab 206, the folded layers 206a, 206b can be secured to the commissure attachment member 222 with stitches 246 that extend through the reinforcement member 244, both tab layers 206a, 206b, and the commissure attachment member 222.

Figure 29:
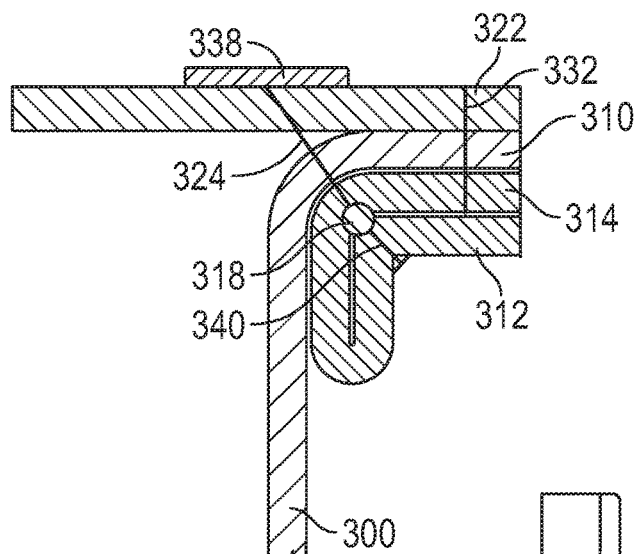
FIG. 29 is a cross-sectional view of a commissure formed from two leaflets of the type shown in FIG. 21, according to another embodiment.

FIG. 29 shows an alternative configuration for forming a commissure similar to FIG. 27, except that each folded commissure tab 306 is secured to a separate reinforcing member 338 (one of which is shown in FIG. 29). Also, stitches 340 can secure the side tab portion 312 to the reinforcing member 318.

Figure 30:
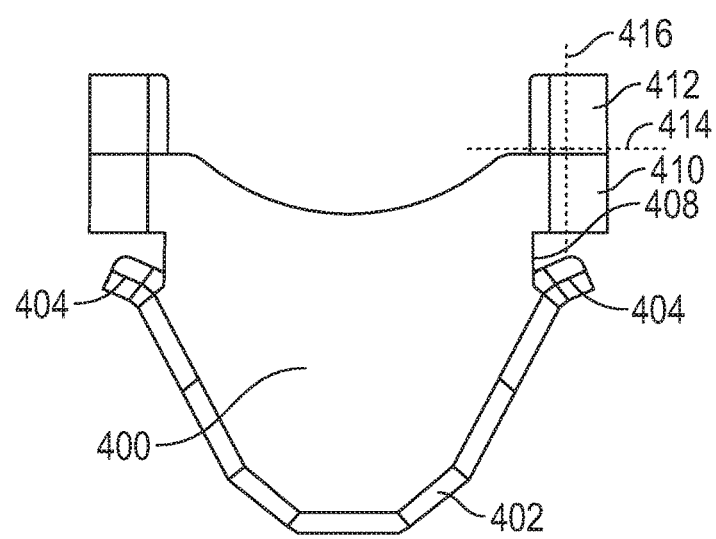
FIG. 30 is a plan view of a leaflet that can be used in a prosthetic heart valve, according to another embodiment.

FIGS. 30-35 show another embodiment of a leaflet and a method for forming a commissure 32 from two leaflets. As shown in FIG. 30, a leaflet 400 comprises a lower edge portion 402 terminating at lower tabs 404, upper tabs 406 (also referred to as commissure tabs) spaced from the lower tabs 404 by gaps 408. The lower tabs 404 can be folded downwardly against the lower edge portion 402 to reinforce those areas of the leaflet and to move the bending axes of the upper sections of the edge portions 402 (the portions just below the commissures) inwardly away from the inner surface of the frame, as previously described.

Figure 31:
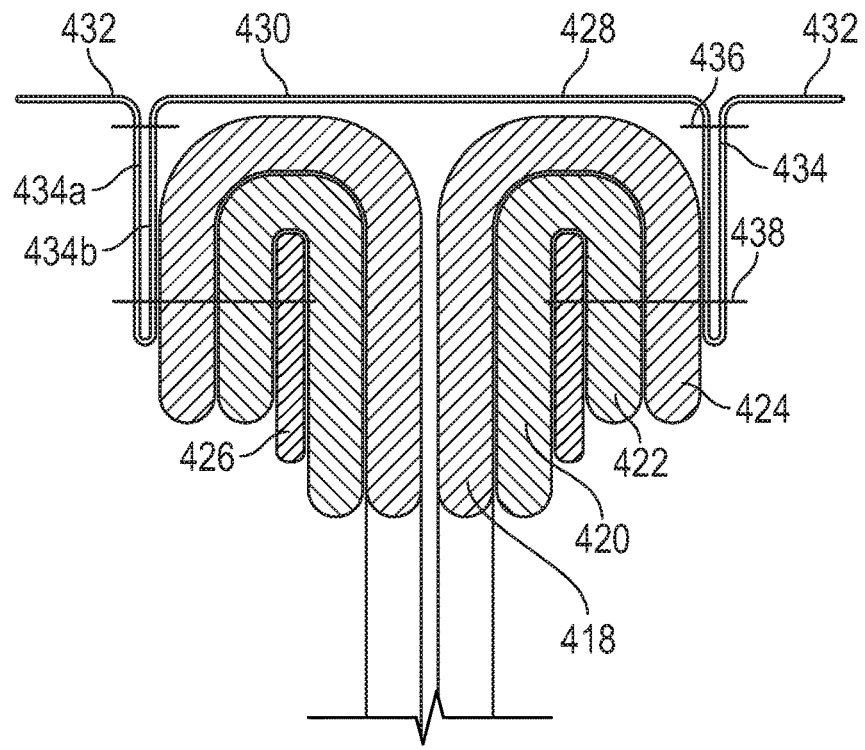
FIGS. 31-32 are cross-sectional views of two embodiments of a commissure formed from two leaflets of the type shown in FIG. 30.
Figure 32:
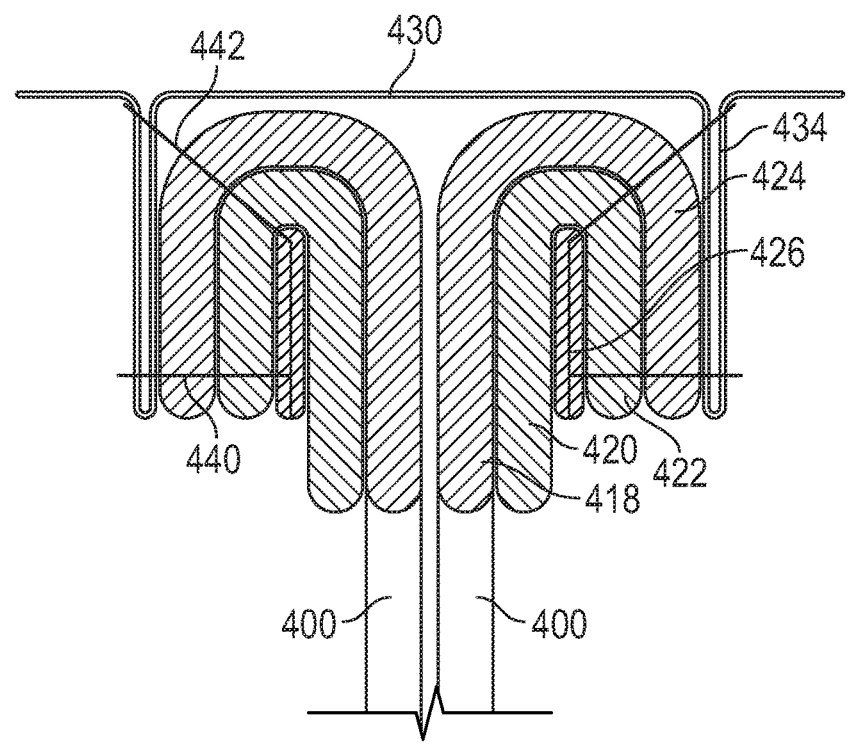
Figure 33:
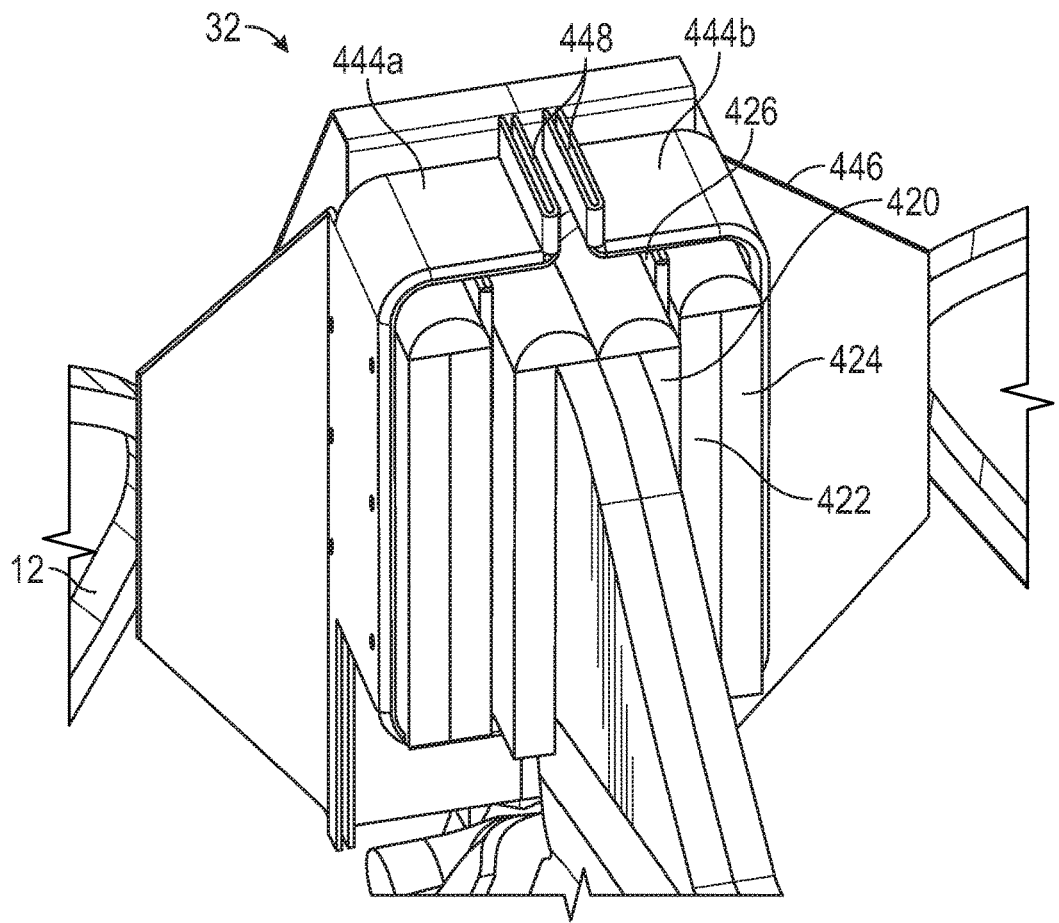
FIGS. 33, 34, 35, and 36 are various views showing the attachment of the commissure of FIG. 31 or 32 to the frame of a prosthetic heart valve using a commissure attachment member.

Each commissure tab 406 includes a lower tab portion 410 and an upper tab portion 412. To form a commissure, the upper tab portion 412 is folded along fold line 414 against the lower tab portion 410. The dual layer comprising tab portions 410, 412 can then be folded along a vertical fold line 416 to form a first layer 418, a second layer 420, a third layer 422, and a fourth layer 424 from each commissure tab 406, as depicted in FIGS. 31-33. A reinforcement member 426, such as strip of fabric (e.g., PET), can be positioned between the second layer 420 and the third layer 422.

The commissure tab 406 of another leaflet 400 is folded in the same manner and placed against the folded commissure tab of the first leaflet within a commissure attachment member 428. The commissure attachment member 428 can be folded as shown in FIG. 31 to form a central outer portion 430, outer end portions 432, and side portions 434, each comprising first and second layers 434a, 434b of material extending from respective ends of an end portion 432 and the central outer portion 430. The side portions 434 can be placed against respective fourth layers 424 of the commissure tabs.

As shown in FIG. 31, the layers 434a, 434b of each side portion 434 can be secured to each other with stitching 436. Each side portion 434 can be secured to a commissure tab 406 with stitching 438 extending through a respective reinforcing member 426, respective third and fourth layers 422, 424, and both layers of a respective side portion 434. The commissure attachment member 428 can be secured to the struts 22 of a frame 12 with sutures or other techniques or mechanisms.

FIG. 32 shows another way of securing the folded commissure tabs 406 to the commissure attachment member 430. As shown in FIG. 32, for each commissure tab, a row of laterally extending stitches 440 can be used to secure the inner end portions of the layers 434a, 434b of the side portion, the third and fourth layers 422, 424, and the reinforcing member 426. A diagonally extending row of stitches 442 can be used to secure the reinforcing member 426, the third and fourth layers 422, 424, and the rear end portions of layers 434a, 434b of the side portion.

Figure 34:
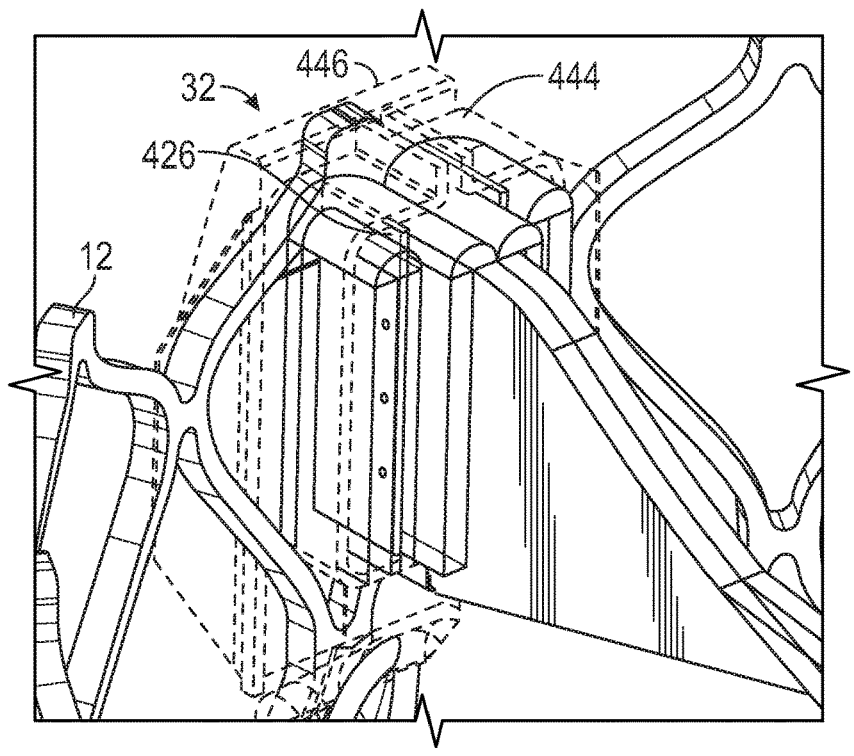

As shown in FIGS. 33-34, each commissure 32 can include an inner sleeve 444 and an outer support member 446. The inner sleeve 444 can comprise first and second portions 444a, 444b, each of which extends around the outer side as well as the upper and lower portions of a respective folded commissure tab 406. The adjacent upper ends 448 of the first and second portions 444a, 444b can be secured to each other (e.g., with sutures) at the center of the commissure 32. The adjacent lower ends of the first and second portions 444a, 444b can be secured to each other (e.g., with sutures) in a similar manner at the center of the commissure 32. Each of the side portions 434 of the commissure attachment member 428 can be secured to one of the first and second portions 444a, 444b of the inner sleeve (e.g., with sutures). The outer support member 446 can be secured to the central outer portion 430 and/or the end portions 432 of the commissure attachment member 428 (e.g., with sutures).

Figure 35:
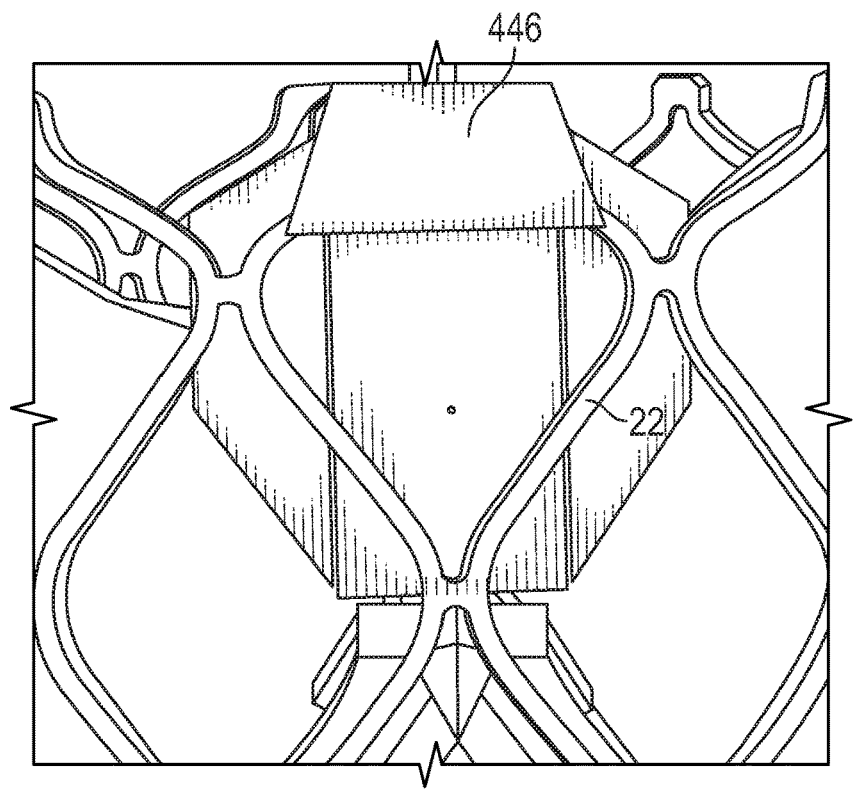

As shown in FIG. 35, at least a portion of the outer support member 446 can be positioned outside of the frame 12. The outer support member 446 can be secured (e.g., with sutures)

to each strut 22 of a set of struts forming a cell of the frame. In the illustrated embodiment, for example, the outer support member 446 can be sutured to each strut of a diamond-shaped cell comprised of four struts 22. The inner sleeve 444 and the outer support member 446 can comprise any suitable relatively flexible and soft material. For example, the outer support member 446 and the inner sleeve 444 can comprise natural or synthetic fabric materials, non-fabric polymeric materials (e.g., silicone or polyurethane), or natural tissue (e.g., pericardium) In particular embodiments, the inner sleeve 444 and the outer support member 446 comprise PET fabric.

Figure 36:
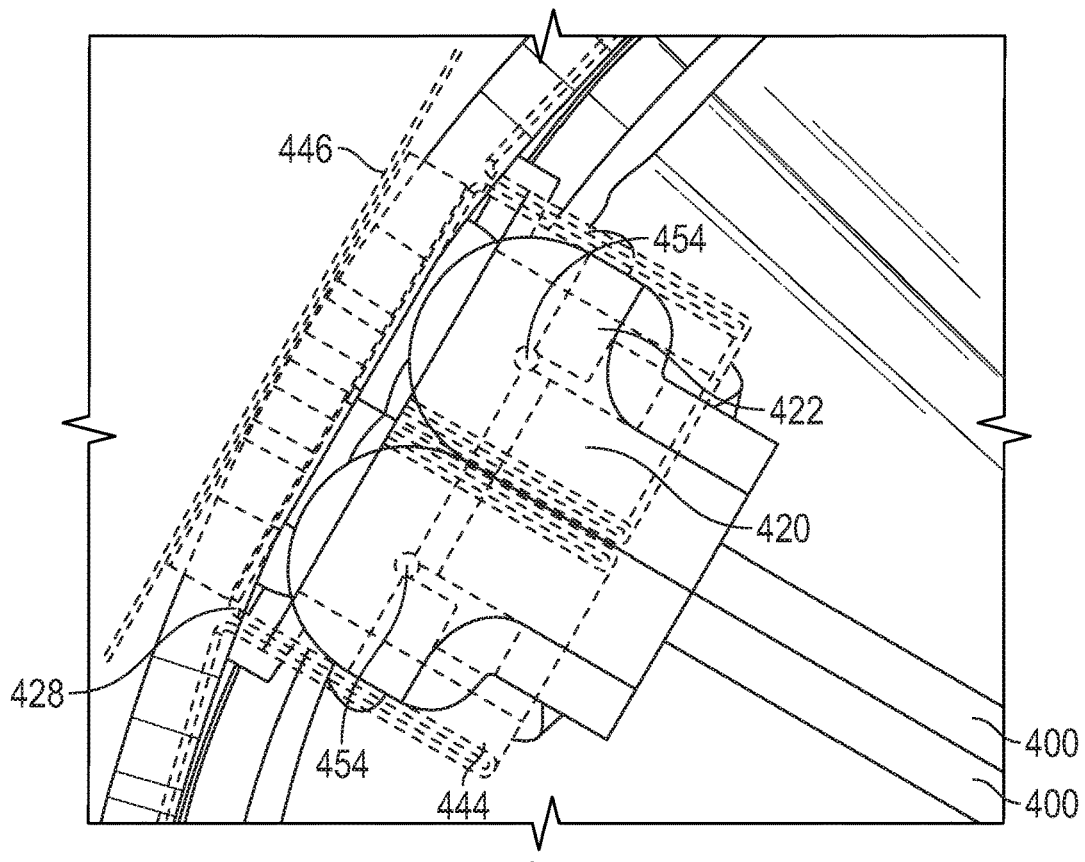

FIG. 36 shows a modification of the commissure 32 shown in FIGS. 33-35. The embodiment of FIG. 36 can be the same as the embodiment of FIGS. 33-35, except that the former includes reinforcing members 454 in the form of multi-filament sutures positioned between the second and third layers 420, 422 of each commissure tab 406. Additional systems and methods for attaching leaflets to a frame can be found in U.S. patent application Ser. No. 15/664,430 filed on Jul. 31, 2017, which is incorporated herein by reference.

Figure 37:
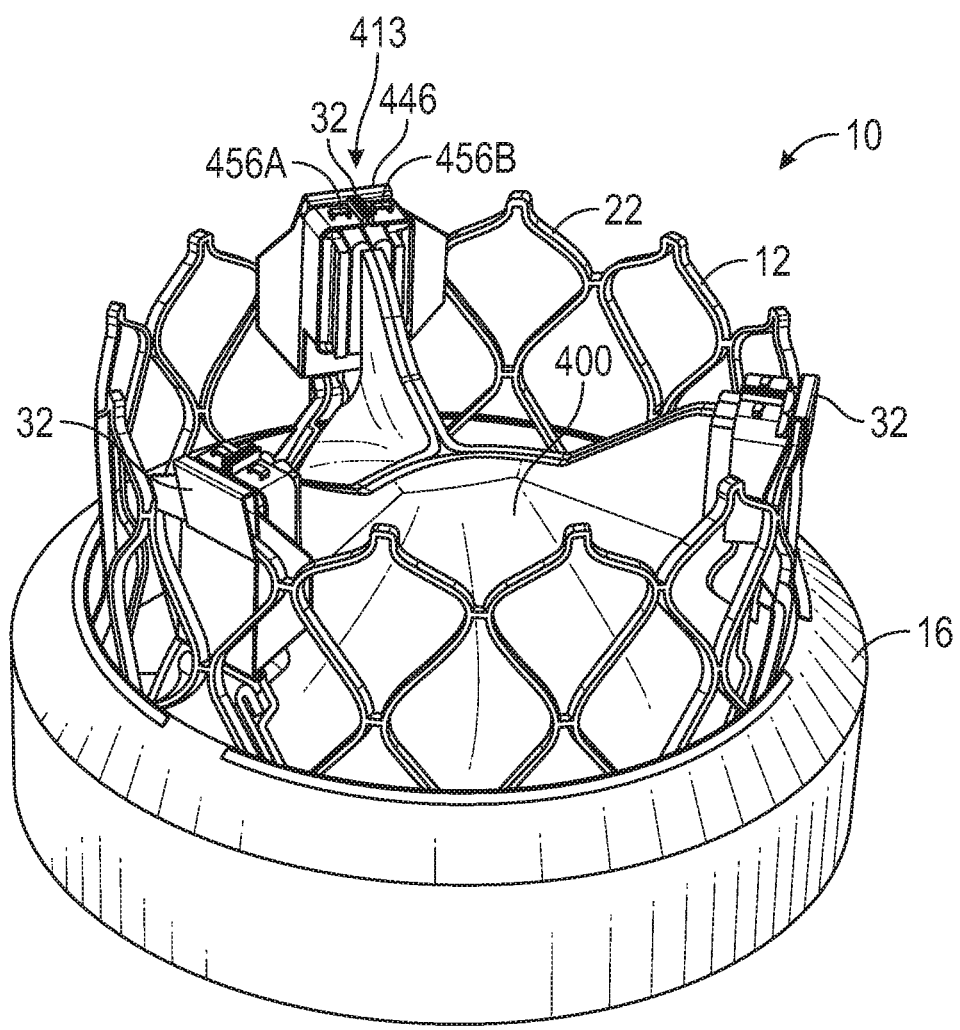
FIG. 37 is a perspective view of another embodiment of a prosthetic heart valve.
Figure 38A:
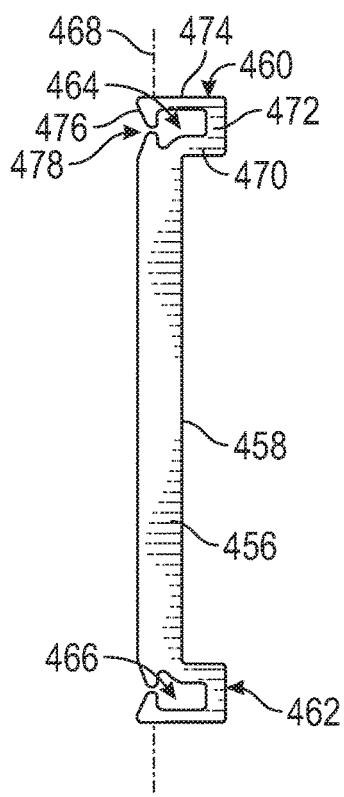
FIG. 38A is a plan view of a reinforcing member.

FIGS. 37-58 illustrate another modification of the commissure 32 shown in FIGS. 33-35. Each of the commissures can include a commissure support element or assembly 413 comprising a pair of reinforcing members 456 that are detached, separate, or not connected to the frame, and spaced radially inward from the frame. In the illustrated embodiment, the reinforcing members 456 can be situated between, for example, the second and third layers 420, 422 of the upper commissure tabs 406 of adjacent leaflets. A representative example of a reinforcing member 456 is shown in FIG. 38A. The reinforcing member 456 can include a main body portion 458 having a longitudinal axis 468, and first and second end portions configured as attachment portions 460, 462. In the embodiment of FIG. 38A, the attachment portions 460, 462 can be curved or hooked such that they define respective suture receiving portions 464, 466, and such that the reinforcing member 456 has a C-shaped profile that depends upon the lateral dimensions of the suture receiving portions 464 and 466. For example, the first attachment portion 460 can be defined by a first portion 470 of the reinforcing member 456 extending away from the main body portion 458 and perpendicular to the longitudinal axis 468, a second portion 472 extending parallel to the longitudinal axis 468 and offset from the main body portion 458, and a third portion 474 extending toward the main body portion 458 and perpendicular to the longitudinal axis 468. An end portion 476 of the third portion 474 can be spaced apart from the main body portion 458 by a gap or opening 478. In this manner, a connecting member, such as a yarn or suture thread, can be inserted into the suture-receiving portion 464 through the gap 478, as further described below. In the illustrated embodiment, the second attachment portion 462 has a configuration similar to the first attachment portion 460, although the first and second attachment portions 460, 462 may be configured the same or differently, as desired.

Figure 38B:
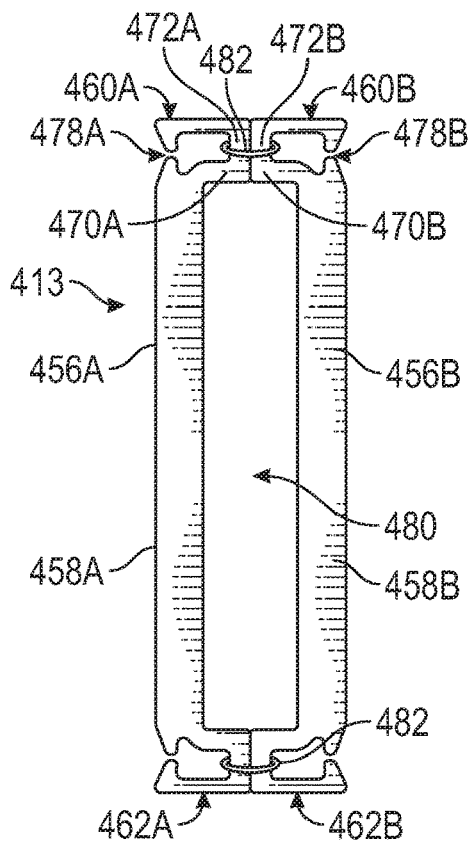
FIG. 38B is a plan view of a commissure support element including a commissure window that can be formed using two of the reinforcing members of FIG. 38A.

Referring to FIG. 38B, a commissure support element or support structure 413 can be formed by situating two reinforcement members 456A, 456B such that the second portions 472A, 472B of the respective attachment portions 460A, 460B are adjacent one another, and the respective gaps 478A, 478B face away from each other. The attachment portions 462A, 462B can be arranged in a similar configuration. In this manner, the pair of reinforcement members 456A, 456B can define a commissure window 480 that is at least partially bounded by the main body portions 458A, 458B and the first portions 470A, 470B of the respective attachment portions of each reinforcement member. The reinforcement members 456A, 456B can be tied or otherwise secured together by, for example, suture 482 extending through the respective attachment portions 460A, 460B and 462A, 462B of each reinforcement member.

Figure 39:
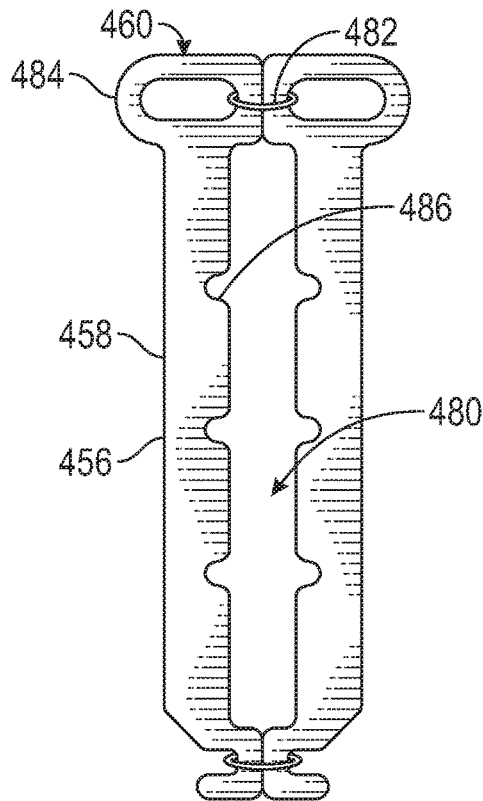
FIGS. 39 and 40 are plan views illustrating alternative embodiments of reinforcing members.
Figure 40:
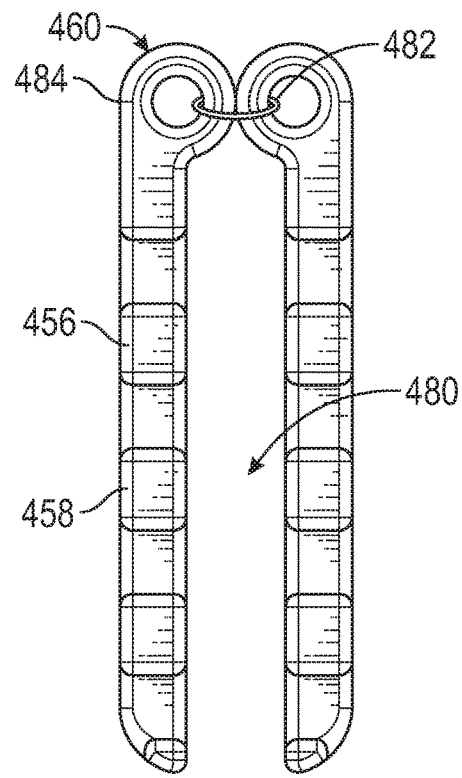

FIGS. 39 and 40 illustrate alternative embodiments of commissure support elements or structures using other configurations of reinforcing members. For example, one or more of the attachment portions 460, 462 can be configured as eyelets 484, as shown in FIGS. 39 and 40. Additionally, as shown in FIG. 39, the reinforcement members 456 can define grooves 486 (e.g., in the main body portion 458). The grooves 486 can be defined on the surface of the main body portion 458 that is oriented toward the interior of the commissure window 480, on the surface oriented away from the commissure window, or both, as desired. In certain embodiments, the grooves 486 can aid in securing or clamping the leaflets between the members 456, or can provide a location of additional suture attachment. Additionally, in some embodiments, the reinforcement members 456 need only include one attachment portion, such as at the attachment portion 460 of the embodiment of FIG. 40, such that the commissure window 480 is open on the end opposite the attachment portions 460. The reinforcement members 456 can be formed from any of various metals such as nitinol, stainless steel, cobalt chromium, etc., or polymeric materials such as any of various plastics. Moreover, although the reinforcement members 456A and 456B are shown contacting each other in FIGS. 38B, 39, and 40, in use the reinforcement members may be spaced apart from each other by portions of the valve leaflets to which the reinforcement members are attached, as further described below.

FIGS. 41-53 illustrate a representative method of forming a commissure 32 using the reinforcement members 456 of FIGS. 38A and 38B. The leaflet 400 can have a first side surface 488 and a second side surface 490 (see, e.g., FIG. 44). The upper tab 406 is folded over in FIG. 44 such that the second side surface 490 is visible. In embodiments where the leaflets 400 comprise natural tissues (e.g., bovine tissue), the first side surface 488 can correspond to the ventricular side of the leaflet, and can be relatively smooth. The second side surface 490 can correspond to the arterial side of the leaflet, and can comprise, for example, a plurality of ridges or other textures or features.

Figure 41:
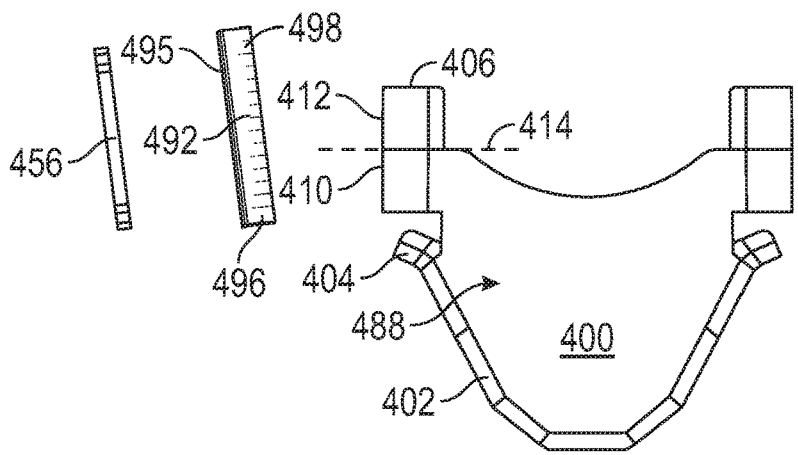
FIG. 41 is a plan view of another embodiment of a leaflet that can be used in a prosthetic heart valve, along with a reinforcing member of FIG. 38A and an attachment member.
Figure 42:
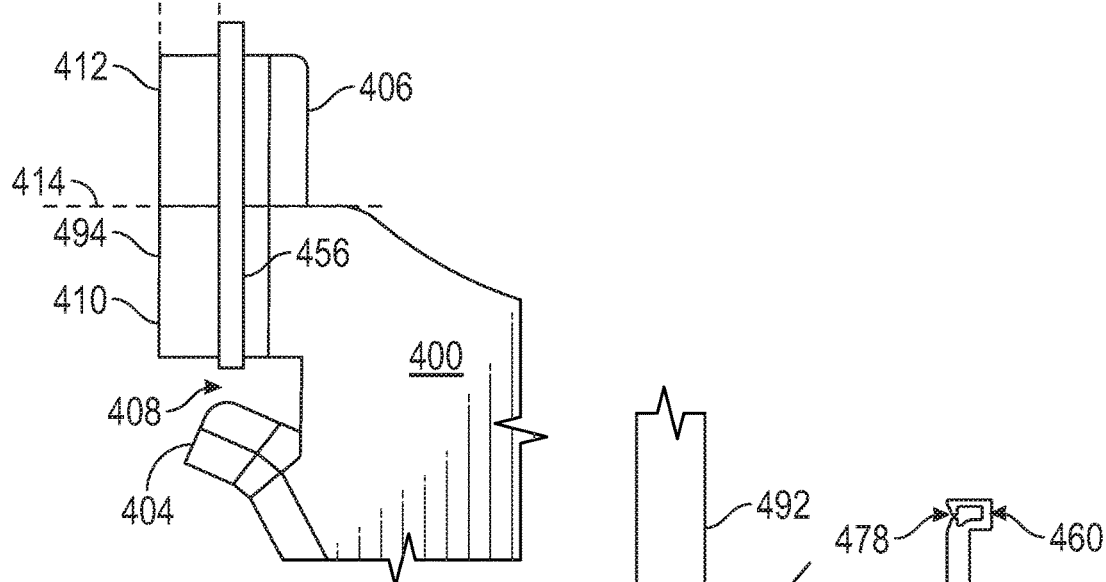

Referring to FIGS. 41 and 42, the upper tab portion 412 of the upper tab 406 can be folded down along line 414 in the direction of the first side surface 488. A reinforcement member 456 can then be attached (e.g., by suturing) to the exposed second side surface 490A of the upper tab 406, and an attachment member 492 can be attached (e.g., by suturing) to the second side surface 490B (see FIGS. 44 and 45) of the lower tab portion 410.

Referring to FIG. 42, the reinforcement member 456 can be attached to the upper tab 406 at a distance $D_1$ from the outer edge 494 of the upper tab. In a representative embodiment, the distance $D_1$ can be about 2 mm, although the distance $D_1$ can be any suitable distance depending upon, for example, the width of the upper tab 406. The reinforcement member 456 can be positioned such that the first and second attachment portions 460, 462 extend beyond the upper and lower edges of the folded commissure tab 406, as shown in FIG. 44. The reinforcement member 456 can also be situated such that the gaps 478 of the respective first and second attachment portions 460, 462 are oriented in a direction toward the attachment member 492, as best shown in FIG. 46.

Figure 47:
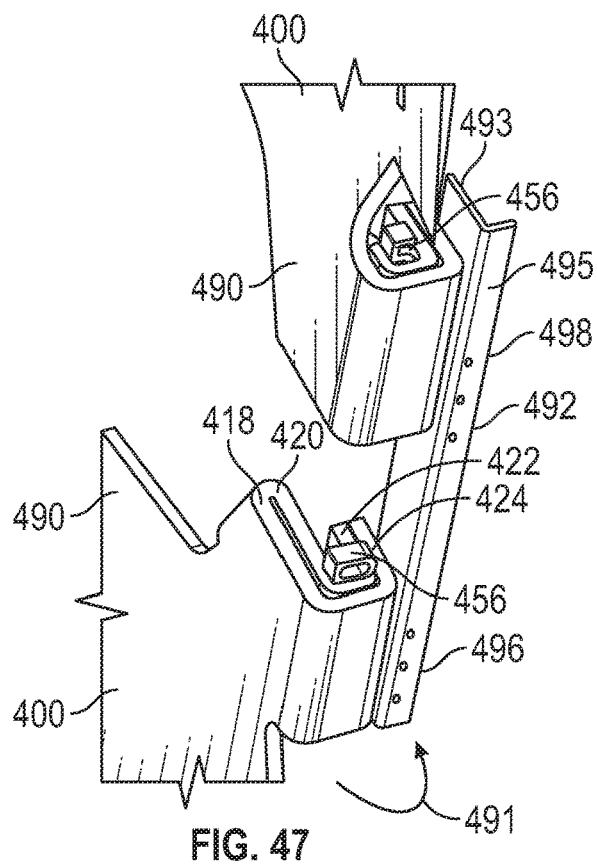

Referring to FIGS. 43-47, the attachment member 492 can be configured as a strip of material, and can have a first end portion 496 and a second end portion 498. In the illustrated embodiment, the attachment member 492 can also have an L-shaped profile, with a first body portion 493 and a second body portion 495 that extends from one edge of the first body portion 493 and is oriented perpendicular to the first body portion, as best shown in FIG. 47. The attachment member 492 can be formed from any of various flexible and/or deformable materials, including shape-memory metal alloys such as nitinol, plastically-deformable alloys such as stainless steel, cobalt chromium, etc., polymeric materials such as any of various plastic or rubber compounds, strips of synthetic material such as fabric (e.g., PET) or non-fabric material (e.g., silicone or polyurethane), or natural tissue (e.g., pericardium).

Figure 43:
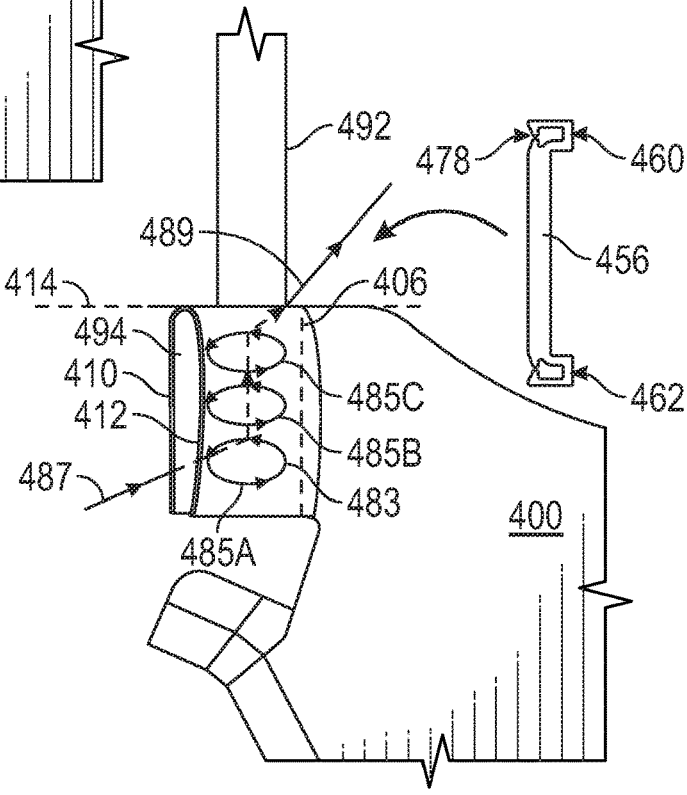

Referring to FIGS. 43-46, the first end portion 496 of the attachment member 492 can be secured to the lower tab portion 410 such that the first body portion 493 is adjacent the commissure tab 406 and the second body portion 495 extends away from the commissure tab, as shown in FIGS. 45 and 46. In some embodiments, an edge 481 of the first body portion 493 of the attachment member 492 can be aligned with the outer edge 494 of the upper tab 406, as shown in FIGS. 44-46. However, in other embodiments the edge 481 can be offset from the edge 494 of the upper tab 406, as shown in FIG. 43.

As stated above, the reinforcement member 456 and the attachment member 492 can be secured to the upper tab 406 by suturing. In the illustrated example, suture 483 can be passed through the attachment member 492 (e.g., through the first body portion 493), through the upper and lower tab portions 410, 412, and looped around the reinforcement member 456 before passing back through the tab portions 410, 412 and the attachment member 492 to form suture loops 485. This process can be repeated along the length of the main body portion 458 of the reinforcement member 456. For example, in the illustrated embodiment the reinforcement member 456 and the attachment member 492 are secured to the upper tab 406 by three suture loops 485A-485C, although greater or fewer suture loops may be employed. In the illustrated embodiment, the loops 485A-485C can be stitched such that a first length of suture or "suture tail" 487 can extend from the first end portion 496 of the attachment member 492 adjacent the first suture loop 485A, and a second length of suture or "suture tail" 489 can extend from the first end portion of the attachment member 492 adjacent the third suture loop 485C, as shown in FIG. 43.

Figure 48:
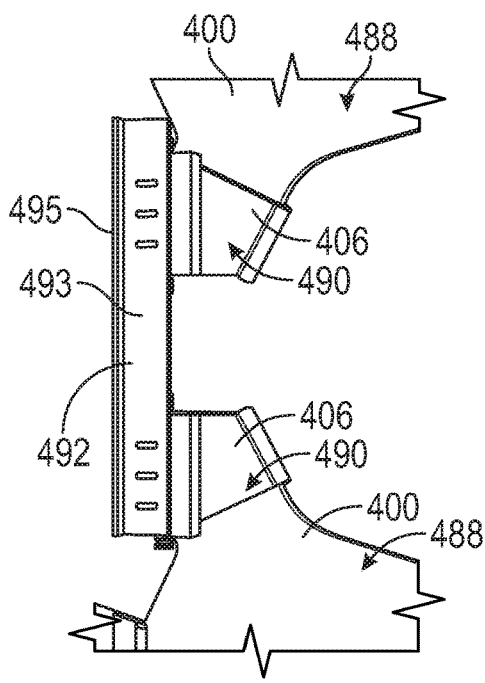
Figure 49:
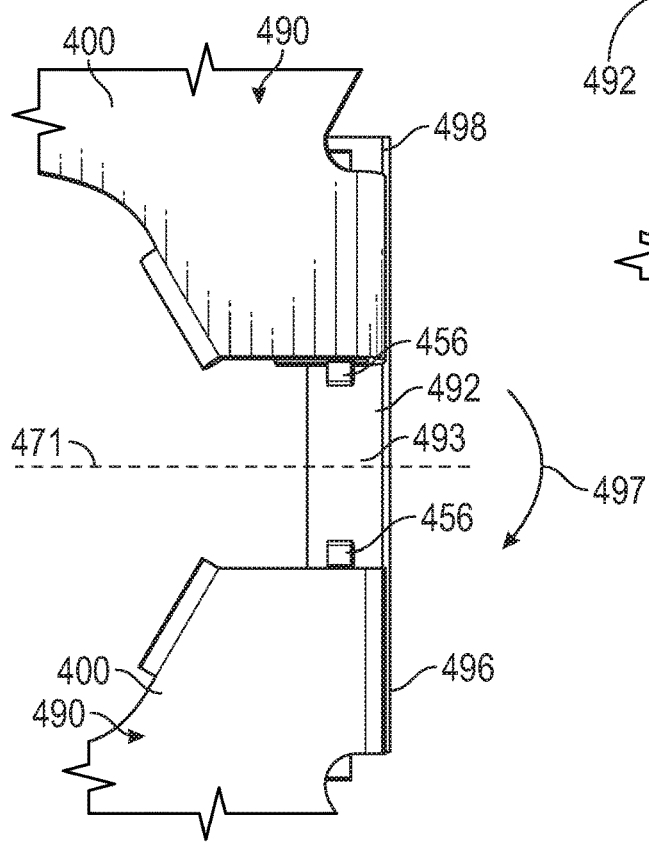

Referring to FIGS. 47-49, the second end portion 498 of the attachment member 492 can be secured to a commissure tab of another leaflet 400 along with another reinforcement member 456 in the manner described above. With the two leaflets 400 laid side-by-side, the commissure tabs 406 can be folded around the reinforcement members 456 in the manner of arrow 491 in a direction toward the first surface 488 to form first, second, third, and fourth layers 418, 420, 422, 424, similar to those described above with respect to FIG. 31. This folding action locates the reinforcement members 456 between the second and third layers 420, 422, and orients the attachment member 492 such that the first body portion 493 is parallel to the first surfaces 488 of the leaflets, and the second body portion 495 is perpendicular to the first surfaces of the leaflets, as best shown in FIGS. 47 and 48.

FIG. 48 is a top plan view showing the assembly as viewed from the side of the first surfaces 488 of the leaflets, and FIG. 49 is a bottom plan view illustrating the assembly as viewed from the side of the second surfaces 490 of the leaflets.

Figure 50:
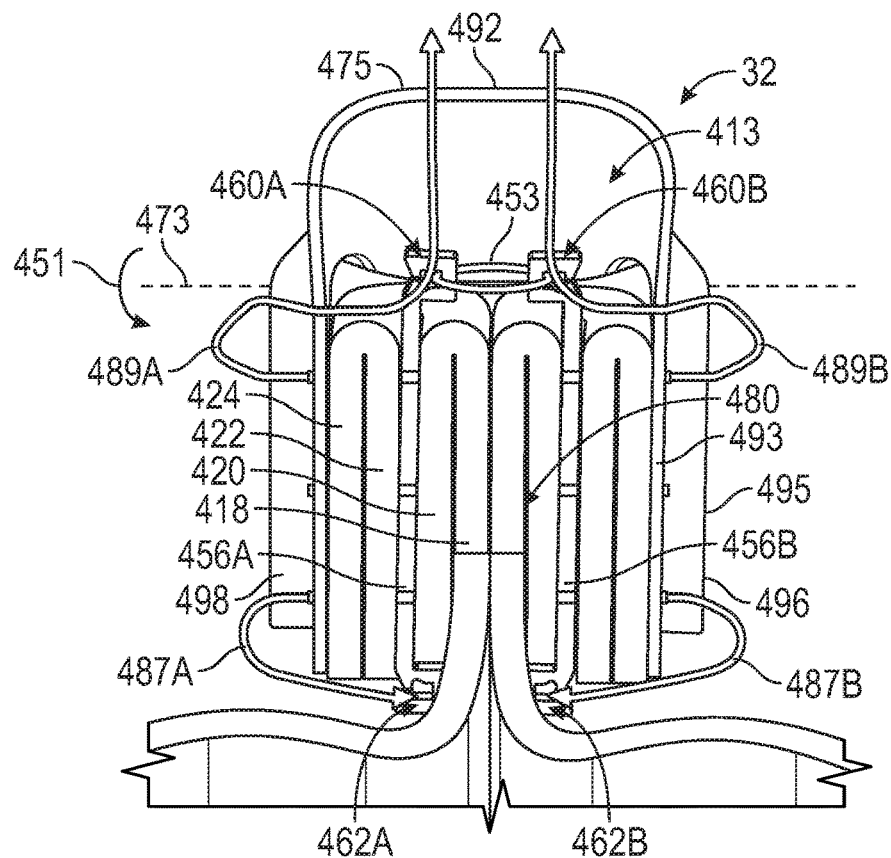
FIG. 50 is a cross-sectional view of a commissure formed from two leaflets of the type shown in FIG. 41 using the reinforcing member of FIG. 38A.
Figure 51:
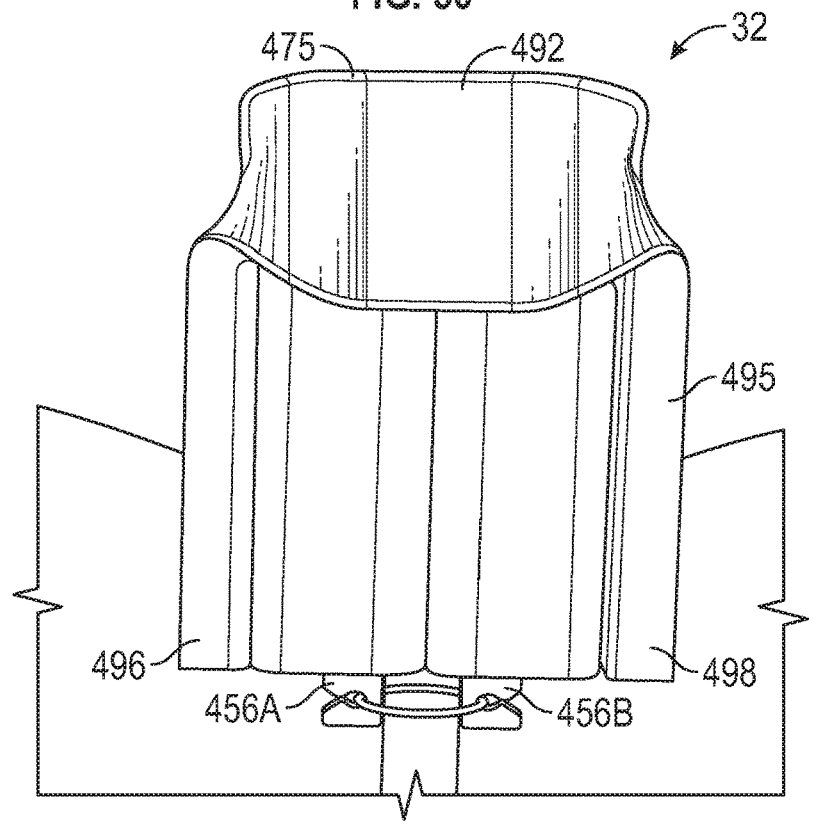
FIG. 51 is a rear perspective view of the commissure of FIG. 50.

Referring to FIG. 49, the leaflets 400 can then be folded together about fold line or axis 471 in the manner indicated by arrow 497 such that the second surfaces 490 of the leaflets are folded toward one another to form a commissure 32. Referring to FIGS. 50 and 51, the first and second end portions 496, 498 of the attachment member 492 can then be bent or folded about fold line 473 in the direction of arrow 451 such that the first and second end portions 496, 498 extend downwardly from a mid-portion 475 of the attachment member 492 and are substantially parallel to the reinforcement members 456A, 456B and to each other.

Figure 57:
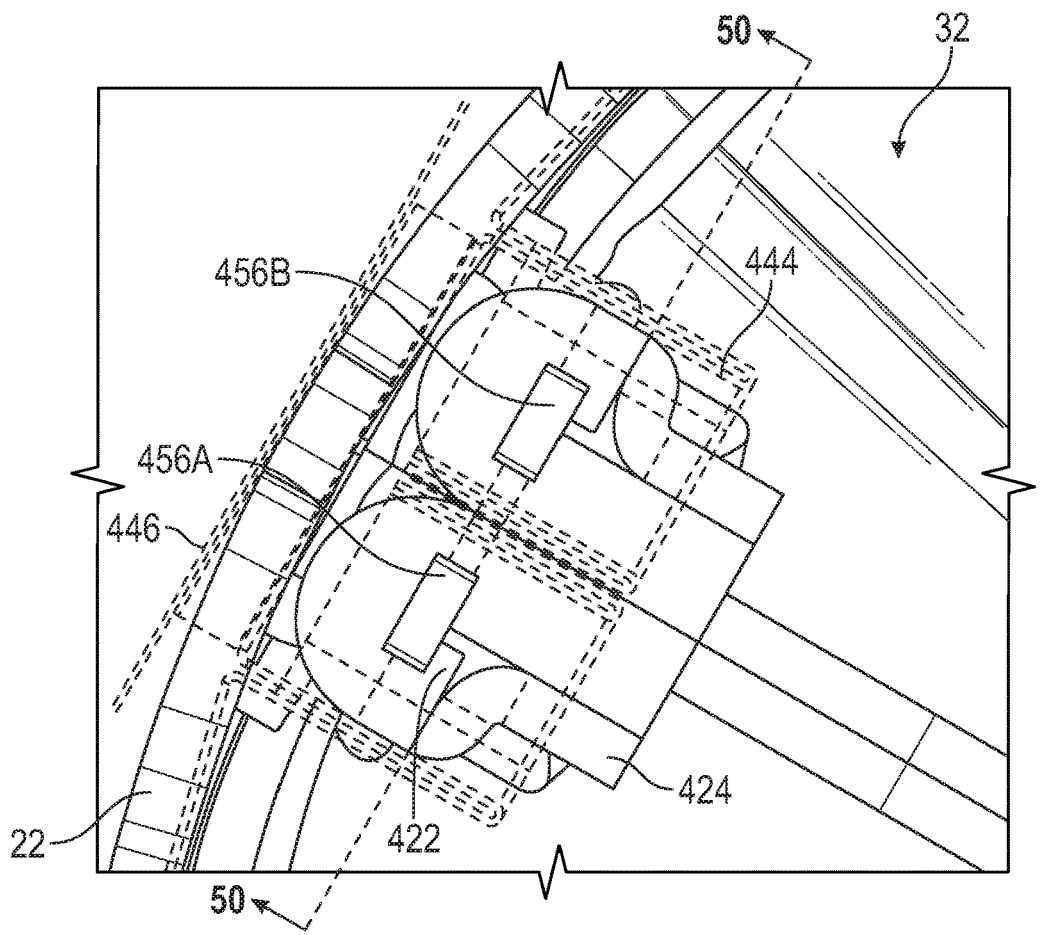

FIG. 50 is a partial cross-sectional view taken along line 50-50 of FIG. 57. As shown in FIG. 50, the respective suture tails 489A, 489B can be inserted through the first body portion 493 of the attachment member 492 on their respective sides of the commissure. The suture tails 489A, 489B can then be looped through the suture-receiving portions of the respective attachment portions 460A, 460B of the reinforcement members 456A, 456B. For example, the suture tails 489A, 489B can be wrapped around the attachment portions 460A, 460B (e.g., two times, three times, etc.) such that the suture tails form suture loops 453 extending between the reinforcement members 456A, 456B. The suture tails 489A, 489B can then be tied together (e.g., in a double square knot) to secure the attachment portions 460A, 460B together. The suture tails 487A, 487B can be wrapped around the attachment portions 462A, 462B and tied together in a similar manner (see, e.g., FIG. 51) to form the commissure window 480 of the support element 413. In some embodiments, the remaining length of the suture tails 489A, 489B can be used to secure the assembly to the struts of the frame. In alternative embodiments, the reinforcement members can be secured together by wrapping the suture tail 489A around the attachment portion 460A of the reinforcement member 456A one or more times, wrapping the suture tail 489B around the attachment portion 460B of the reinforcement member 456B one or more times, and then tying the suture tails together.

Figure 53:
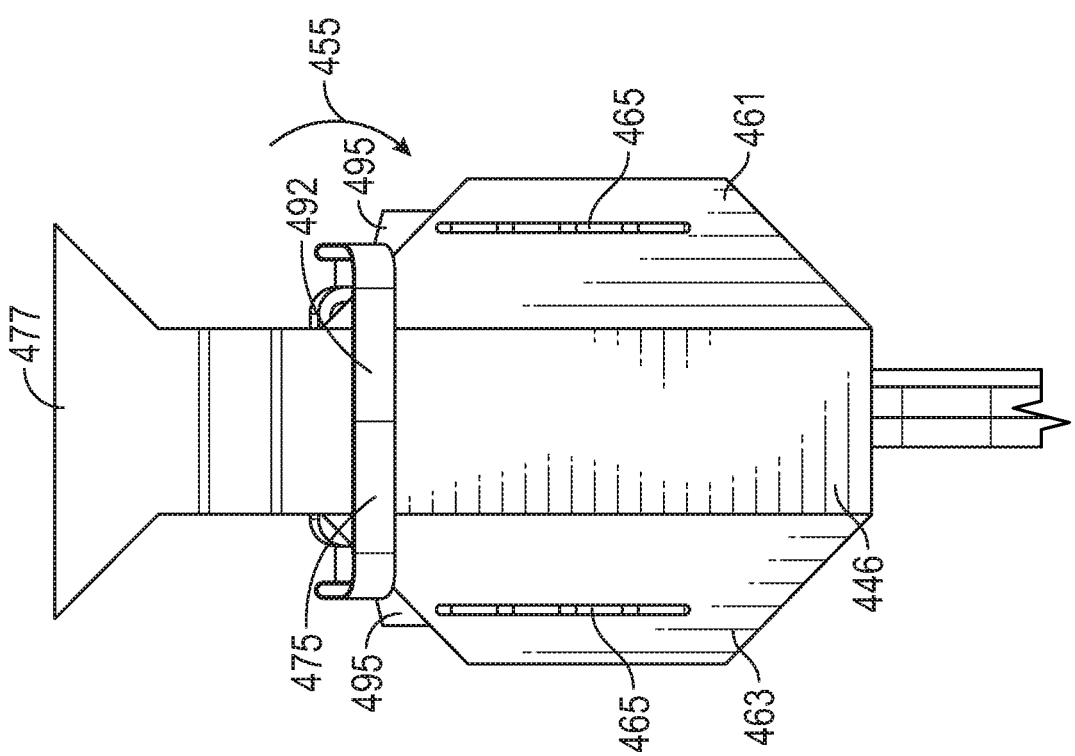
FIG. 53 is a rear side elevational view of the commissure and the commissure attachment member of FIG. 52.
Figure 52:
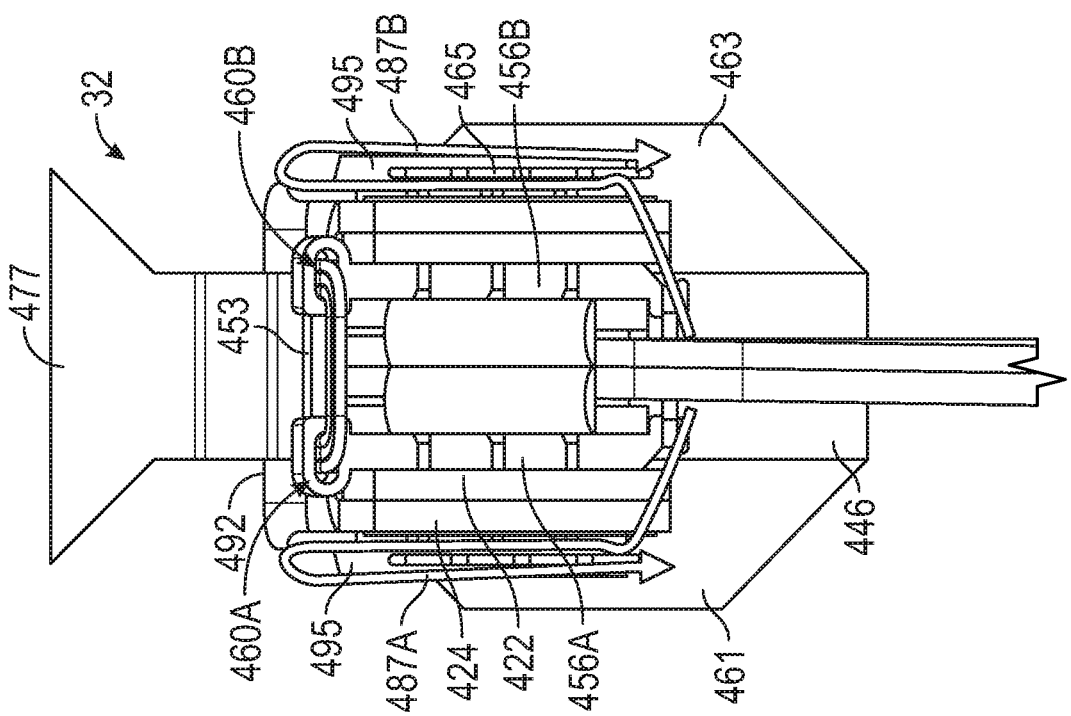
FIG. 52 is a cross-sectional view showing attachment of the commissure of FIG. 50 to a commissure attachment member.

Referring to FIGS. 52 and 53, the attachment member 492 of the assembled commissure 32 can then be placed around an upper portion 477 of an outer support member 446. The suture tails 487A, 487B can then be used to suture the attachment member 492 to the outer support member 446. For example, referring to FIG. 53, the suture tails 487A, 487B can be used to stitch the second body portion 495 of the attachment member 492 to side portions 461, 463 of the outer support member 446 to form stitches 465. The suture tails 487A, 487B can then be tied off and terminated, and the upper portion 477 of the outer support member 446 can be folded over the mid-portion 475 of the attachment member 492 in the direction indicated by arrow 455 and secured to the main body of the outer support member 446 to secure the commissure assembly 32 to the outer support member. In some embodiments, the suture tails 489A, 489B can be used to attach the attachment member 492 to the outer support member 446 (e.g., at the mid-portion 475).

In this arrangement, the reinforcing members 456A, 456B can be detached from the frame (i.e., not directly connected to the frame), and spaced radially inwardly from the frame by, for example, a distance equal to the combined thickness of the first and second layers 418, 420 of the commissure tabs 406, which are located between the reinforcing members and the interior surface of the frame. The reinforcing members 456A, 456B can restrict movement of the leaflets 400 adjacent the frame such that the leaflets articulate primarily at inner edges of the folded tab portions 418-424 in response to blood flowing through the prosthetic valve, as opposed to articulating about respective axes on or against the frame struts. For example, with reference to FIG. 54, the leaflets 400 can articulate primarily about the inner edge 421 of the second layer 420. Because the leaflets 400 articulate at a location spaced radially inwardly from the frame 12, the leaflets can avoid contact with and damage from the frame, as described above.

Figure 54:
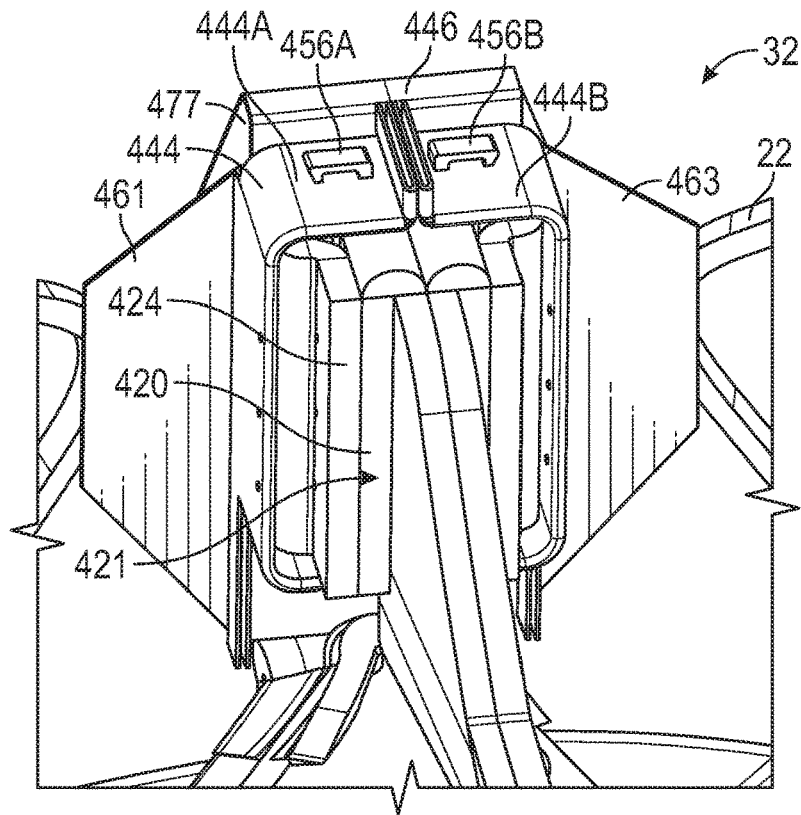
FIGS. 54-58 are various views showing the attachment of the commissure of FIG. 50 to the frame of a prosthetic heart valve using a commissure attachment member.
Figure 55:
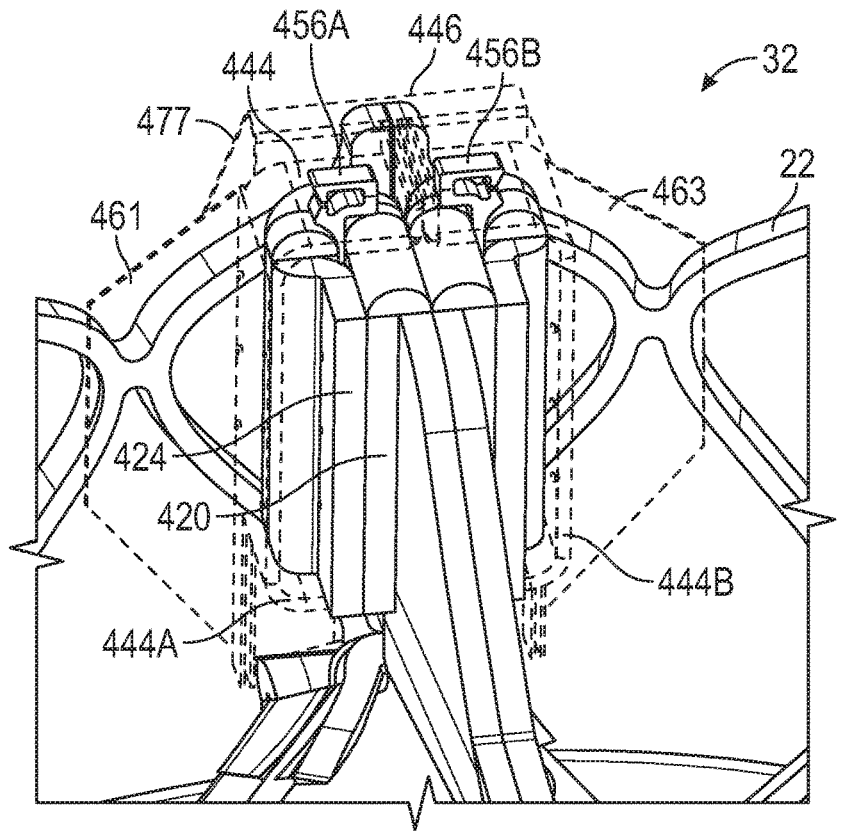
Figure 56:
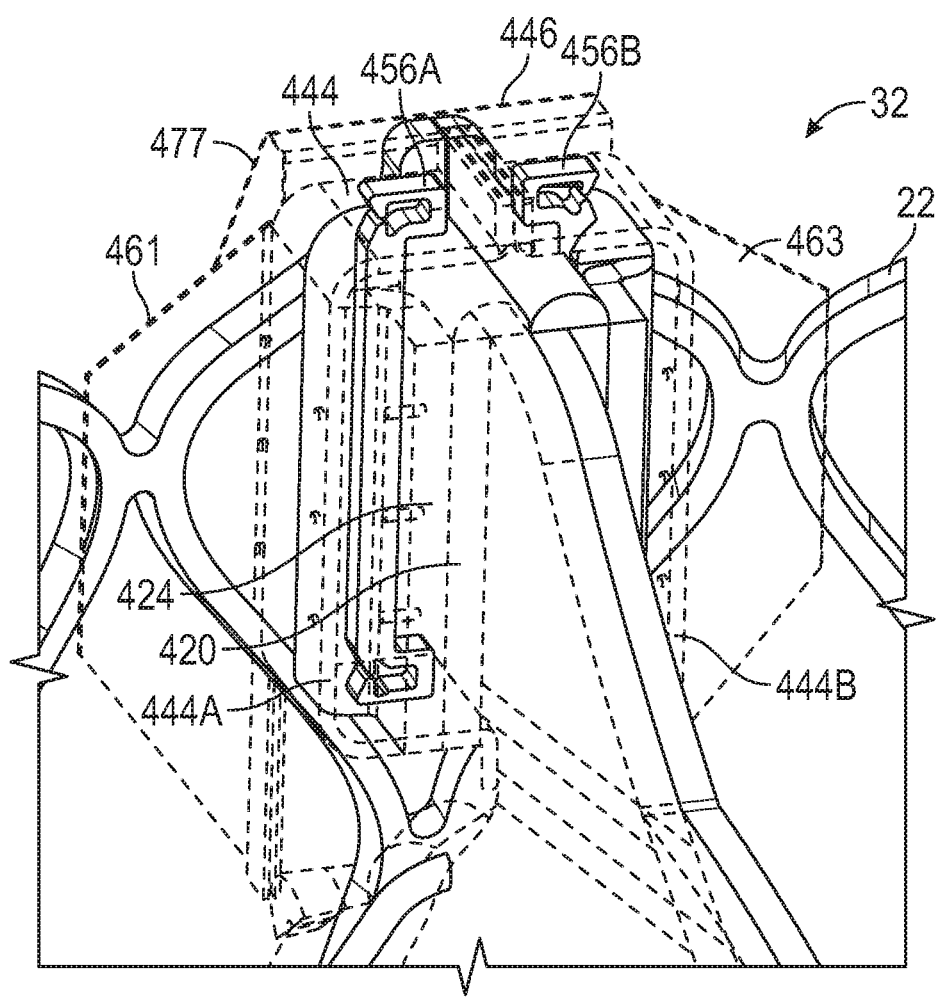
Figure 58:
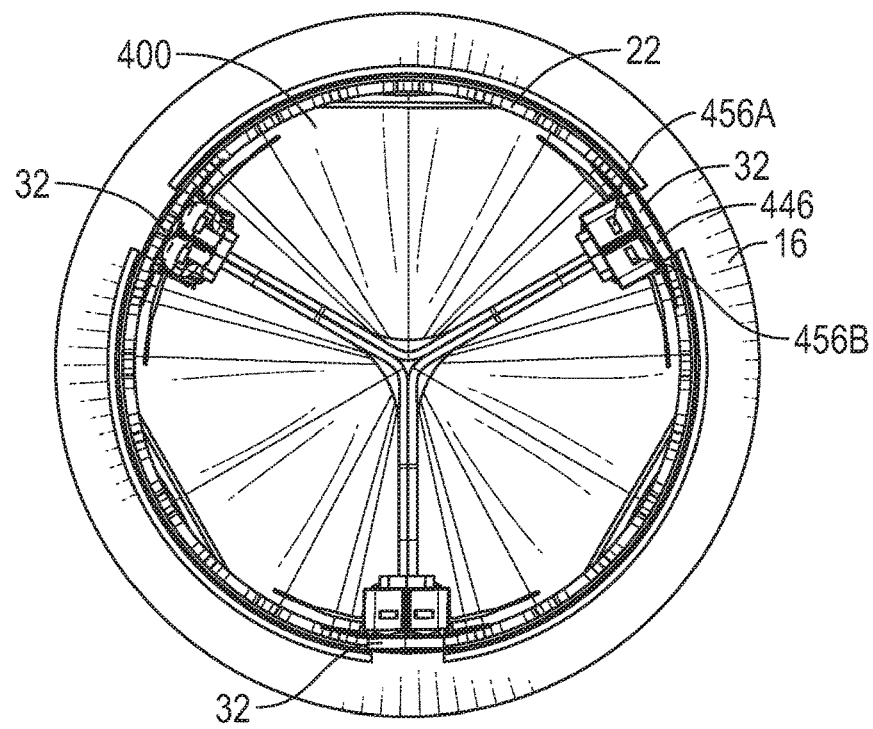

FIGS. 54-58 are additional views of the commissure 32 of FIGS. 37-53. FIG. 54 is a perspective view of the commissure 32 illustrating the entirety of the outer support member 446 and the first and second portions 444A, 444B of the inner sleeve 444. In certain embodiments, the top portions of the first and second portions 444A and 444B of the inner sleeve 444 can comprise openings or slits to allow the respective reinforcing members 456A and 456B to at least partially protrude through the portions 444A and 444B, as illustrated in FIG. 54. In other embodiments, the reinforcing members 456A and 456B can be disposed fully within the portions 444A and 444B of the inner sleeve 444. FIG. 55 illustrates the commissure 32 with the outer support member 446 and the inner sleeve 444 shown in phantom, and FIG. 56 shows the commissure 32 with the outer support member 446 and one of the leaflets 400 shown in phantom. As shown in FIGS. 54 and 55, the fourth layer 424 of each folded commissure tab 406 can extend beyond the third layer 422 (e.g., in a direction radially inward toward the center of the valve), and can be disposed across the end portion of the third layer 422 such that the radially innermost portion of the fourth layer 424 is adjacent the second layer 420. FIG. 57 is a top plan view of the commissure 32 with the outer support member 446 and the inner sleeve 444 outlined in phantom. FIG. 58 is a top plan view of the prosthetic valve of FIG. 37 illustrating the three commissures 32.

FIG. 59 illustrates an embodiment of a commissure support element configured as a clasp member 500 that can be used to secure two leaflets together to form a commissure. The clasp member 500 includes a first end portion 502 (also referred to as a first member), an intermediate portion 504, and second end portion 506 (also referred to as a second member). In the illustrated embodiment, the clasp member 500 is configured to be bent or otherwise plastically deformed from a straight configuration to a curved or U-shaped configuration, as shown in FIG. 60. To this end, the intermediate portion 504 can have a thickness t that is less than the thicknesses of the first and second end portions 502, 506 to facilitate bending of the intermediate portion with a tool 508. The first and second end portions 502, 506 can also define one or more recesses 510. In the illustrated embodiment, the first and second end portions 502, 506 have an equal number of recesses 510 located so as to form corresponding pairs of recesses when the clasp member 500 is in the bent configuration, as shown in FIG. 59.

Referring to FIGS. 61A and 61B, two leaflets 512 including commissure tabs 514 can be situated such that the commissure tabs 514 are adjacent one another, and the clasp member 500 can be placed on the commissure tabs of the leaflets such that the first end portion 502 is disposed on the commissure tab 514 of one leaflet 512 and the second end portion 506 is disposed on the commissure tab 514 of the other leaflet. The leaflets 512 can be spaced apart such that the intermediate portion 504 is located between the two commissure tabs 514. The clasp member 500 can be secured to the commissure tabs 514 by suturing. For example, the first end portion 502 can be secured to the respective leaflet 512 with sutures 516 received in the recesses 510. The second end portion 506 can be secure to the respective leaflet 512 in a similar manner.

Figure 62A:
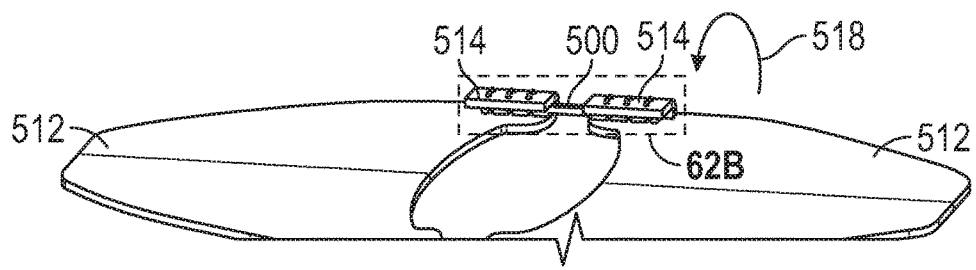
Figure 62B:
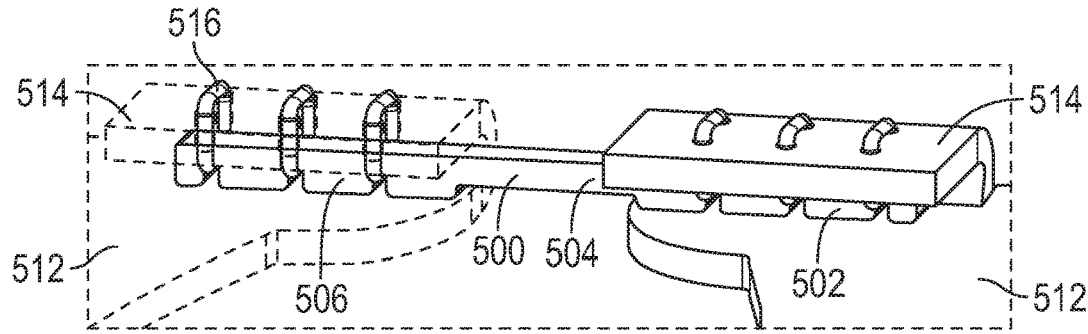
Figure 63A:
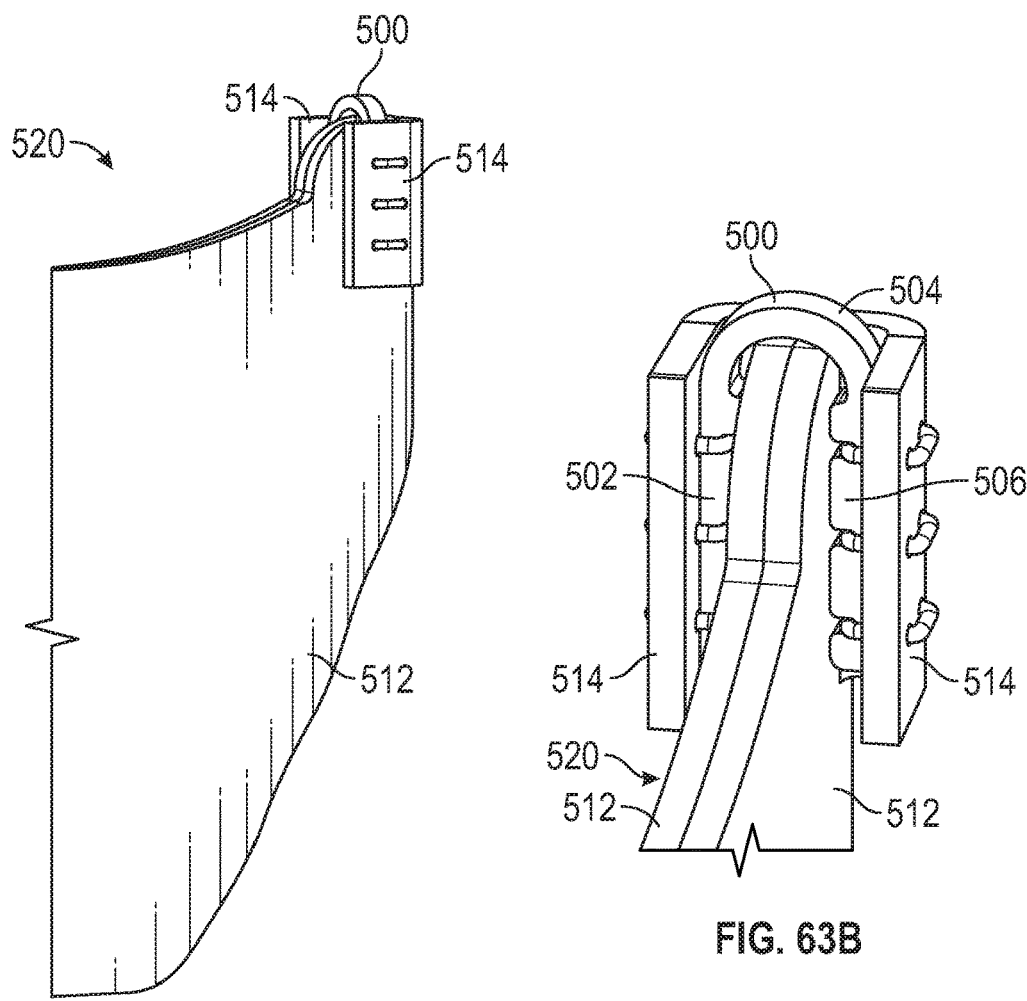
Figure 63B:
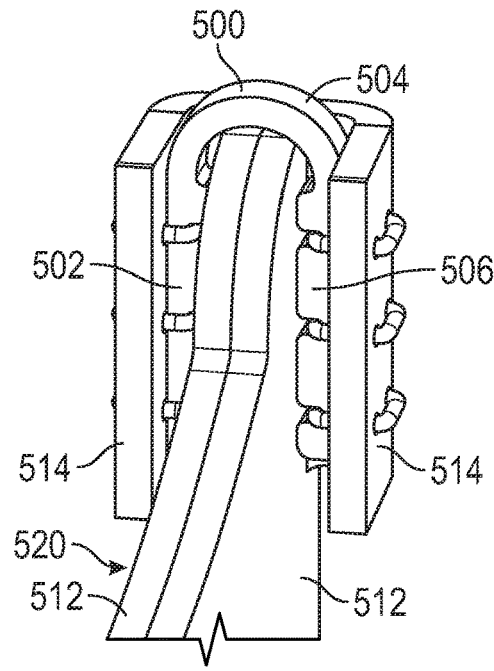

As shown in FIGS. 62A and 62B, the commissure tabs 514 can then be folded over the clasp member 500 in the direction indicated by arrow 518. The clasp member 500 can then be bent or otherwise plastically deformed into a U-shape to form a commissure 520, as shown in FIGS. 63A and 63B. In FIG. 62B, the outline of one leaflet 512 is shown in phantom to illustrate the sutures 516 connecting the second end portion 506 of the clasp member to the commissure tab 514. The clasp member 500 can restrict movement of the leaflets such that the leaflets articulate about axes spaced inwardly from a prosthetic valve frame into which the leaflets are incorporated. For example, the leaflets can articulate about the clasp member 500, and/or about the inward edges of the commissure tabs 514.

The clasp member 500 can be made from any suitable biocompatible and plastically deformable material, such as any of various metals including nitinol, stainless steel, cobalt chromium, etc., or other materials such as plastics. The assembled leaflet structure can be attached to a frame by suturing, or any other suitable attachment method, and the clasp member 500 can be detached (not directly connected) and spaced inwardly from the frame.

Figure 65:
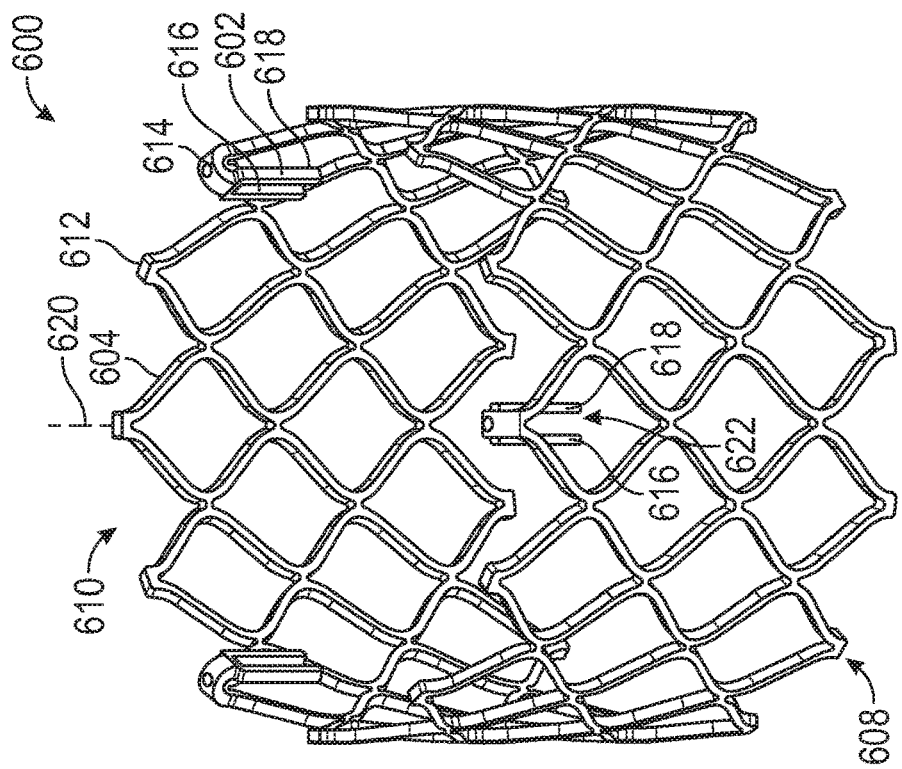
FIGS. 64 and 65 are perspective views of another embodiment of a frame including integral commissure clasp members.
Figure 64:
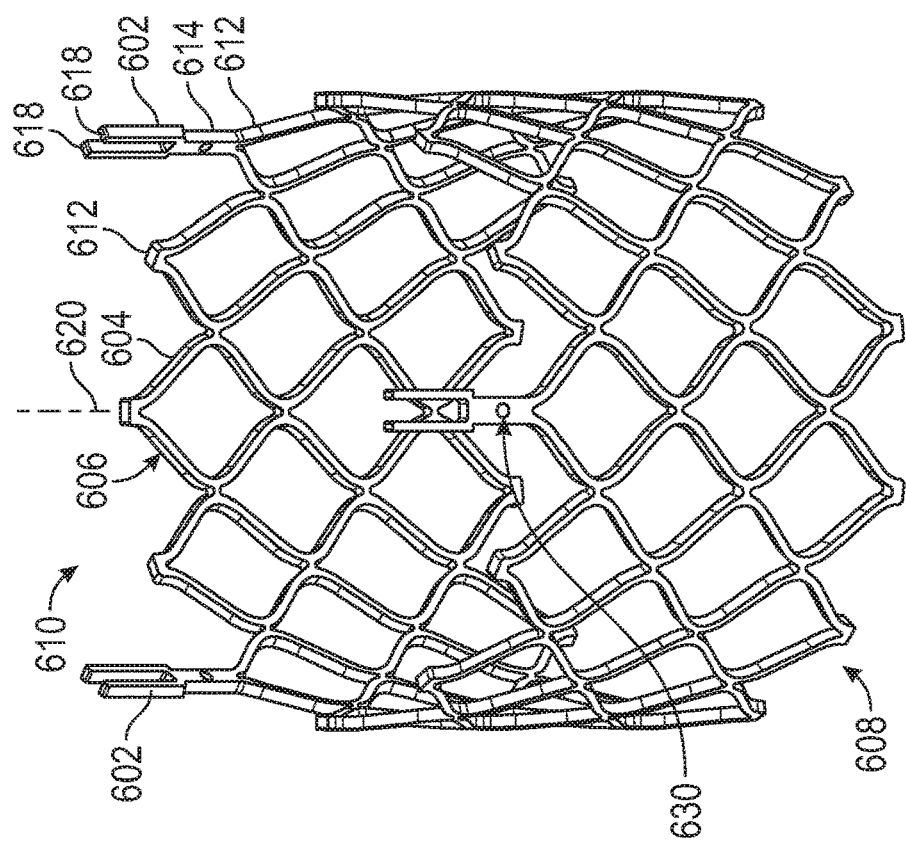
Figure 66:
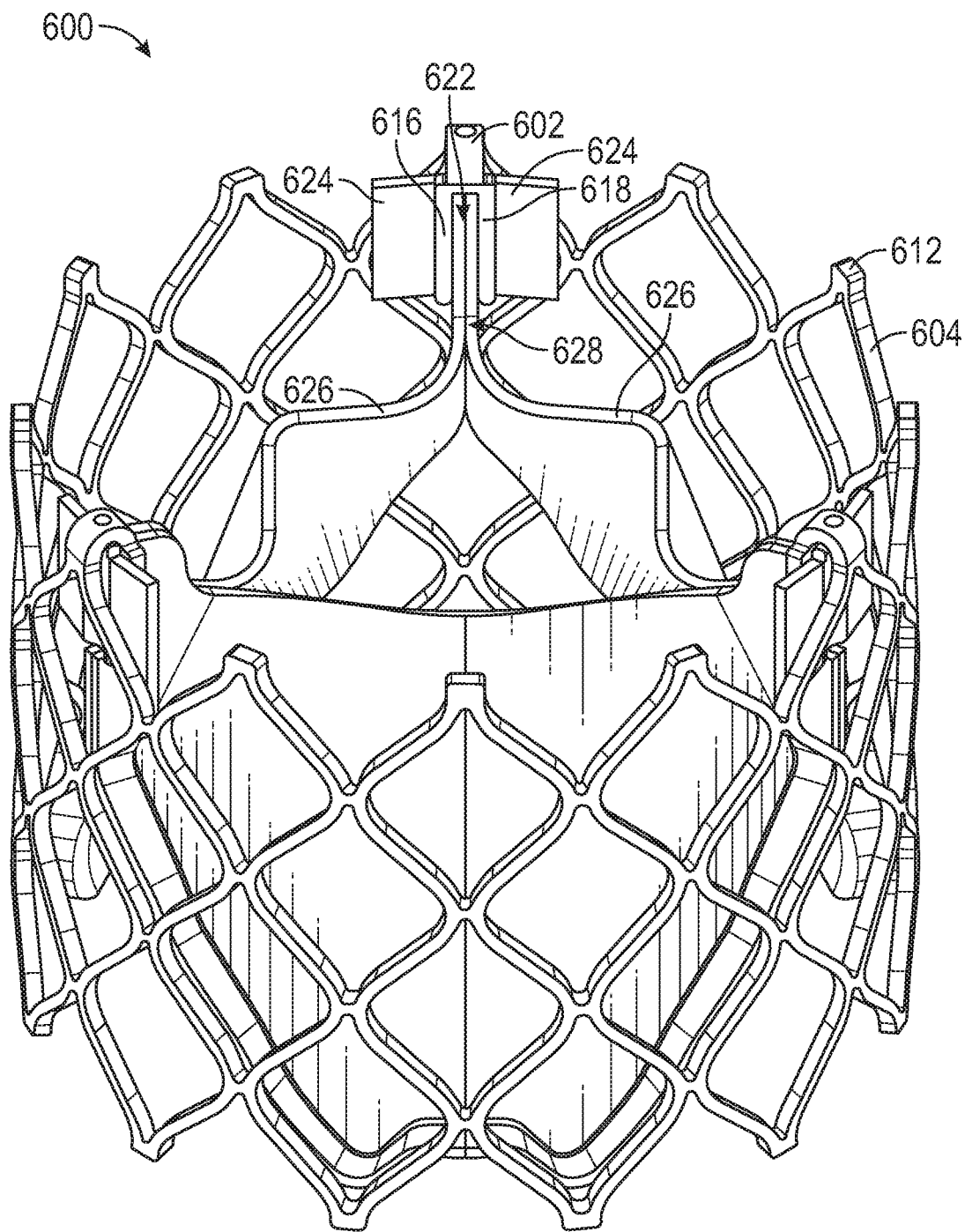
FIG. 66 is a perspective view illustrating a leaflet structure situated in the frame of FIG. 64 with the clasp members holding respective pairs of leaflets to form commissures.

FIGS. 64-66 illustrate an embodiment of a frame 600 for a prosthetic heart valve including commissure support elements configured as integral clasp members 602 that can be used to secure two leaflets together to form a commissure. The frame 600 can comprise a plurality of circumferentially extending rows of angled struts 604 defining rows of cells 606 of the frame, similar to the frame 12 described above with respect to FIGS. 1A and 1B. The frame 600 can have an inflow end 608 and an outflow end 610, and the strut members 604 can intersect to form apices 612 at the inflow and outflow ends of the frame. The clasp members 602 can extend from certain of the apices 612 at the outflow end 610 of the frame, and can be circumferentially spaced apart around the frame (e.g., by about 120 degrees) at locations corresponding to the locations of commissures of the leaflet assembly when the leaflet assembly is situated in the frame (see, e.g., FIG. 66).

FIG. 64 illustrates the frame 600 in an initial configuration (e.g., after manufacture). The clasp members 602 can include base portions 614 that extend from the respective apices 612 to which the clasp members are coupled, and a pair of clasp arms 616, 618 that are spaced apart from one another and extend from the base portion 614.

In the initial configuration shown in FIG. 64, the clasp members 602 can extend in the direction of flow parallel to the longitudinal axis 620 of the frame. Referring to FIG. 65, the base portions 614 of the clasp members 602 can then be bent radially inwardly such that the clasp arms 616, 618 of the clasp members are located inside the frame 600 and extend toward the inflow end 608 of the frame. In this manner, the clasp arms 616, 618 of each clasp member 602 can define a leaflet-receiving space 622 open in the direction of the inflow end 608 of the frame. Referring to FIG. 66, respective commissure tabs 624 of a corresponding pair of leaflets 626 can be received in the leaflet-receiving space 622 between the clasping arms 616, 618 of each clasp member 602 to form commissures 628. In the illustrated embodiment, the base portions 614 can define openings 630, which can induce bending of the clasp members 602 at the location of the openings and reduce the force required to bend the clasp members.

The clasp members 602 can be integrally formed with the frame 600 (e.g., by laser cutting) and, thus, can be made of the same material as the frame. In certain embodiments, because the location of the commissures 628 is not the thickest part of the prosthetic valve assembly, the clasp members 602 do not increase the overall crimp profile of the prosthetic valve. By being integrally formed with the strut members 604 and requiring only a simple bend in order to be placed in their operational orientation, the clasp members 602 can reduce the complexity and overall time required to assemble the commissures of the prosthetic valve compared to known techniques. By being attached to the strut members of the frame, the clasp members 602 can also reduce or prevent shifting and/or tilting of the commissures 628 when the prosthetic valve is in use, and can increase manufacturing yield. In alternative embodiments, the clasp members 602 can also be separately formed and secured to the frame. During valve operation, the leaflets can articulate about inner edges of the members 618 of the clasp members 602, which can be offset radially inward from the frame 600 to prevent damage to the leaflets, as shown in FIGS. 65 and 66.

Figure 67:
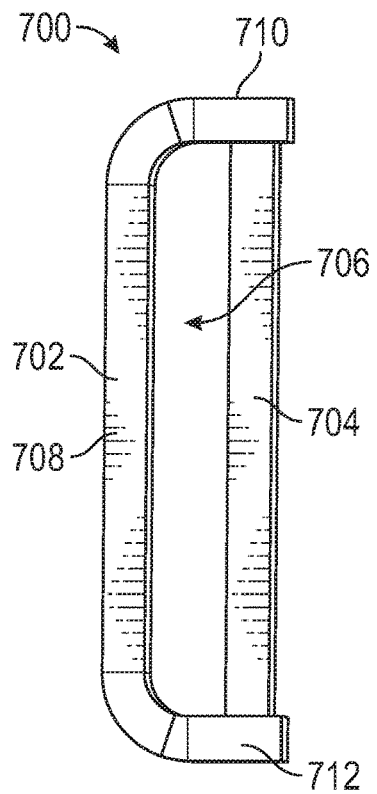
FIGS. 67-80 are perspective views of various separable members that can be secured together to form various embodiments of commissure support elements including a commissure window.
Figure 68:
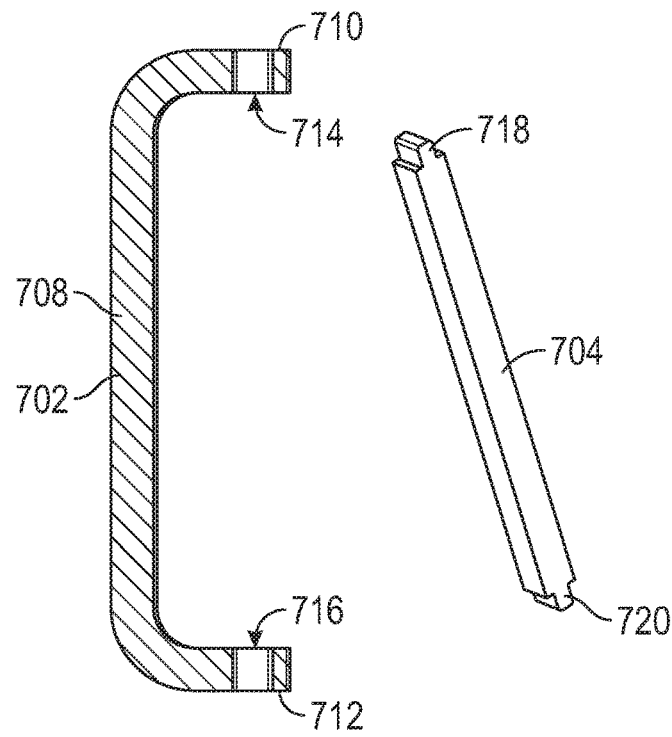

FIGS. 67-76 illustrate various other embodiments of commissure support elements configured as commissure clamps or clasp members that can be used to secure adjacent portions of adjacent leaflets (e.g., adjacent tab portions) to each other to form a commissure, which in turn can be secured to a frame (e.g., frame 12) as disclosed herein (e.g., such as shown in FIG. 37). FIG. 67 illustrates a separable clasp member 700 including a first member 702 and a second member 704 that can be assembled together to define an opening or "commissure window" 706. The first member 702 can include a main body portion 708, and first and second coupling portions 710, 712 extending perpendicularly from the main body portion 708 such that the first member 702 is C-shaped. Referring to FIG. 68, the first and second coupling portions 710, 712 of the first member 702 can define respective openings 714, 716 extending through the member and configured to receive corresponding projections 718, 720 on the second member 704.

Figure 69:
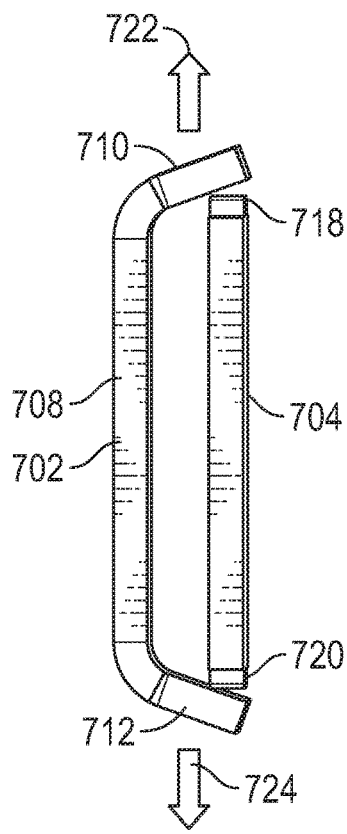

Referring to FIG. 69, to assemble the clasp member 700, the first and second coupling portions 710, 712 of the first member can be elastically deformed in the direction of arrows 722, 724. The second member 704 can be inserted between the first and second coupling portions 710, 712 of the first member 702, and the coupling portions can be allowed to return to their non-deflected state such that the projection 718 of the second member 704 is received in the opening 714 of the first coupling portion 710, and the projection 720 of the second member is received in the opening 716 of the second coupling portion 712. In this manner, the first and second members 702, 704 can be mechanically coupled together by the projections 718, 720 and the openings 714, 716 to form the commissure window 706, and reducing the likelihood of the two members separating during use.

Figure 70:
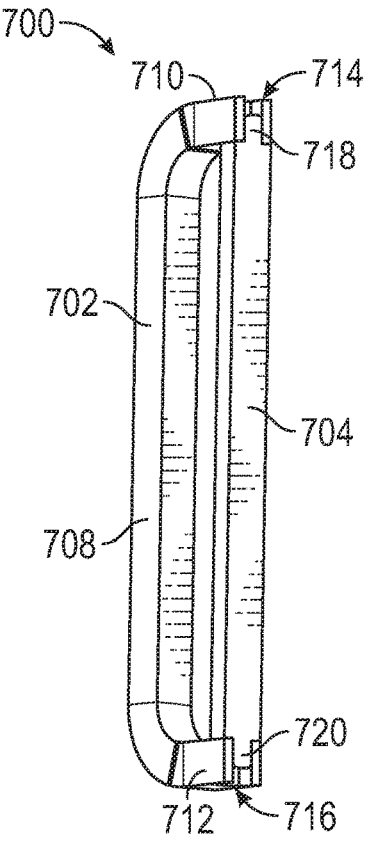
Figure 80:
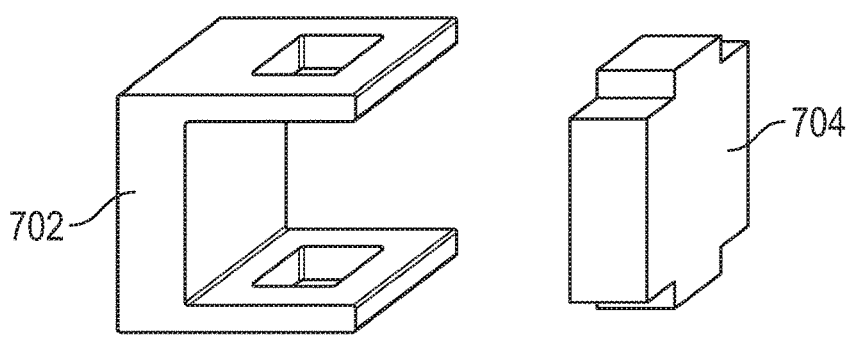

The resulting clasp member 700 can be disposed inside or outside the frame, and the commissure tabs of two leaflets can be inserted through the commissure window 706 and secured to the frame (e.g., by suturing) to form a commissure, similar to the commissures described above. In such configurations, the clasp members 700 can be detached or separate from the frame members such that the clasp members 700 are movable relative to the frame. When the clasp member 700 is located inside the frame (e.g., against or spaced inwardly from the inner surface of the frame), the clasp member can space the leaflets away from the frame to avoid abrasion. The mechanical fastening between the first member 702 and the second member 704 can reduce the time required to assemble the commissure, and the clasp member can reduce the amount of stitching required to attach the leaflets to the frame. Referring to FIG. 70, the openings 714, 716 can also be configured as slots that are open at one end such that the projections 718, 720 can be inserted into the slots without deforming the first and second coupling portions 714, 716 of the first member 702. Another alternative embodiment of the clasp member 700 is shown in FIG. 80.

Figure 72:
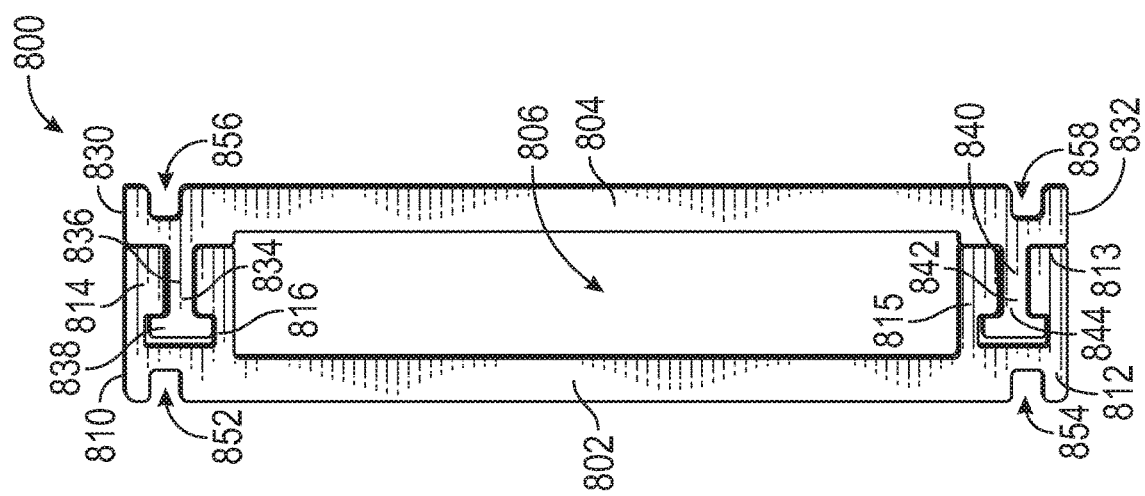
Figure 71:
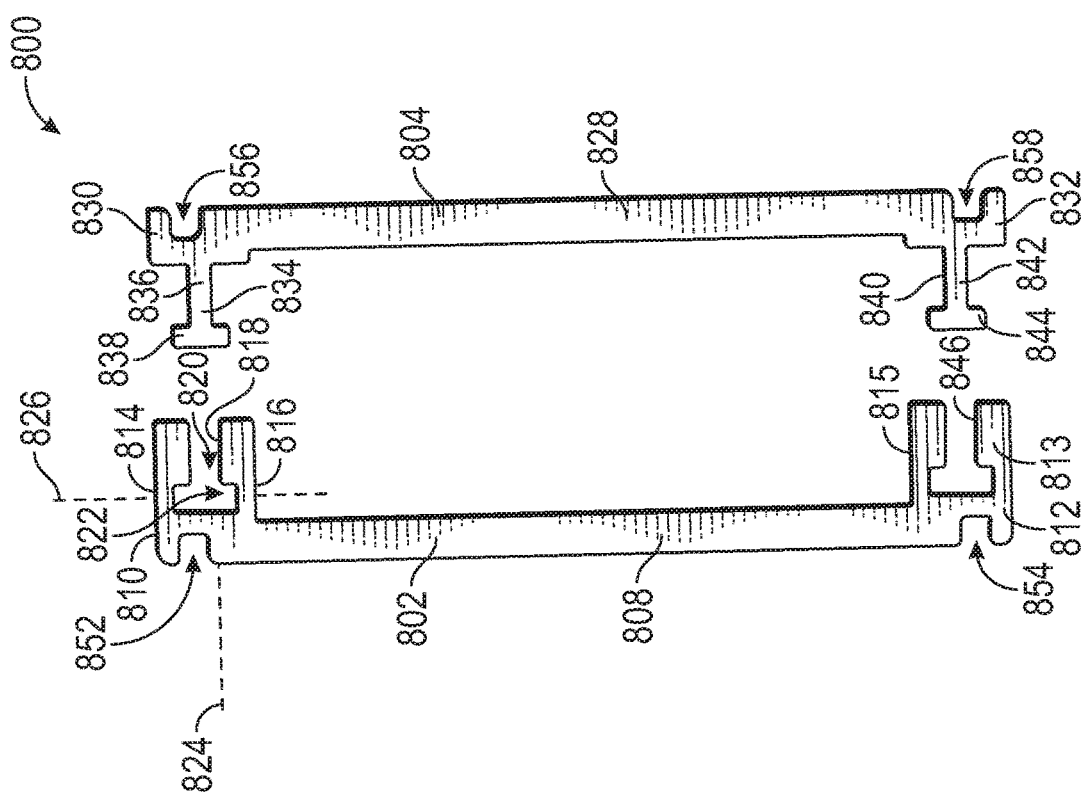

FIGS. 71-74 illustrate another embodiment of a clasp member 800 similar to the clasp member 700. The clasp member 800 can include separable first and second members 802, 804 that when assembled together define an opening or commissure window 806 (FIG. 72). The first member 802 can include a main body portion 808 and first and second coupling portions 810, 812. In the illustrated embodiment, the coupling portions 810, 812 can be female coupling portions. For example, the first coupling portion 810 can include two arms or tines 814, 816 extending perpendicular to the main body portion 808. The tines 814, 816 are shaped such that they define a T-shaped recess or keyway 818 having a first portion 820 and a second portion 822. A longitudinal axis 824 of the first portion 820 can extend perpendicular to the main body portion 808, while a longitudinal axis 826 of the second portion 822 can extend parallel to the main body portion. The second coupling portion 812 can include tines 813, 815 defining a keyway 846 similar to the keyway 818.

The second member 804 can include a main body portion 828 and first and second end portions 830, 832. The first and second end portions 830, 832 can be configured as male coupling portions. For example, the first end portion 830 can include a member 834 having a first portion 836 and a second portion 838 in a T-shaped arrangement corresponding to the keyway 818 of the first member 802. The second end portion 832 can include a member 840 having a first portion 842 and a second portion 844 in a T-shaped arrangement corresponding to the keyway 846. In this manner, the first and second members 802, 804 can be assembled to form the clasp member 800 by inserting the members 834, 840 of the second member 804 into the corresponding keyways 818, 846 of the first member 802.

Figure 73:
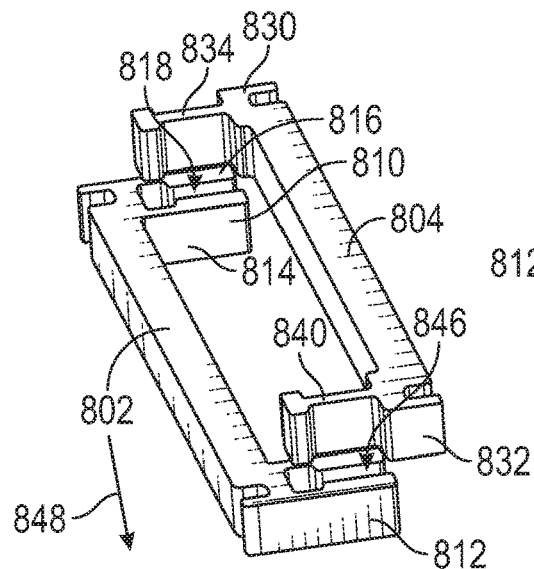
Figure 74:
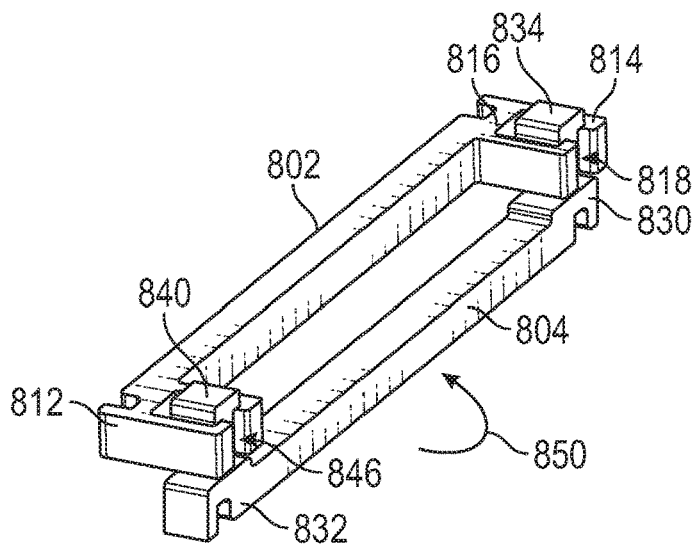

FIG. 73 illustrates one method of assembly in which the members 834, 840 of member 804 are oriented parallel to the tines (e.g., tines 814, 816) of the member 802, and the members 834, 840 are inserted into the keyways 818, 846 in the direction of arrow 848. FIG. 74 illustrates another method of assembly in which the members 834, 840 are inserted in the keyways 818, 846 and are initially oriented perpendicular to the tines (e.g., tines 814, 816) of the first member 802. The second member 804 can then be rotated in the direction of arrow 850 such that the portions 838, 844 of the members 834, 840 are received in the corresponding portions of the keyways 818, 846 to interlock the first and second members 802, 804.

When fastened together, the members 802, 804 can be prevented from moving relative to one another in the plane of the commissure window 806 by the interlocking of the members 834, 840 with the keyways 818, 846. To prevent relative movement of the members 802, 804 in a direction perpendicular to the plane of the commissure window 806, the members 802, 804 can be, for example, tied together (e.g., with suture). In the illustrated embodiment, for example, the first member 802 can a define recess 852 adjacent the first coupling portion 810 and a recess 854 adjacent the second coupling portion 812. Meanwhile, the second member 804 can include recesses 856, 858 at the respective first and second end portions 830, 832. The recesses 852, 854 can be located on the opposite side of the first member 802 from the keyways 818, 846, and the recesses 856, 858 can be located on the opposite side of the second member 804 from the T-shaped members 834, 840. In this manner, when the members 802, 804 are assembled together, the recesses 852 and 856 can be aligned with one another at the top of the commissure window 806, and the recesses 854 and 858 can be aligned with one another at the bottom of the commissure window. The first and second members 802, 804 can then be tied together using suture, thread, etc., looped through the recesses 852, 856 and the recesses 854, 858 to prevent movement of the members 802, 804 in a direction perpendicular to the plane of the commissure window 806.

Figure 75:
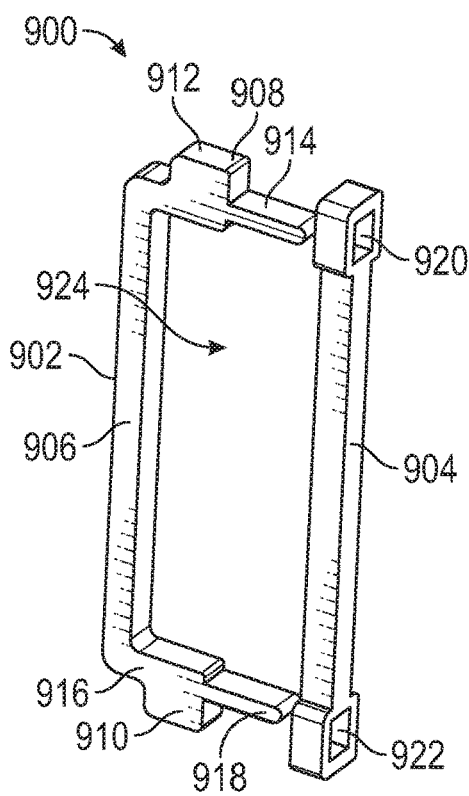
Figure 76:
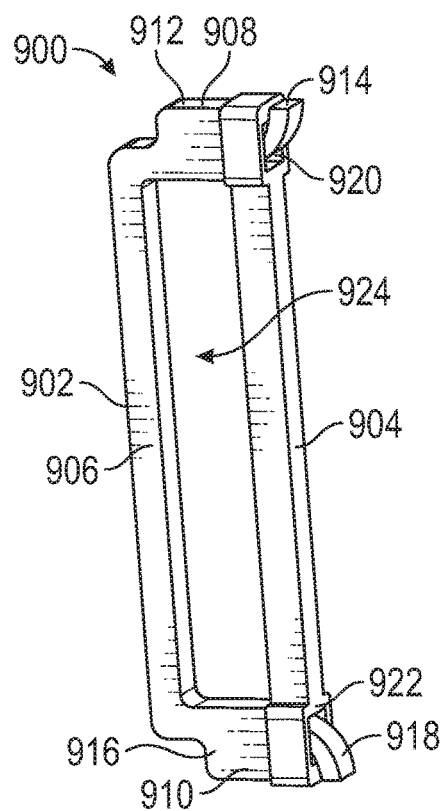

FIGS. 75 and 76 illustrate yet another embodiment of a separable clasp member 900 that can be used to form a commissure. The clasp member 900 can include a first member 902 and a second member 904. The first member 902 can include a main body portion 906, and first and second coupling portions 908, 910 that extend from the ends of the main body portion and perpendicular to the main body portion such that the first member is C-shaped. The first coupling portion 908 can include a first portion configured as a stop portion 912, and a second portion configured as a fastening portion 914. In the illustrated embodiment, the stop portion 912 is relatively thicker than the fastening portion 914. The second coupling portion 910 can include a stop portion 916 and a fastening portion 918 similar to the portions 912, 914 of the first coupling portion.

The second member 904 can include openings 920, 922 defined at respective end portions of the second member. To assemble the clasp member 900, the fastening portions 914, 918 of the first member 902 can be inserted through the corresponding openings 920, 922 of the second member 904, and the fastening portions can be bent (e.g., upwardly or downwardly) such that the end portions of the second member are retained between the respective stop portions 912, 916 and the bent fastening portions 914, 918. In this manner, the first and second members 902, 904 can define a commissure window 924.

Figure 77:
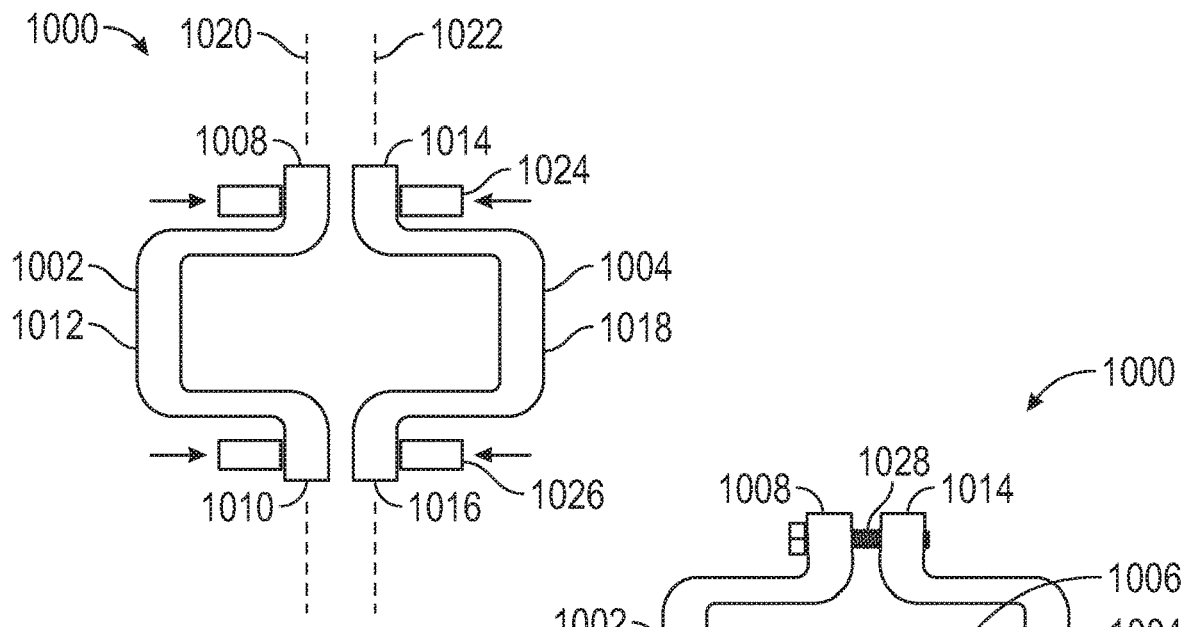
Figure 78:
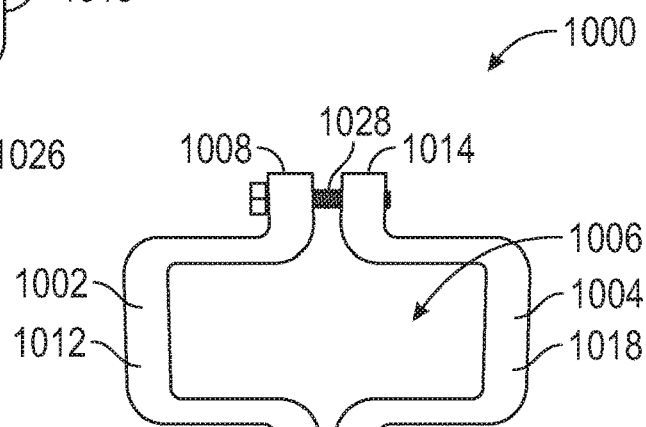
Figure 79:
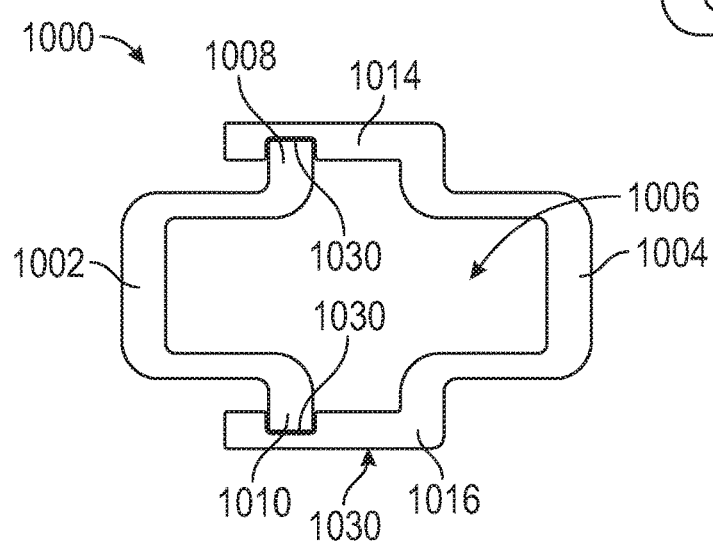

FIGS. 77-79 illustrate further embodiments of commissure clasps 1000 including two separable members 1002, 1004, both of which are C-shaped such that the clasp members define a commissure window 1006 when assembled together. The first member 1002 can include a first coupling portion 1008 and a second coupling portion 1010 with a main body portion 1012 extending therebetween. The second member 1004 can include a first coupling portion 1014 and a second coupling portion 1016, with a main body portion 1018 extending therebetween. The coupling portions 1008, 1010 of the first clasp member 1002 and the coupling portions 1014, 1016 of the second clasp member 1004 can be aligned along respective vertical axes 1020, 1022. The main body portions 1012, 1018 can be offset from the respective vertical axes 1020, 1022 such that the clasp members 1002, 1004 are C-shaped and define the commissure window 1006 when assembled together.

The clasp members 1002, 1004 can be secured to one another in a variety of ways. For example, the clasp members 1002, 1004 can be sutured together using sutures, or coupled together using any of various crimpable tabs or clamps. For example, as shown in FIG. 77, a clamp member 1024 can be disposed around the coupling portions 1008, 1014 at the tops of the members 1002, 1004, and clamp member 1026 can be disposed around the coupling portions 1010, 1016 at the bottom of the members. The clamp members 1024, 1026 can be crimped around the respective coupling portions to secure the members together. The clamp members 1024, 1026 can be, for example, ring shaped clamp members that extend all the way around the top and bottom portions of the members 1002, 1004, or alternatively the clamp members 1024, 1026 can be C-shaped clamp members that extend partially around the top and bottom portions of the members 1002, 1004.

The clasp members 1002, 1004 can also be secured to one another by one or more fasteners. For example, as shown in FIG. 78, a fastener 1028 (e.g., a screw or bolt) can extend through the coupling portions 1008, 1014, or through the coupling portions 1010, 1016, or both.

FIG. 79 illustrates another embodiment of the leaflet clasp 1000 in which the coupling portions 1014, 1016 of the second member 1004 extend over and engage the coupling portions 1008, 1010 of the first member 1002. In the illustrated embodiment, the coupling portions 1014, 1016 can define one or more recesses 1030 configured to receive the coupling portions 1008, 1010 when the clasp members 1002, 1004 are assembled together.

Figure 81:
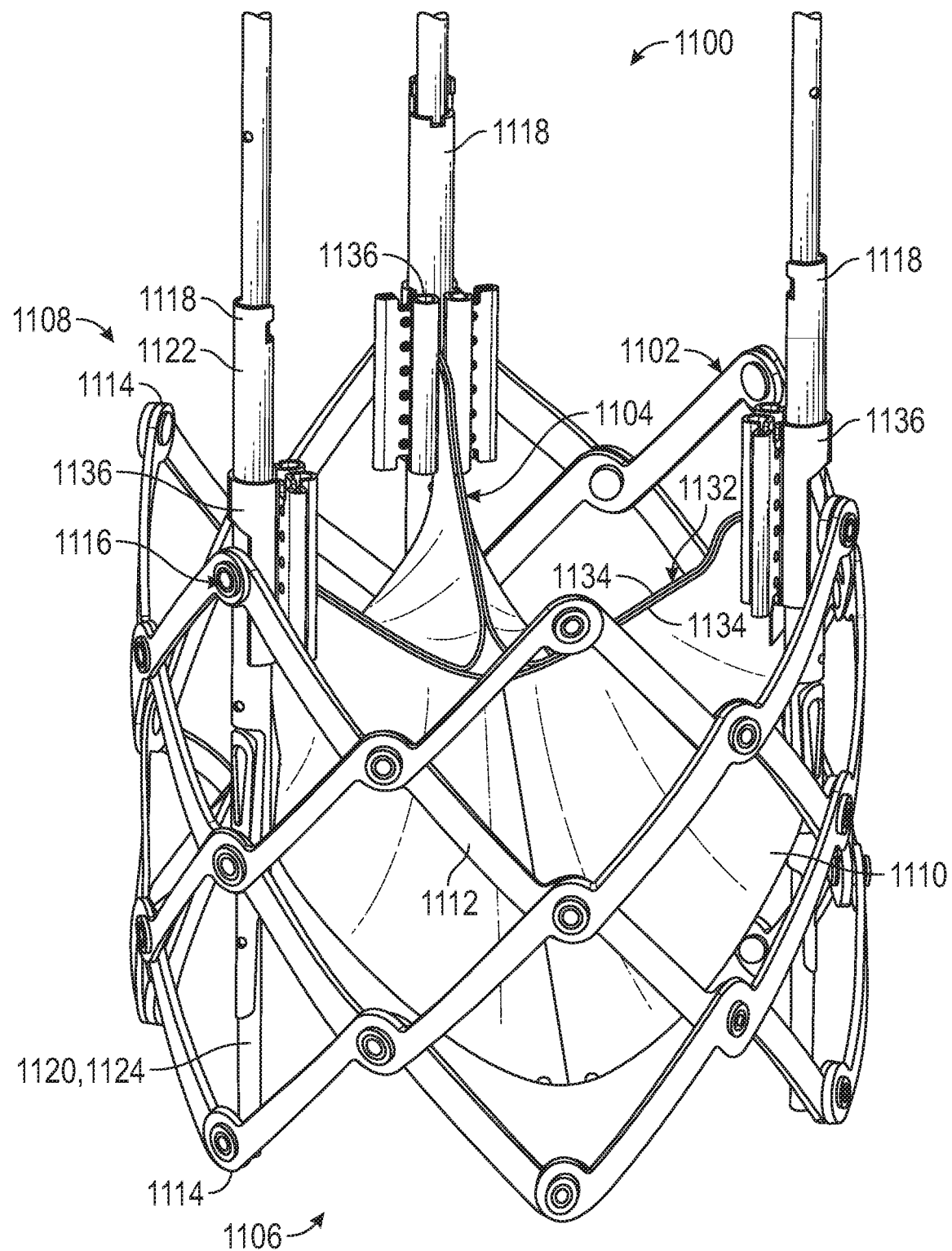
FIG. 81 is a perspective view illustrating another embodiment of a prosthetic heart valve including a plurality of commissure support elements configured as commissure clamps.

FIG. 81 illustrates another embodiment of a prosthetic valve 1100. The prosthetic valve 1100 can include an annular stent or frame 1102, and a leaflet structure 1104 situated within and coupled to the frame 1102. The frame 1102 can include an inflow end 1106 and an outflow end 1108. The leaflet structure can comprise a plurality of leaflets 1110, such as three leaflets arranged to collapse in a tricuspid arrangement similar to the aortic valve such that the leaflets form commissures 1132 where respective outflow edge portions 1134 of the leaflets contact each other. Alternatively, the prosthetic valve can include two leaflets 1110 configured to collapse in a bicuspid arrangement similar to the mitral valve, or more than three leaflets, depending upon the particular application.

With reference to FIG. 81, the frame 1102 can include a plurality of interconnected lattice struts 1112 arranged in a lattice-type pattern and forming a plurality of apices 1114 at the outflow end 1108 of the prosthetic valve. The struts 1112 can also form similar apices at the inflow end 1106 of the prosthetic valve. The lattice struts 1112 can be pivotably coupled to one another by hinges 1116 located where the struts overlap each other, and also at the apices 1114. The hinges 1116 can allow the struts 1112 to pivot relative to one another as the frame 1102 is expanded or contracted, such as during assembly, preparation, or implantation of the prosthetic valve 1100. The hinges 1116 can comprise rivets or pins that extend through apertures formed in the struts 1112 at the locations where the struts overlap each other. Additional details regarding the frame 1102 and devices and techniques for radially expanding and collapsing the frame can be found in U.S. patent application Ser. No. 15/831,197, filed on Dec. 4, 2017, which is incorporated herein by reference.

As illustrated in FIG. 81, the frame 1102 can comprise a plurality of actuators 1118 that can also function as release-and-locking units (also referred to as locking assemblies) configured to radially expand and contract the frame. In the illustrated configuration, the frame 1102 can comprise three actuators 1118 coupled to the frame 1102 at circumferentially spaced locations, although the frame may include more or fewer actuators depending upon the particular application. Each of the actuators 1118 generally can comprise an inner member 1120, such as an inner tubular member, and an outer member 1122, such as an outer tubular member concentrically disposed about the inner member 1120. The inner members 1120 and the outer members 1122 can be moveable longitudinally relative to each other in a telescoping manner to radially expand and contract the frame 1102, as further described in U.S. patent application Ser. No. 15/831,197 incorporated by reference above.

In the illustrated configuration, the inner members 1120 can have distal end portions 1124 coupled to the inflow end 1106 of the frame 1102 (e.g., with a coupling element such as a pin member). In the illustrated embodiment, each of the inner members 1120 are coupled to the frame at respective apices 1114 at the inflow end 1106 of the frame. The outer members 1122 can be coupled to apices 1114 at the outflow end 1108 of the frame 1102 at, for example, a mid-portion of the outer member, as shown in FIG. 81, or at a proximal end portion of the outer member, as desired.

The inner member 1120 and the outer member 1122 can telescope relative to each other between a fully contracted state (corresponding to a fully radially expanded state of the prosthetic valve) and a fully extended state (corresponding to a fully radially compressed state of the prosthetic valve). In the fully extended state, the inner member 1120 is fully extended from the outer member 1122. In this manner, the actuators 1118 allow the prosthetic valve to be fully expanded or partially expanded to different diameters and retain the prosthetic valve in the partially or fully expanded state.

Referring to FIG. 81, the prosthetic valve 1100 can include a plurality of commissure support elements configured as commissure clasps or clamps 1136. In the illustrated configuration, the prosthetic valve includes a commissure clamp 1136 positioned at each commissure 1132 and configured to grip the leaflets 1110 of the commissure at a location spaced radially inwardly of the frame 1102.

Figure 82:
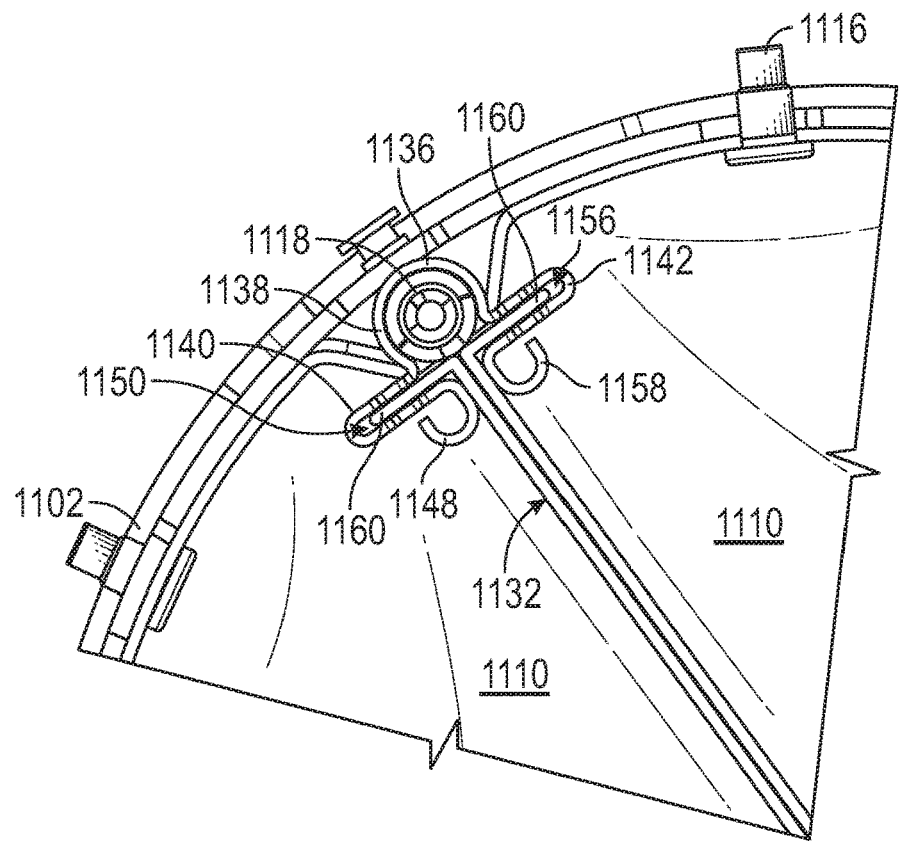
FIG. 82 is a plan view illustrating a portion of the prosthetic heart valve of FIG. 81.
Figure 83:
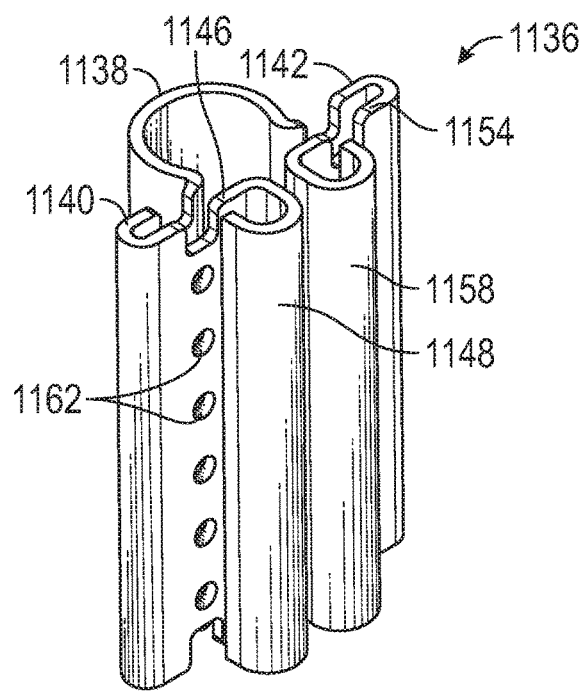
FIG. 83 is a perspective view of a commissure clamp, according to one embodiment.
Figure 84:
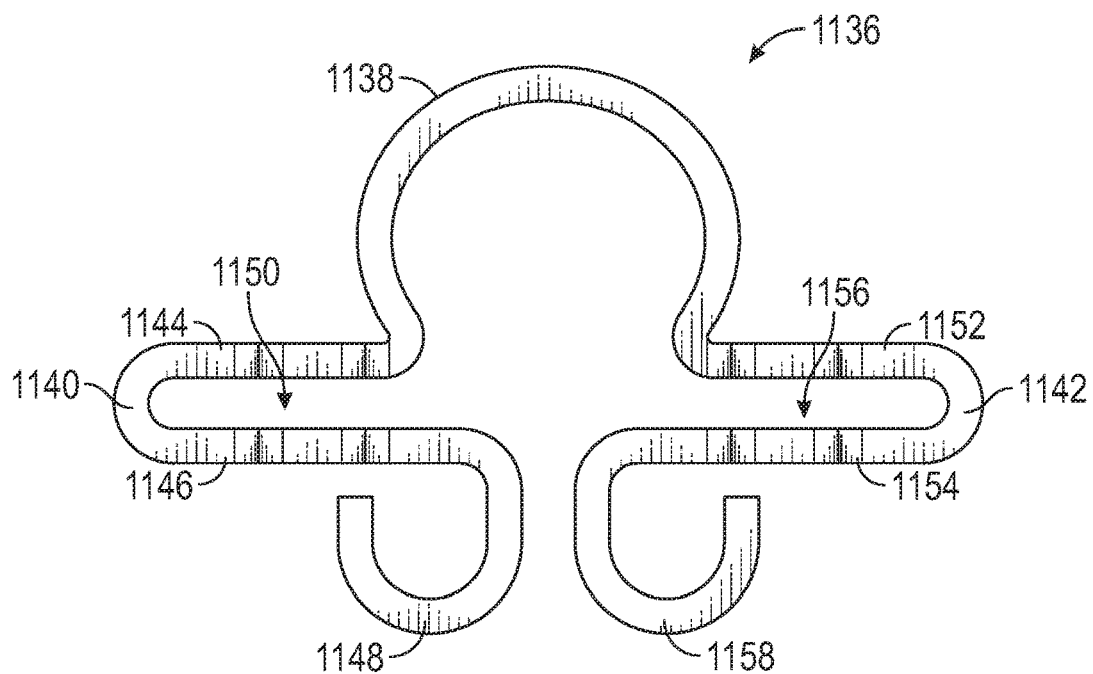
FIG. 84 is a plan view of the commissure clamp of FIG. 83.

FIGS. 82-84 illustrate a representative commissure clamp 1136 in greater detail. The commissure clamp 1136 can include a main portion or coupling portion 1138 configured as a cylindrically-shaped recessed portion or collar, and first and second clamp members 1140, 1142 extending curvilinearly from opposite sides of the coupling portion 1138. As best shown in FIG. 84, the first clamp member 1140 can include a first portion 1144 extending away from the coupling portion 1138. The clamp member 1140 can be curved (e.g., by 180°) such that a second portion 1146 extends from the first portion 1144 parallel to and spaced apart from the first portion 1142 in a direction back toward the coupling portion 1138. A third portion 1148 can extend from the second portion 1146, and can curve around (e.g., by 180°) such that an end portion of the third portion 1148 is adjacent a mid-portion of the second portion 1146. The first and second portions 1144, 1146 can define a leaflet-receiving space 1150 therebetween. The second clamp member 1142 can be symmetrical with the first member 1140, and can include first and second portions 1152, 1154 defining a leaflet-receiving space 1156 opposite the leaflet-receiving space 1150 and in communication with the leaflet-receiving space 1150. A curved third portion 1158 can extend from the second portion 1154 similar to the portion 1148 of the first member 1140. As shown in FIG. 83, the inward-facing surfaces of the second portions 1146, 1154 can comprise openings 1162.

Referring again to FIG. 81, the commissure clamps 1136 can be situated on the actuators 1118 such that the outer members 1122 are received in the coupling portions 1138 of the commissure clamps, and such that the leaflet-receiving spaces 1150 and 1156 extend at an angle to the commissure 1132 (e.g., at an angle of 90°). The coupling portion 1138 can be sized and shaped to frictionally engage and/or clamp onto the outer surface of the outer member 1122 of the actuator 1118 so as to secure the commissure clamp 1136 to the outer member 1122. In lieu of or in addition to frictional or clamping forces, the coupling portion 1138 can be welded to the outer member 1122, or secured to the outer member 1122 using an adhesive, sutures and/or mechanical fasteners.

As shown in FIGS. 81 and 82, commissure tabs 1160 of the leaflets 1110 can be inserted into the leaflet-receiving spaces 1148, 1152 of the commissure clamps 1136 at each commissure. For example, the commissure tab 1160 of one leaflet 1110 can be folded around the third portion 1148 and inserted into the leaflet-receiving space 1150 such that a portion of the commissure tab extends radially between the third portions 1148, 1158 of the members 1140, 1142, and the portion of the commissure tab in the leaflet-receiving space extends circumferentially along the frame. The commissure tab 1160 of the other leaflet 1110 can be folded and inserted into the leaflet-receiving space 1156 in a similar manner. In certain configurations, the leaflets 1110 can be sutured to the commissure clamps 1136 through the openings 1162.

The curved third portions 1148, 1158 of the first and second clamp members can cooperate to grip the leaflets 1110 of each commissure 1132 at a location that is offset radially inwardly from the strut members of the frame 1102. In this manner, the leaflets 1110 can articulate about axes offset from the frame 1102 as they coapt and move away from each other during valve operation. For example, in the illustrated configuration the leaflets 1110 can articulate about the third portions 1148, 1158 of the first and second clamp members 1140, 1142. In certain configurations, the portions 1148, 1158 can be smooth, and can have relatively large radii configured to reduce stress and/or damage to the leaflets where the leaflets contact the members 1140, 1142 during valve operation.

Figure 85:
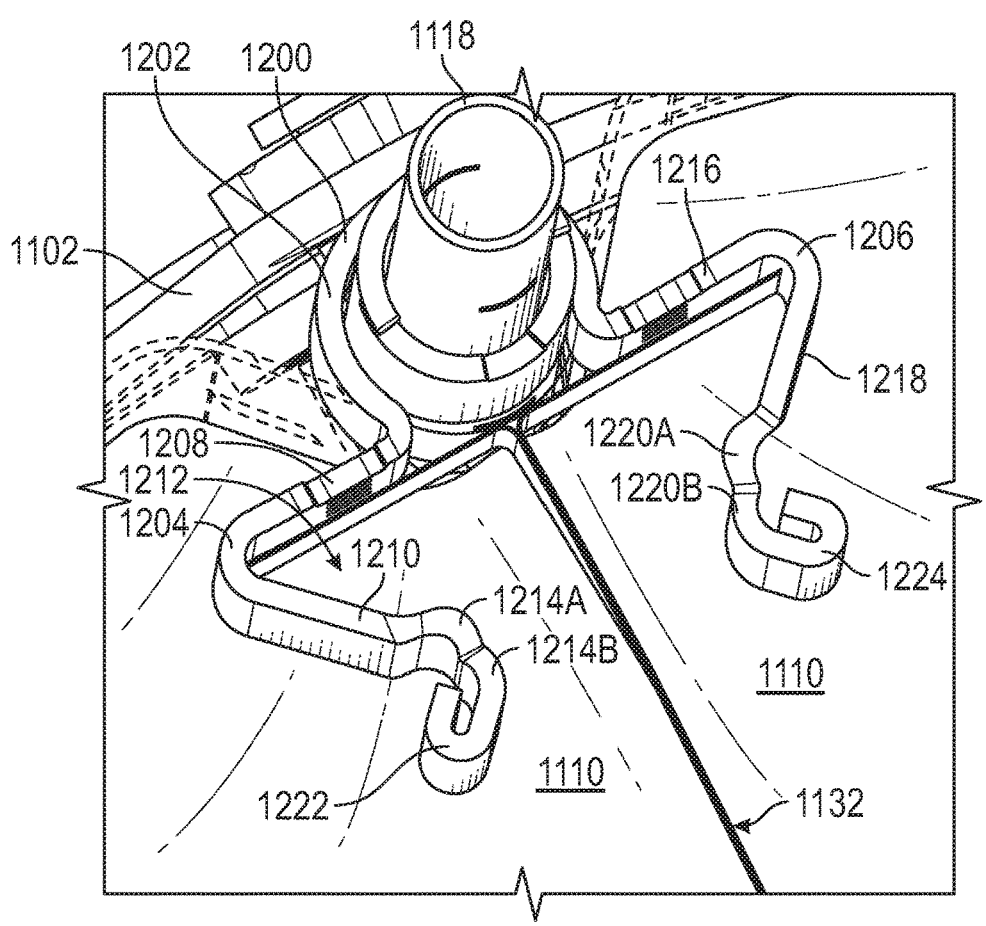
FIG. 85 is a perspective view illustrating a portion of the prosthetic heart valve of FIG. 81 including another embodiment of a commissure clamp.

FIG. 85 illustrates another embodiment of a commissure clamp 1200 that can be used in combination with the prosthetic valve 1100 of FIG. 81. In FIG. 85, the commissure clamp 1200 is shown in an open configuration prior to crimping or closing of the clamping arms to clamp the leaflets 1110. The commissure clamp 1200 can include a main portion configured as a coupling portion 1202 defining a cylindrically-shaped recess shaped to be placed around an actuator. The commissure clamp can further comprise first and second clamp members 1204, 1206 extending from the coupling portion 1202. The first clamp member 1204 can include a first portion 1208 extending outwardly from the coupling portion 1202, and a second portion 1210 extending at an angle to the first portion 1208 such that the first and second portions 1208, 1210 define a leaflet-receiving space 1212. The second portion 1210 can include one or more curved portions configured as leaflet-engaging portions 1214. In the illustrated embodiment, the first clamp member 1204 includes two leaflet-engaging portions 1214A and 1214B, wherein the leaflet-engaging portion 1214B is offset from the leaflet-engaging portion 1214A in a direction radially inward toward the center of the prosthetic valve in the position illustrated in FIG. 85.

The second clamp member 1206 can be configured similar to the first clamp member 1204, with a first portion 1216 extending from the coupling portion 1202 in the opposite direction from the first portion 1208 of the first clamp member 1204. The second clamp member 1206 can further include a second portion 1218 extending at an angle to the first portion 1216. The second portion 1218 can include two curved leaflet-engaging portions 1220A and 1220B opposing the leaflet-engaging portions 1214A, 1214B of the first member 1204. In the configuration illustrated in FIG. 85, the leaflet-engaging portion 1220B can be offset from the leaflet-engaging portion 1220A in a direction radially inward toward the center of the prosthetic valve, similar to the leaflet-engaging portion 1214B.

The second portions 1210, 1218 of the first and second clamp members 1204, 1206 can be configured to clamp the leaflets 1110 (or commissure tabs of the leaflets) when the leaflets are inserted between the first and second clamp members. In certain embodiments, the second portions 1210 and 1218 of the respective clamp members 1204 and 1206 can be crimped from the open position shown in FIG. 85 to a closed position wherein the portion 1210 is parallel to the portion 1208 and the portion 1218 is parallel to the portion 1216, similar to the embodiment of FIG. 84. In the closed configuration, the leaflet-engaging portion 1214A can clamp the leaflet 1110 on the left side of FIG. 85 against the portion 1208, and the leaflet-engaging portion 1220A can clamp the leaflet 1110 on the right side of FIG. 85 against the portion 1216. Meanwhile, the leaflets 1110 can also be clamped or pressed together between the leaflet-engaging portions 1214B and 1220B, and/or between the curved end portions 1222 and 1224 of the respective members 1204 and 1206. In this manner, the leaflets 1110 can articulate about axes adjacent the end portions 1222 and 1224 spaced radially inwardly from the frame 1102. In other embodiments, the clamp members 1204 and 1206 can remain in the configuration illustrated in FIG. 85, and the leaflet-engaging portions 1214A and 1220A can cooperate to clamp the leaflets 1110 at a first location, and the leaflet-engaging portions 1214B and 1220B can clamp the leaflets at a second location adjacent the first location. In this manner, the leaflets 1110 can articulate about axes adjacent the leaflet-engaging portions 1214B and 1220B, and offset radially inwardly from the frame 1102. Additionally, in certain configurations, clamping the leaflets at multiple locations, such as between the leaflet-engaging portion 1214A and the portion 1208 on the left side of FIG. 85, between the leaflet-engaging portion 1220A and the portion 1216 on the right side of FIG. 85, between the portions 1214B and 1220B, and/or between the end portions 1222 and 1224, can increase the overall clamping force of the clamp 1200 against the leaflets. In some embodiments, the leaflet-engaging portions 1214A and 1220A can also provide the elastic strain-recovery shape-maintenance functionality described in greater detail below with reference to FIG. 88.

Figure 86:
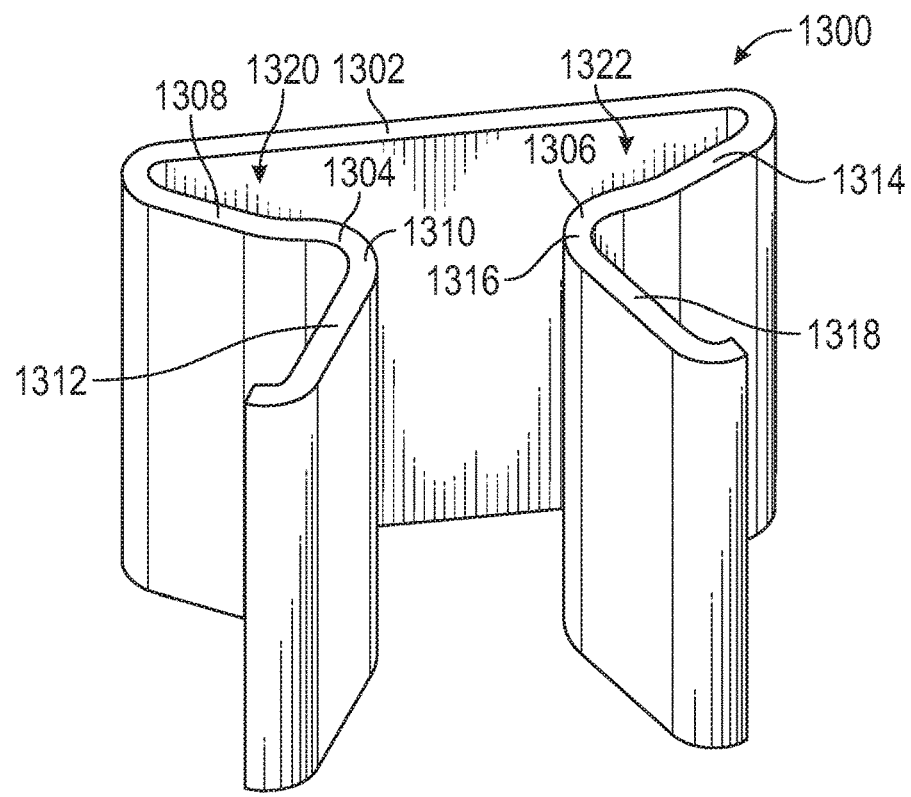
FIGS. 86-90 are various views showing additional embodiments of commissure clamps.
Figure 87:
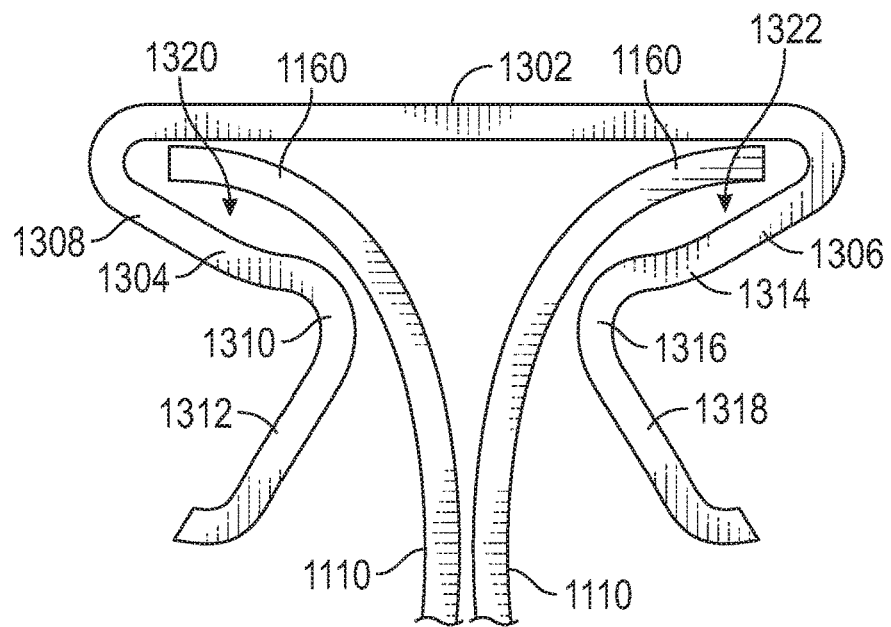
Figure 88:
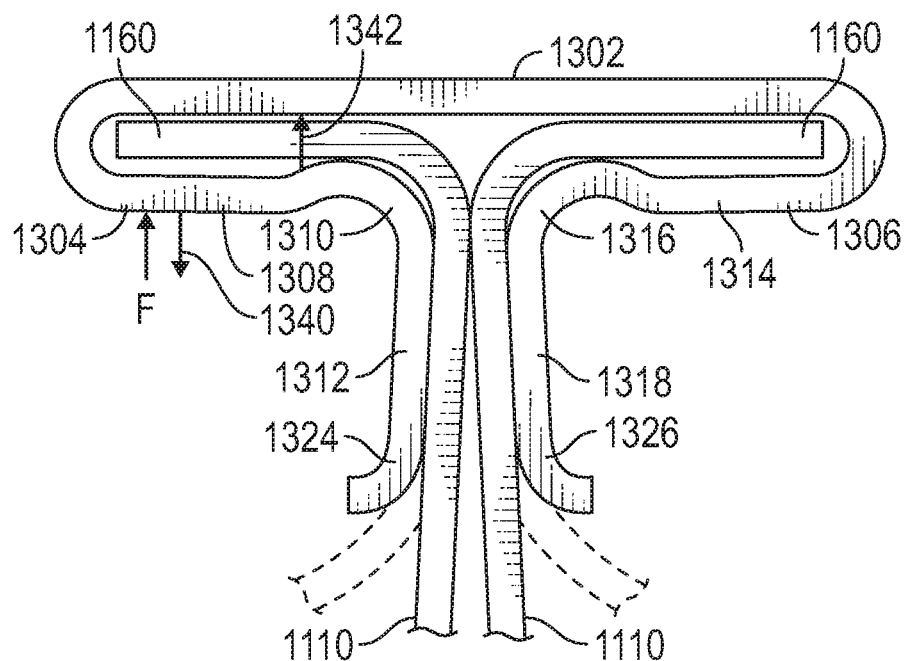

FIGS. 86-88 illustrate another embodiment of a commissure clamp 1300. Although the following discussion proceeds with reference to the commissures 1132 and the leaflets 1110 of the mechanically-expandable prosthetic valve 1100 of FIG. 81 that has actuators mounted on the frame, the commissure clamp 1300 may also be used with prosthetic heart valves that do not have actuators, such as self-expandable prosthetic heart valves and plastically-expandable prosthetic heart valves (e.g., such as those that are expanded to their functional size by inflating a balloon), such as the prosthetic valve 1500 illustrated in FIG. 96 and further described below. FIGS. 86 and 87 illustrate the commissure clamp 1300 in an initial, non-crimped configuration. The commissure clamp 1300 can include a straight main portion 1302, and first and second arms or clamp members 1304, 1306 extending from the main portion 1302 at an angle to the main portion. In the illustrated embodiment, the first clamp member 1304 includes a first portion 1308, a curved second portion configured as a leaflet-engaging portion 1310, and a third portion 1312 extending from the leaflet-engaging portion 1310 at an angle to the first portion 1308. Likewise, the second clamp member 1306 includes a first portion 1314, a curved second portion configured as a leaflet-engaging portion 1316, and a third portion 1318 extending from the leaflet-engaging portion 1316 at an angle to the first portion 1314. The left-hand portion of the main portion 1302 and the first portion 1308 of the first clamp member 1304 can define a first leaflet-receiving space 1320. Likewise, the right-hand portion of the main portion 1302 and the first portion 1314 of the second clamp member 1306 can define a second leaflet-receiving space 1322. The leaflet-receiving spaces 1320 and 1322 can be in communication with each other, and can extend at an angle to the line of coaptation between the leaflets 1110 at the commissure 1132, as best shown in FIGS. 88 and 89.

Referring to FIG. 87, when used to support a commissure, a commissure tab 1160 of one leaflet 1110 can be inserted into the leaflet-receiving space 1320, and a commissure tab 1160 of the other leaflet 1110 of the commissure can be inserted into the leaflet-receiving space 1322. The first and second clamp members 1304, 1306 can then be crimped to the closed position shown in FIG. 88, wherein the leaflets 1110 can be engaged, pressed, or clamped between the main portion 1302 and the respective leaflet-engaging portions 1310, 1316. In the crimped configuration illustrated in FIG. 88, the portions 1312 and 1318 of the first and second clamp members 1304, 1306, respectively, can extend radially inwardly relative to the frame. The portions 1312, 1318 can restrict movement of the leaflets 1110 such that the leaflets articulate about axes adjacent respective end portions 1324, 1326 of the first and second clamp members 1304, 1306 that are offset from the leaflet-engaging portions 1310, 1316 in a direction toward the center of the frame. This is illustrated in FIG. 88, in which the leaflets 1110 are shown in the open position in phantom and at or near the closed position in solid lines.

Figure 89:
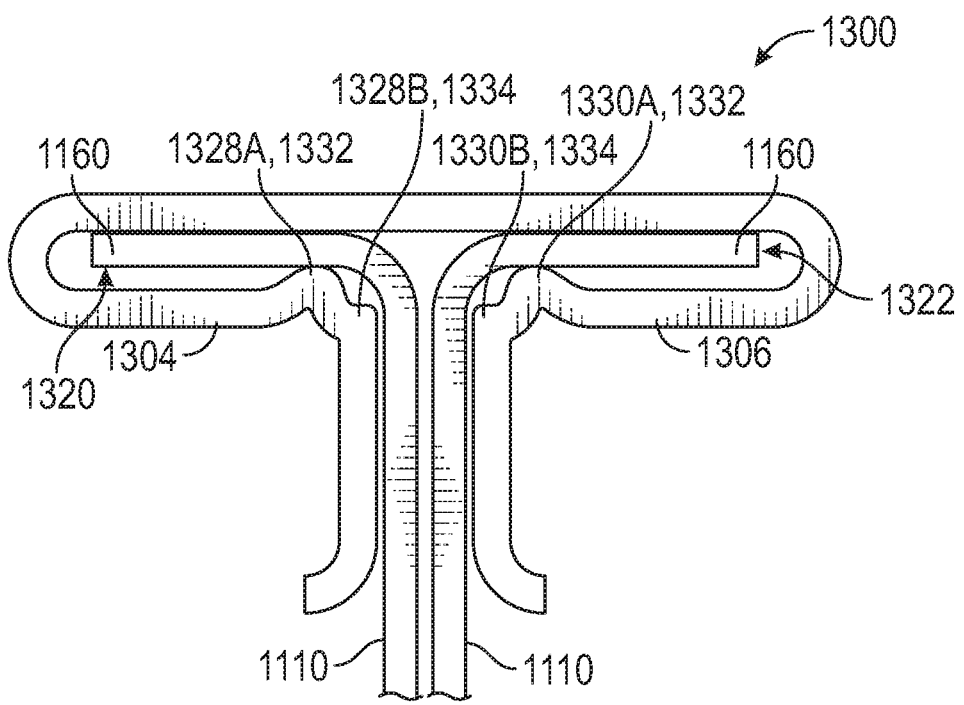

FIG. 89 illustrates another embodiment of the commissure clamp 1300 in which the first and second clamp members 1304, 1306 each include two leaflet-engaging portions. For example, in the embodiment of FIG. 89, the first clamp member 1304 includes leaflet-engaging portions 1328A and 1328B, and the second clamp member 1306 includes leaflet-engaging portions 1330A and 1330B. In the embodiment of FIG. 89, the leaflet-engaging portions 1328A and 1330A are located within the respective leaflet-receiving spaces 1320 and 1322, and include peaks 1332 oriented in a direction toward the main portion 1302. Meanwhile, the leaflet-engaging portions 1328B and 1330B can be angularly offset from the portions 1328A, 1330A and angled toward each other. In the illustrated embodiment, peaks 1334 of the leaflet-engaging portions 1328B, 1330B can be pointed, while the peaks 1332 of the portions 1328A, 1330A can be rounded, although the peaks of the leaflet-engaging portions can have any suitable shape depending upon the particular characteristics desired.

Figure 90:
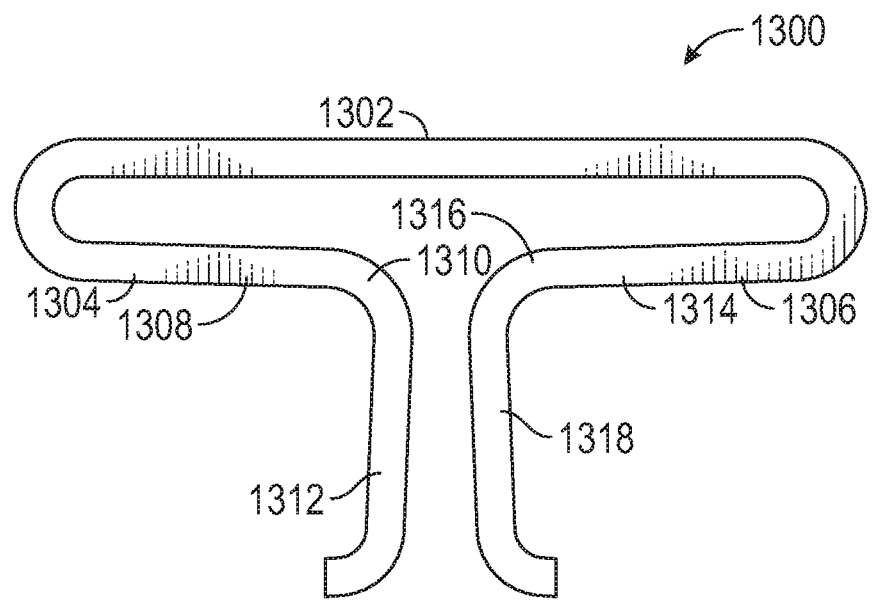

FIG. 90 illustrates another embodiment of the commissure clamp 1300 in which the first and third portions 1308, 1312 of the first clamp member 1304 form an angle (e.g., a right angle), and the leaflet-engaging portion 1310 forms an arc between the first and third portions. Likewise, the first and third portions 1314 and 1318 of the second clamp member 1306 form an angle (e.g., a right angle), and the leaflet-engaging portion 1316 forms an arc between the first and third portions of the second clamp member.

The commissure clamps of FIGS. 81-93 described above and below can be made from any of various plastically deformable materials with suitable elastic, plastic, and/or shape memory properties. For example, in certain embodiments the commissure clamps can be made from any of various metal alloys including Nitinol, titanium, stainless steel, etc. In certain configurations, the commissure clamps can be formed by plastically deforming the material (e.g., by stamping or bending). Additionally, as mentioned above, any of the clamps of FIGS. 81-93 can be used with prosthetic heart valve frames such as the type shown in FIG. 81, or with self-expandable frames (e.g., frames formed from Nitinol), or with plastically-expandable frames (e.g., the frame 12 described above or the frame 1500 described below) that can be expanded by inflating a balloon on which the prosthetic valve is mounted. A commissure clamp (e.g., a clamp 1300) can be mounted or coupled to a frame of a prosthetic heart valve in any convenient manner, such as by securing the clamp directly to the frame or on an actuator mounted on the frame. For example, a commissure clamp can be welded to the frame or an actuator, or secured to the frame or an actuator using an adhesive or with mechanical fasteners.

In embodiments where the clamps are used with a plastically-expandable frame, when force is applied to the commissure clamps during, for example, balloon expansion of the prosthetic valve, the first and second clamp members may be elastically and/or plastically deformed. In certain examples, a portion of the overall deformation of the various portions of the first and second clamp members may be elastic deformation (also referred to as elastic strain) that is recovered when the force is released. Thus, to ensure that the commissure clamps maintain a similar shape before and after expansion of the prosthetic valve, the bends or curved portions formed in the first and second clamp members may be configured such that elastic strain recovery in one or more curved portions offsets the elastic strain recovery of one or more adjacent curved portions. This can limit the overall change in shape of the clamp members when a force applied to the members is released (e.g., when the balloon is deflated).

For example, with reference again to FIG. 88, when the prosthetic valve is expanded, the balloon can apply a force to the first clamp member 1304 represented by the arrow F. During application of the force F, the first portion 1308 can bend or pivot in the direction of the arrow F. At least a portion of the overall strain of the first portion 1308 can be elastic strain. When the force F is released, this elastic strain can be recovered such that the first portion 1308 moves or pivots, for example, in a direction back toward the center of the valve, as indicated by arrow 1340. Meanwhile, during application of the force F, the portion 1310 can be pressed against the leaflet 1110 and/or against the main portion 1302, which can cause the portion 1310 to bend or deform radially inwardly. Thus, when the force F is released, the elastic strain recovery of the second portion 1310 can be in the radially outward direction generally indicated by arrow 1342. The elastic strain recovery of the first portion 1308 and the elastic strain recovery of the second portion 1310 are, thus, in opposite directions, and can cancel or nearly cancel one another such that overall movement of the first clamp member 1304 is minimized when the force F is released. The curved portions of the first and second clamp members of any of the commissure clamps described herein can be configured to produce such an effect.

Figure 91:
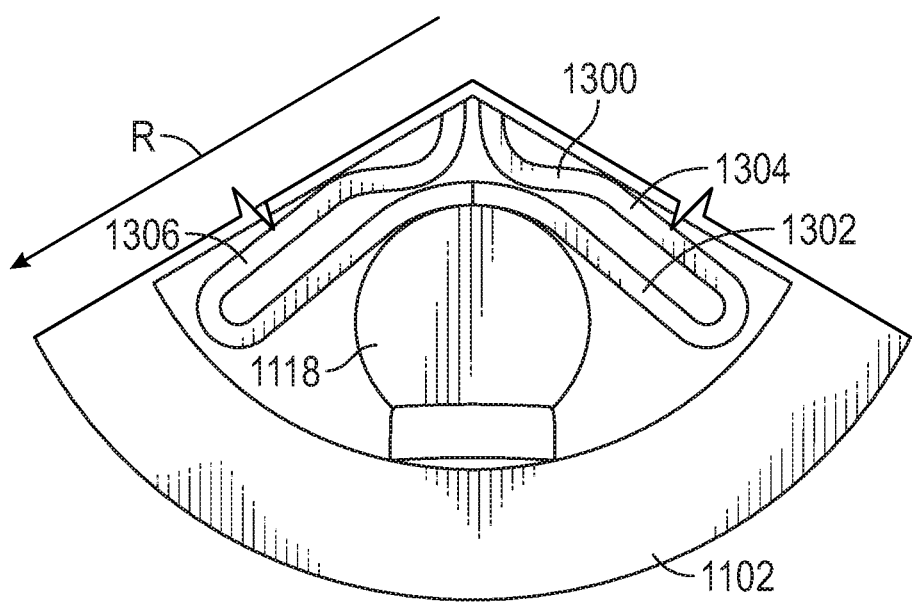
FIGS. 91-93 are plan views illustrating additional embodiments of commissure clamps situated within a schematic illustration of the frame of FIG. 81 in a radially collapsed configuration.
Figure 92:
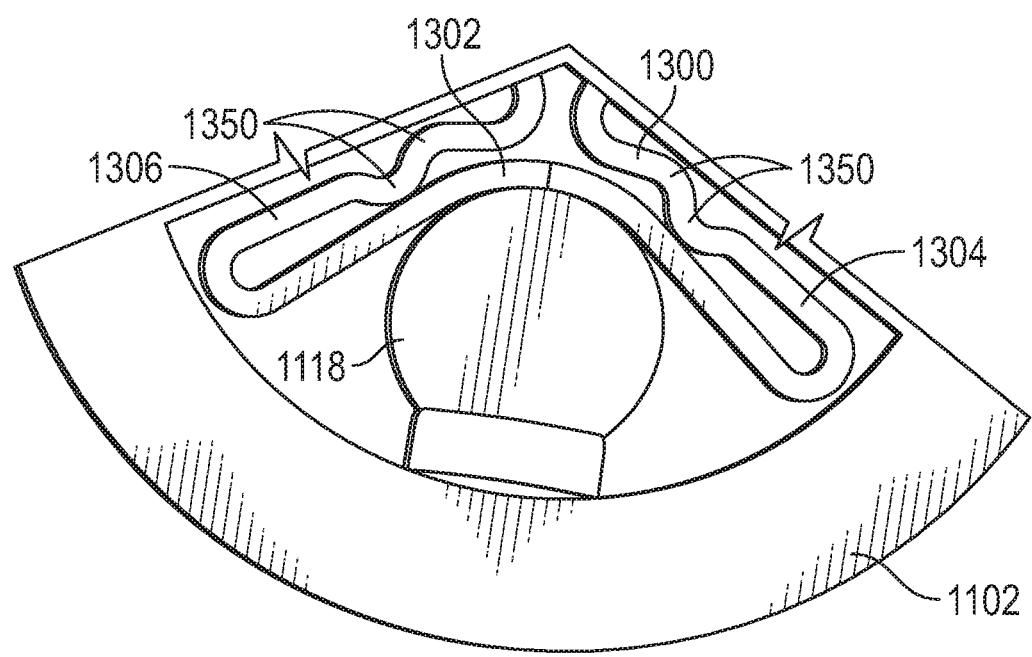
Figure 93:
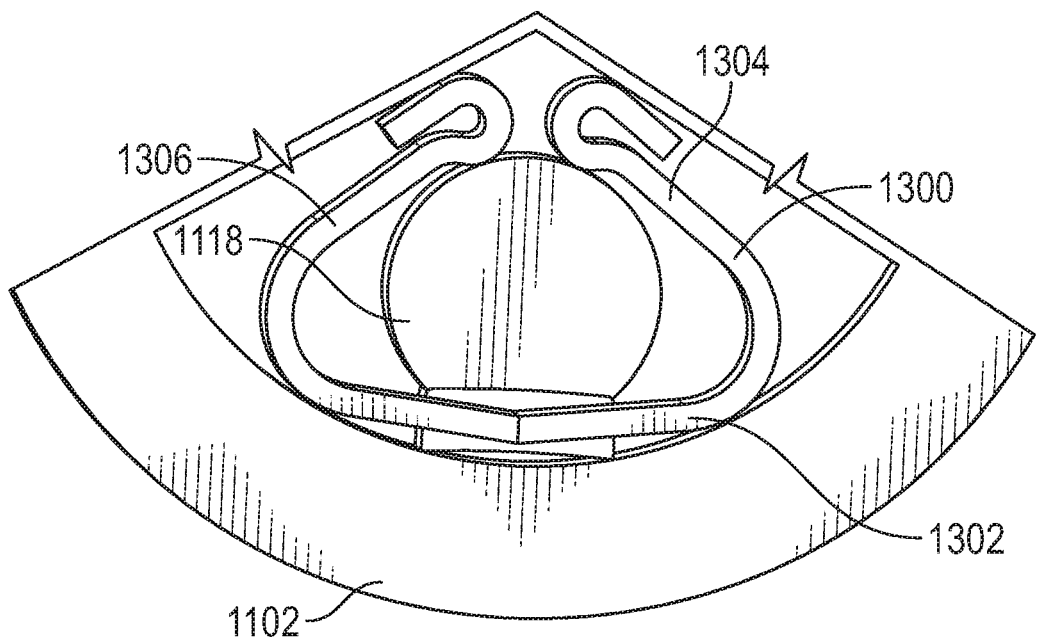

FIGS. 91-93 illustrate additional embodiments of commissure clamps 1300 within a schematic, partial cross-section of the frame 1102 of FIG. 81 in a radially collapsed configuration. In the configuration illustrated in FIG. 91, the main portion 1302 is curved such that it extends around the actuator 1118 of the frame 1102. Curving the main portion 1302 in this manner can allow the frame 1102 to be crimped to a reduced radius R with the commissure clamp inside the frame. The clamp 1300 can be secured to the outer surface of the actuator 1118, such as by welding, an adhesive and/or with mechanical fasteners. In the embodiment illustrated in FIG. 92, the first and second clamp members 1304, 1306 can include multiple curved leaflet-engaging portions 1350. FIG. 93 illustrates another embodiment in which the main portion 1302 extends behind the actuator 1118, and the first and second clamp members 1304, 1306 extend or curve around the locking unit in a radially-inward direction similar to the embodiments of FIGS. 81 and 85. The other commissure clamp embodiments described herein can also be curved in a similar manner, as desired.

In certain configurations, the commissure tabs of the leaflets of a prosthetic valve are wrapped with a layer of cloth in order to protect the leaflets from damage from the frame and/or other components of the prosthetic valve. In a test in which the leaflets were wrapped in a layer of cloth and inserted into the commissure clamp 1300 of FIG. 89, a force of 4.82 N to 6.84 N was required in order to pull the leaflet-cloth combination out of the commissure clamp. In a similar test, a force of 5.46 N was required to pull the leaflet-cloth combination out of the commissure clamp 1300 of FIG. 90. This demonstrates significantly improved performance over a metal tab folded 180 degrees to form a clamp without any leaflet-engaging portions, which required only 0.6 N to 1.72 N in order to pull the leaflet-cloth combination out of the clamp.

Where the various embodiments of the commissure clamp 1300 described above are used in combination with the mechanically-expandable valve 1100 of FIG. 81, the clamps can be secured to the actuators 1118 of the prosthetic valve 1100 in a variety of ways. For example, the main portion 1302 of the clamp 1300 can serve as a coupling portion and can be configured for attachment to the outer surface of the actuators 1118 (e.g., as illustrated in FIGS. 91 and 92) such as by welding, brazing, any of various adhesives, suturing, etc. The clamps 1300 may also be situated around the actuators 1118 with or without fixation (e.g., welding, adhesive, sutures, etc.) such that the arms of the clamps extend radially inwardly toward the center of the prosthetic valve from around the actuator, as illustrated in FIG. 93.

FIGS. 94 and 95 illustrate another embodiment of a commissure clamp 1400 similar to the commissure clamp 1300 of FIG. 87. The commissure clamp 1400 can include a curved main portion or outer portion 1402, and first and second arms or clamp members generally indicated at 1404 and 1406, respectively, that extend from the outer portion 1402. Referring to FIG. 95, the outer portion 1402 can be curved in the x-y plane (note Cartesian coordinate axes shown). In certain embodiments, the outer portion 1402 can have a radius of curvature R in the x-y plane that corresponds to the radius of the expanded prosthetic valve into which the clamp 1400 is incorporated (see, e.g., the prosthetic valve shown in FIG. 96 described below). Portions of the commissure clamp 1400 that extend parallel to the outer portion 1402 are referred to herein as extending circumferentially, while portions that are perpendicular to the outer portion 1402 are referred to as extending radially.

For example, in the illustrated embodiment the first clamp member 1404 includes a tightly curved first portion 1408, and a gently curved second portion 1410. The first portion 1408 can curve 180° such that the second portion 1410 extends circumferentially from the first portion 1408 in a direction back toward a center or mid-portion of the outer portion 1402 (e.g., in the positive x-direction in FIG. 95).

The second portion 1410 can also have the radius of curvature R in the x-y plane, similar to the outer portion 1402. The second portion 1410, the first portion 1408, and the left-hand side of the outer portion 1402 can together define a leaflet-receiving region 1412. The arm 1402 can further comprise a third portion 1414 extending radially from the second portion 1410 at an angle to the second portion 1410 (e.g., 90°). A gently curved fourth portion 1416 can extend circumferentially away from the third portion 1414 (e.g., in the negative x-direction) at an angle to the third portion (e.g., 90°) and parallel to the second portion 1410. In certain embodiments, the fourth portion 1416 can also comprise the radius of curvature R in the x-y plane.

The second clamp member 1406 can be configured similarly to the first clamp member with a tightly curved first portion 1418 with a curvature of 180° such that a gently curved second portion 1420 that extends from the first portion 1418 doubles back along the outer portion 1402 parallel to but spaced apart from the outer portion 1402. The second portion 1420, the first portion 1418, and the right-hand portion of the outer portion 1402 can together define a leaflet-receiving region 1422 opposite the leaflet-receiving region 1412 and in fluid communication with the leaflet-receiving region 1412. A third portion 1424 can extend radially from the second portion 1420 at an angle to the second portion (e.g., 90°) and spaced apart from the third portion 1414 of the first arm 1404. In the illustrated embodiment, the portions 1414 and 1424 can be angled toward each other. A gently curved fourth portion 1426 can extend from the third portion 1424 at an angle to the third portion 1424 (e.g., 90°), and in the opposite direction from the fourth portion 1416 of the first arm 1402 (e.g., in the positive x-direction). In the illustrated embodiment, the portions 1420 and 1426 of the second clamp 1406 can comprise the radius of curvature R in the x-y plane, similar to the portions 1410 and 1416 of the first clamp member 1404.

Figure 96:
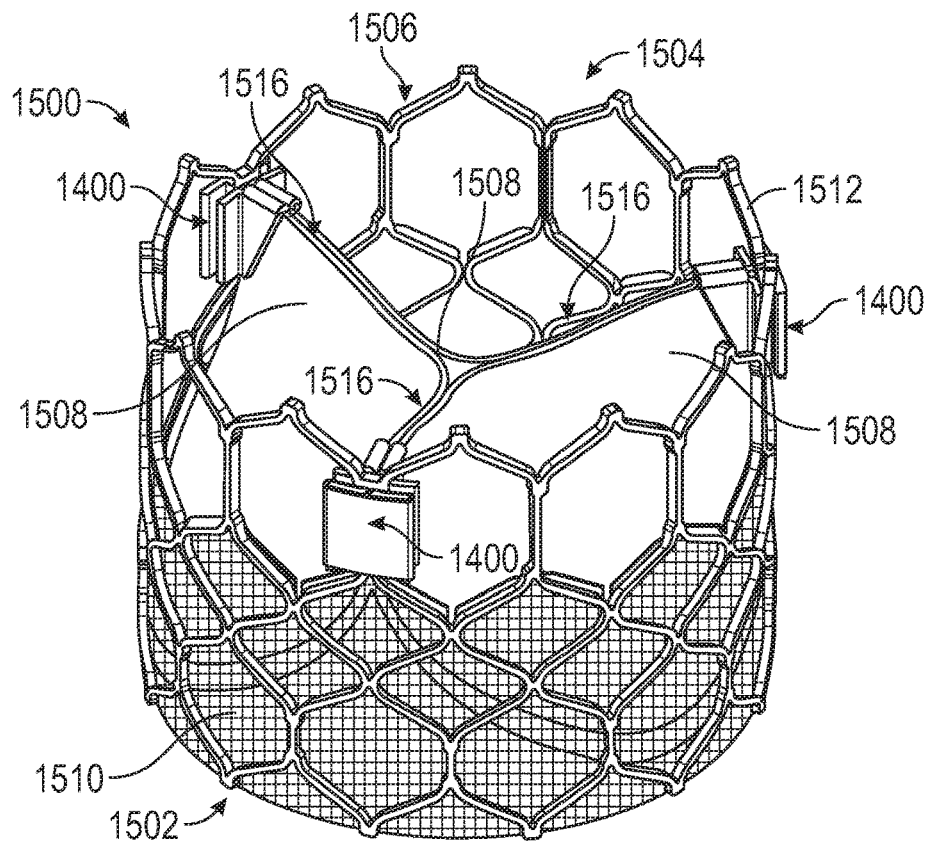
FIG. 96 is a perspective view illustrating an embodiment of a prosthetic heart valve including the commissure clamp of FIGS. 94 and 95.
Figure 97:
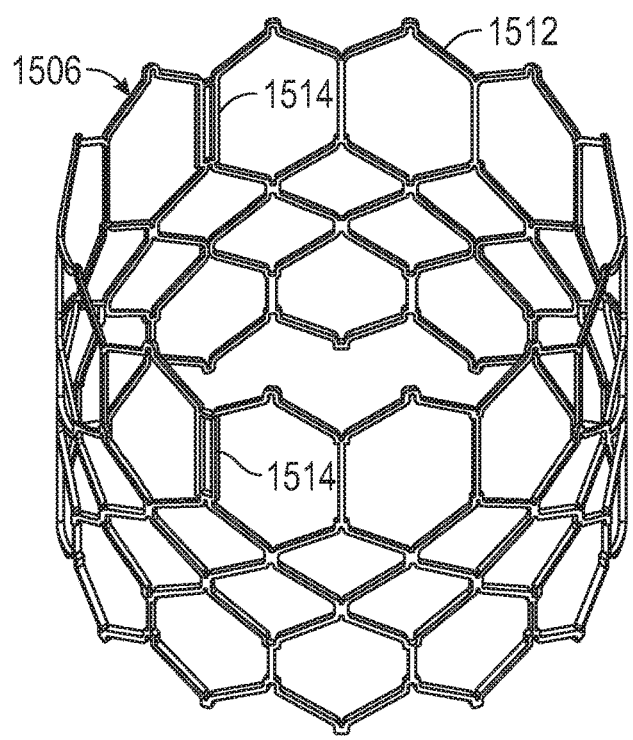
FIG. 97 is a perspective view of the frame of the prosthetic heart valve of FIG. 96.

The commissure clamp 1400 can be configured for use with the prosthetic heart valve 1500 illustrated in FIGS. 96 and 97. A transcatheter heart valve with a valve profile similar to the prosthetic valve shown in FIGS. 96 and 97 is the Edwards Lifesciences SAPIEN 3™ valve, which is described in detail in U.S. Publication No. 2012/0123529 incorporated by reference above. The prosthetic valve 1500 in FIGS. 96 and 97 has an inflow end 1502 and an outflow end 1504, includes a frame or stent 1506, and a leaflet structure comprising a plurality of leaflets 1508 supported inside the frame 1506. In the illustrated embodiment, the leaflet structure includes three leaflets 1508 configured to collapse in a tricuspid arrangement (FIG. 96) similar to the native aortic valve, although the prosthetic valve can also include two leaflets configured to collapse in a bicuspid arrangement in the manner of the native mitral valve, or more than three leaflets, as desired. In some embodiments, a skirt 1510 can be attached to an inner surface of the frame 1506 to serve as an attachment surface for the valve leaflets 1508.

FIG. 97 illustrates the frame 1506 without the leaflet structure and the skirt. The frame 1506 can be formed by a plurality of angled strut members 1512 arranged end-to-end to form a plurality of rows or rungs of strut members that extend circumferentially around the frame 1506, as further described in U.S. Publication No. 2012/0123529, incorporated by reference above. The frame 1506 can be formed with a plurality of circumferentially spaced slots, or commissure windows, 1514 (three in the illustrated embodiment) that are adapted to mount the commissures 1516 of the valvular structure to the frame, as described in greater detail below. The frame 1506 can be made of any bio-compatible expandable material that permits both crimping to a radially collapsed state and expansion back to the expanded functional state illustrated in FIGS. 96 and 97. For example, in embodiments where the prosthetic valve is a self-expandable prosthetic valve that expands to its functional size under its own resiliency, the frame 1506 can be made of Nitinol or another self-expanding material. In other embodiments, the prosthetic valve can be a plastically expandable valve that is expanded to its functional size by a balloon or another expansion device, in which case the frame can be made of a plastically expandable material, such as stainless steel or a cobalt-chromium alloy. Other suitable materials can also be used.

Figure 98:
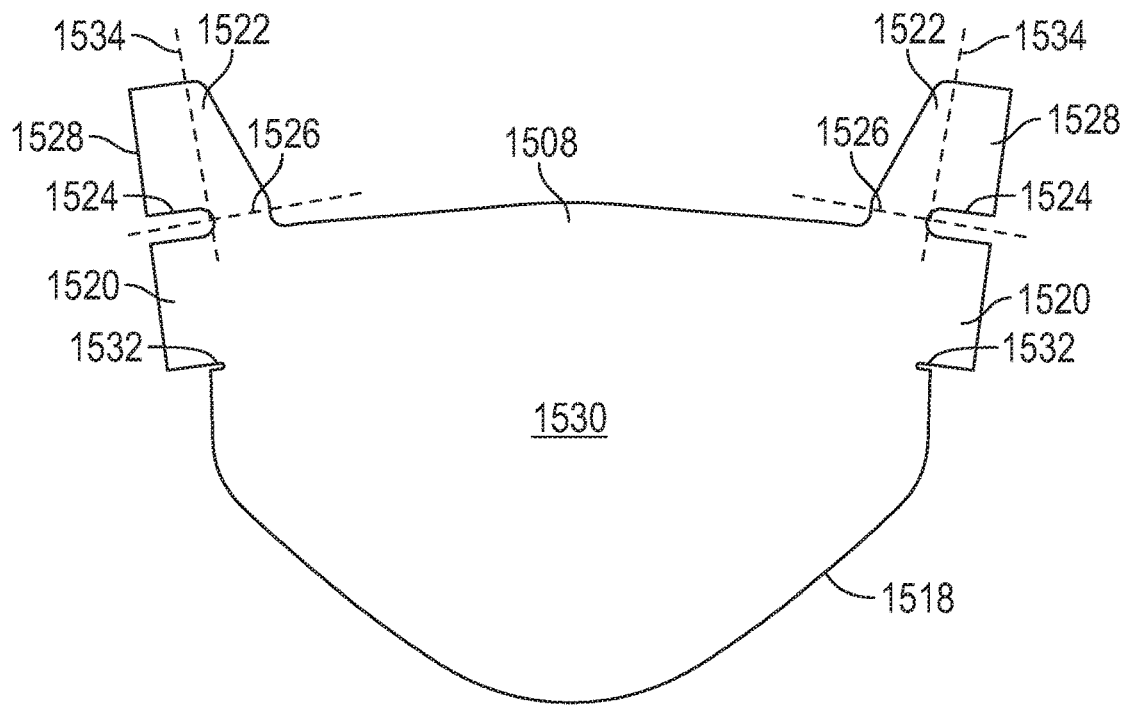
FIG. 98 is a side elevation view of a leaflet of the prosthetic heart valve of FIG. 96, according to one embodiment.

FIG. 98 illustrates a leaflet 1508 of the prosthetic valve 1500 in an unfolded, laid-flat configuration. The leaflet 1508 can comprise a lower edge portion 1518 that can be secured to the frame 1506 by suturing, and/or in the manner of any of the previously described embodiments. The lower edge portion 1518 terminates at its upper ends at two laterally projecting integral lower tab portions 1520. Projecting from the upper corners of the leaflet 1508 are integral upper tab portions 1522. The upper tabs 1522 can be spaced from the lower tabs 1520 by laterally extending gaps or recesses 1524 formed in the leaflet. The lower tabs 1520 can also be spaced from the main body or belly 1530 of the leaflet by relatively small gaps or recesses 1532. With the lower tabs 1520 immobilized in the commissure clamp 1400 as further described below, the recesses 1532 can allow the main body 1530 to articulate relative to the lower tabs 1520 during valve operation without tearing the tabs.

Figure 99:
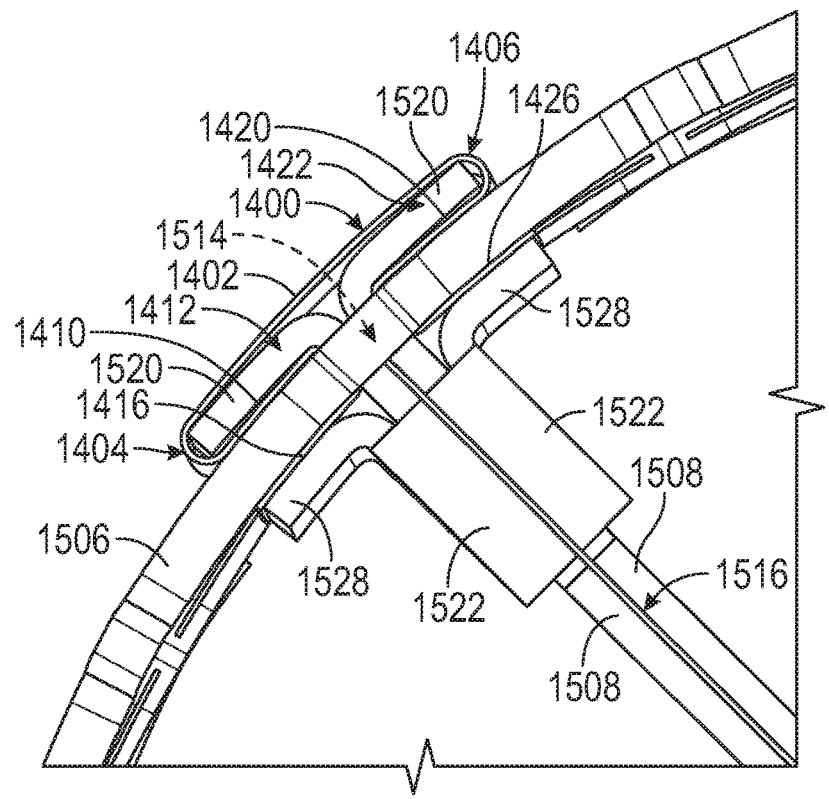
FIG. 99 is a magnified top view illustrating a commissure of the prosthetic heart valve of FIG. 96 including the commissure clamp of FIG. 94.
Figure 100:
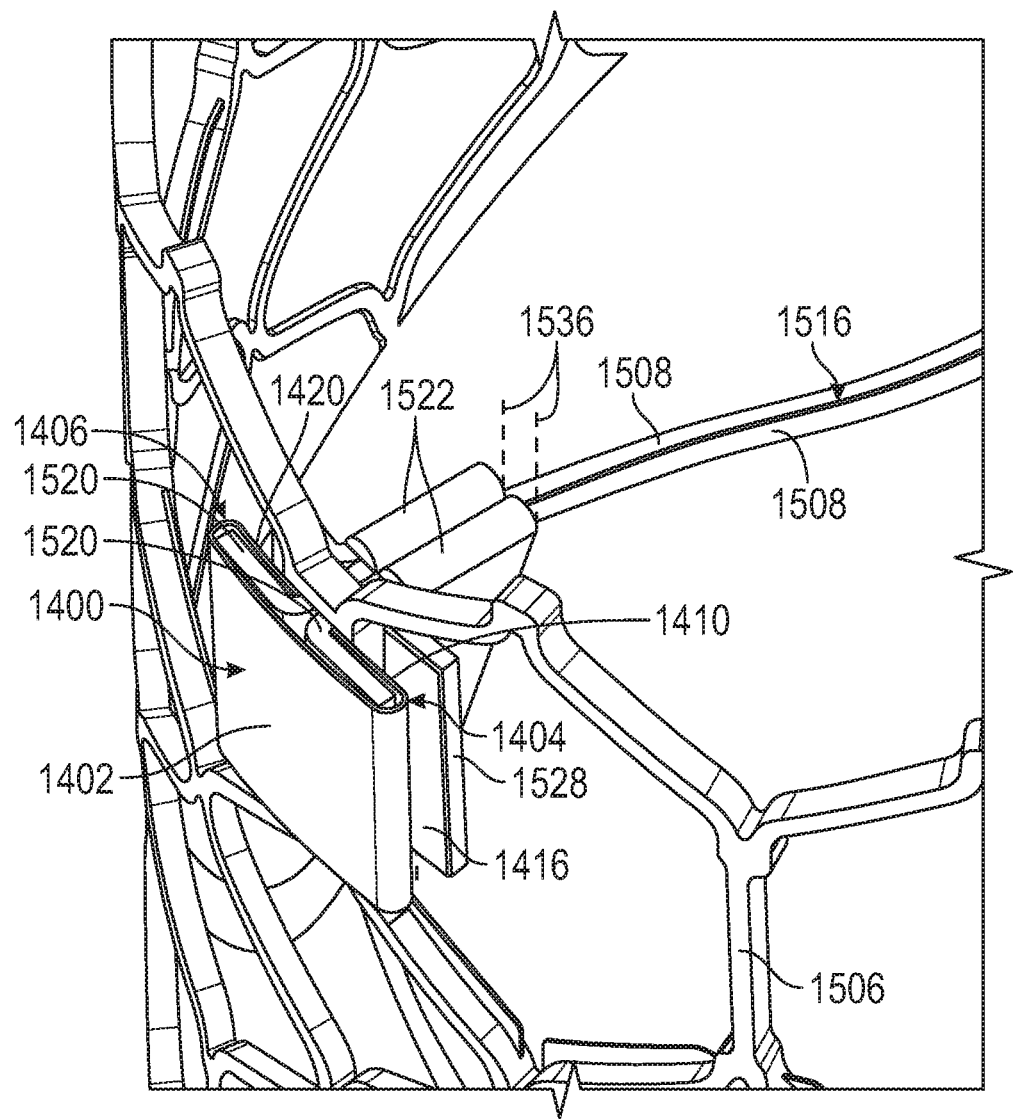
FIG. 100 is a perspective view of the commissure of FIG. 99.

With reference to FIGS. 99 and 100, to assemble a commissure 1516, a commissure clamp 1400 is inserted through one of the three commissure windows 1514 (FIG. 97) such that the portions 1414 and 1424 (FIG. 95) of the respective clamp members 1404 and 1406 extend through the commissure window 1514 to the inside of the frame 1506. Thus, with reference to FIGS. 95 and 99, the outer portion 1402, the portion 1410 of the first clamp member 1404, the portion 1420 of the second clamp member 1406, and the two leaflet-receiving regions 1412 and 1422 can be outside the frame 1506. For example, in the illustrated embodiment, the portions 1410 and 1420 of the first and second clamp members 1404 and 1406, respectively, can be disposed against or adjacent the outer surface of the frame 1506.

In certain configurations, the portions 1416 and 1426 can initially extend straight from the respective portions 1414 and 1424 without the 90° bends illustrated in FIG. 95 in order to facilitate insertion of the clamp members through the commissure windows. The lower tab portion 1520 of the leaflet 1508 on the lower left-hand side of FIG. 99 can then be inserted between the portions 1414 and 1424 (see FIG. 95) and into the leaflet-receiving portion 1412 of the first clamp member 1404. Likewise, the lower tab portion 1520 of the leaflet 1508 on the upper right-hand side of FIG. 99 can be inserted between the portions 1414 and 1424 and into the leaflet-receiving portion 1422.

In embodiments in which the portions 1416 and 1426 have not yet been folded into position, the clamp members 1404 and 1406 can be folded or bent such that the portions 1416 and 1426 lie against the interior surface of the frame 1506, as illustrated in FIG. 99. In this manner, the first clamp member 1404 can clamp the frame 1506 (e.g., the side wall of the commissure window 1514) between the portions 1410 and 1416, and the second clamp member 1406 can clamp the frame (e.g., the opposite side wall of the commissure window) between the portions 1420 and 1426. This can prevent the commissure clamp 1400 from moving or becoming dislodged during valve operation.

Referring again to FIG. 98, the upper tabs 1522 of the leaflets can then be folded downwardly in a direction toward the belly 1530 of the leaflet along the fold line 1526. A radially outward portion 1528 of each of the upper tabs 1522 can then be folded about a fold line 1534 such that the portions 1528 extend circumferentially along the interior of the frame 1506. For example, with reference to FIG. 99, the radially outward portion 1528 of the upper tab 1522 on the lower left-hand side of FIG. 99 can be folded along the fold line 1534 (FIG. 98) such that the portion 1528 lies against the clamp portion 1416. Meanwhile, the portion 1528 of the upper tab 1522 on the upper right-hand side of FIG. 99 can be folded along the respective fold line 1534 such that the portion 1528 lies against the clamp portion 1426 to form the commissure 1516. In certain embodiments, the leaflets 1508 may be further secured to the commissure clamp 1400 and/or to the frame 1506 with, for example, sutures.

Referring to FIG. 100, during valve operation the leaflets 1508 can articulate about axes 1536 located at or near the radially inner ends of the folded upper tabs 1522, and perpendicular to the plane of the page in FIG. 99. In the illustrated embodiment, the upper tabs 1522 can function to keep the moving portions of the leaflets 1508 away from the frame during valve operation. When the valve is crimped, the leaflets 1508 can separate at a location closer to the frame (e.g., proximate the fold line 1534 in FIG. 98, allowing the leaflets to fold more predictably and evenly inside of the frame during crimping of the prosthetic valve.

In other embodiments, the commissure clamp configurations shown in FIGS. 86-93 can be adapted for use with the prosthetic valve 1500, and can be used to assemble a commissure in a manner similar to that described above with respect to the commissure clamp 1400. For example, the portion 1312 of the clamp member 1304 and the portion 1318 of the clamp member 1306 of the commissure clamp 1300 of FIG. 86 can be inserted through a commissure window 1514 and crimped to the closed position in a manner similar to the process described above with reference to the commissure clamp 1400.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, the lower end of the valve is its inflow end and the upper end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, the terms "integrally formed" and "unitary construction" refer to a construction that does not include any welds, fasteners, or other means for securing separately formed pieces of material to each other.

Unless otherwise indicated, all numbers expressing quantities of components, molecular weights, percentages, temperatures, forces, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under test conditions/methods familiar to those of ordinary skill in the art. When directly and explicitly distinguishing embodiments from discussed prior art, the embodiment numbers are not approximates unless the word "about" is recited. Furthermore, not all alternatives recited herein are equivalents.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims.

The invention claimed is:

1. A prosthetic valve, comprising:
   an annular frame including a plurality of angled strut members, the frame being radially collapsible to a collapsed configuration and radially expandable to an expanded configuration;
   a leaflet structure situated at least partially within the frame, the leaflet structure comprising a plurality of leaflets, each leaflet comprising opposing commissure tab portions on opposite sides of the leaflet, each commissure tab portion being paired with an adjacent commissure tab portion of an adjacent leaflet to form one or more commissures; and a plurality of commissure support elements comprising a material different from the leaflets, a commissure support element being positioned at each of the one or more commissures, each of the commissure support elements comprising a first member and a second member, the first and second members being separable from each other and configured to receive leaflets therebetween;

wherein the first and second members of the commissure support elements are detached from the frame, and spaced radially inwardly from the frame such that the first and second members contact the leaflets radially inward from the frame and limit movement of the leaflets so that the leaflets articulate at a location that is spaced radially inwardly from the frame during valve operation; and wherein the commissure tab portions of each leaflet are folded to form four layers, and the first and second members are situated between second and third layers of the respective commissure tab portions.

2. The prosthetic valve of claim 1, wherein the first member of each commissure support element is secured to one of the adjacent commissure tab portions, and the second member of each commissure support element is secured to the other of the adjacent commissure tab portions.

3. The prosthetic valve of claim 1, wherein the commissure tab portions of each commissure are folded around the first and second members of an adjacent commissure support element.

4. The prosthetic valve of claim 1, wherein:
the first and second members of each commissure support element are spaced apart from each other; and
the prosthetic valve further comprises an attachment member secured to and extending between the commissure tab portions of the leaflets of each commissure.

5. The prosthetic valve of claim 4, wherein:
each commissure further comprises an outer support member including a main body portion positioned within the frame and an extension portion extending over an outflow end of the frame and situated on the outside of the frame; and
the attachment member of each commissure is situated around the extension portion of the outer support member such that the commissure is supported within the frame.

6. The prosthetic valve of claim 1, wherein the first and second members of each commissure support element at least partially define a commissure window through which the commissure tab portions of the leaflets extend.

7. The prosthetic valve of claim 6, wherein the first and second members of each commissure support element are secured to each other with sutures.

8. The prosthetic valve of claim 1, wherein the second layers of the folded commissure tab portions extend radially inwardly of the commissure support elements such that the leaflets articulate about edge portions of the second layers.

9. The prosthetic valve of claim 1, wherein the first and second members of each commissure support element mechanically interlock with each other to form a commissure window.

10. The prosthetic valve of claim 9, wherein the first member of each commissure support element defines openings configured to receive corresponding projections on the second members.

11. The prosthetic valve of claim 1, further comprising a commissure attachment member at each commissure, and wherein the commissure tab portions of each commissure are received in the respective commissure attachment member.

12. The prosthetic valve of claim 11, wherein each commissure attachment member is folded to form a central outer portion and first and second side portions.

13. The prosthetic valve of claim 12, wherein each of the first and second side portions of the commissure attachment members comprise first and second layers.

14. The prosthetic valve of claim 13, wherein end portions extend from the first and second side portions of the commissure attachment members and form one of the first or second layers of the commissure attachment members.

15. The prosthetic valve of claim 12, wherein each side portion of each commissure attachment member is secured to a commissure tab portion of the respective commissure.

16. The prosthetic valve of claim 15, wherein each side portion of each commissure attachment member is secured to a commissure tab portion of the respective commissure by suturing.

17. The prosthetic valve of claim 11, further comprising:
an inner sleeve at each commissure, the inner sleeves being configured to extend around the commissure tab portions of each respective commissure; and
an outer support member secured to the commissure attachment member at each commissure, at least a portion of the outer support member being positioned outside the frame.

18. The prosthetic valve of claim 1, wherein the commissure support elements comprise fabric.

19. A prosthetic valve, comprising:
an annular frame including a plurality of angled strut members, the frame being radially collapsible to a collapsed configuration and radially expandable to an expanded configuration;
a leaflet structure situated at least partially within the frame, the leaflet structure comprising a plurality of leaflets, each leaflet comprising opposing commissure tab portions on opposite sides of the leaflet, each commissure tab portion being paired with an adjacent commissure tab portion of an adjacent leaflet to form one or more commissures; and
a plurality of commissure support elements comprising a material different from the leaflets, a commissure support element being positioned at each of the one or more commissures, each of the commissure support elements comprising a first member and a second member, the first and second members being separable from each other and configured to receive leaflets therebetween;
wherein the first and second members of each commissure support element are detached from the frame, spaced radially inwardly from the frame such that the first and second members contact the leaflets radially inward from the frame, and mechanically interlock with each other to define a commissure window configured to receive the commissure tab portions of respective leaflets and limit movement of the commissure tab portions such that the leaflets articulate at a location that is spaced radially inwardly from the frame during valve operation; and
wherein the commissure tab portions of each leaflet are folded to form four layers, and the first and second members are situated between second and third layers of the respective commissure tab portions.

20. The prosthetic valve of claim 19, wherein the first member of each commissure support element defines openings configured to receive corresponding projections on the second members.

21. The prosthetic valve of claim 20, wherein:
the first member of each commissure support element is a C-shaped member comprising a main body portion and first and second coupling portions extending laterally from the main body portion; and
the openings are defined in the first and second coupling portions.

22. The prosthetic valve of claim 20, wherein:
each of the coupling portions of the first members of the commissure support elements comprise a pair of laterally-extending tines that define a T-shaped recess; and
the second member of each commissure support element comprises a pair of T-shaped extension portions configured to be received in the corresponding T-shaped recesses of the first member.

23. The prosthetic valve of claim 20, wherein the projections of the second members are configured as fastening portions that are bent to secure the first and second members together.

24. A prosthetic valve, comprising:
an annular frame including a plurality of angled strut members, the frame being radially collapsible to a collapsed configuration and radially expandable to an expanded configuration;
a leaflet structure situated at least partially within the frame, the leaflet structure comprising a plurality of leaflets, each leaflet comprising opposing commissure tab portions on opposite sides of the leaflet, each commissure tab portion being paired with an adjacent commissure tab portion of an adjacent leaflet to form one or more commissures;
a plurality of commissure support elements comprising a material different from the leaflets, a commissure support element being positioned at each of the one or more commissures, each of the commissure support elements comprising a first member and a second member, the first and second members being separable from each other and configured to receive leaflets therebetween; and
a plurality of commissure attachment members, a commissure attachment member being positioned at each commissure, the commissure tab portions of each commissure being received in the respective commissure attachment member, each commissure attachment member being folded to form a central outer portion and first and second side portions, wherein each of the first and second side portions of the commissure attachment members comprises first and second layers; and
wherein the first and second members of the commissure support elements are detached from the frame, and spaced radially inwardly from the frame such that the first and second members contact the leaflets radially inward from the frame and limit movement of the leaflets so that the leaflets articulate at a location that is spaced radially inwardly from the frame during valve operation.

* * * * *